US012667550B2

(12) United States Patent
Strupp

(10) Patent No.: US 12,667,550 B2
(45) Date of Patent: Jun. 30, 2026

(54) TREATMENT OF LATE-ONSET NEURODEGENERATIVE DISEASES IN HETEROZYGOUS NPC1 GENE MUTATION CARRIERS

(71) Applicant: IntraBio Ltd., London (GB)

(72) Inventor: Michael Strupp, Munich (DE)

(73) Assignee: IntraBio Ltd., London (GB)

( * ) Notice: Subject to any disclaimer, the term of this patent is extended or adjusted under 35 U.S.C. 154(b) by 781 days.

(21) Appl. No.: 17/758,759

(22) PCT Filed: Jan. 13, 2021

(86) PCT No.: PCT/IB2021/050236

§ 371 (c)(1),
(2) Date: Jul. 13, 2022

(87) PCT Pub. No.: WO2021/144720

PCT Pub. Date: Jul. 22, 2021

(65) Prior Publication Data

US 2023/0051742 A1 Feb. 16, 2023

Related U.S. Application Data

(60) Provisional application No. 62/960,637, filed on Jan. 13, 2020.

(51) Int. Cl.
*A61K 31/198* (2006.01)
*A61P 25/28* (2006.01)

(52) U.S. Cl.
CPC ............ *A61K 31/198* (2013.01); *A61P 25/28* (2018.01)

(58) Field of Classification Search
CPC .............................. A61K 31/198; A61P 25/28
See application file for complete search history.

(56) References Cited

U.S. PATENT DOCUMENTS

| | | | |
|---|---|---|---|
| 8,202,525 | B2 | 6/2012 | Crain et al. |
| 9,155,719 | B2 | 10/2015 | Rekik |
| 9,283,181 | B2 | 3/2016 | Calias et al. |
| 10,905,670 | B2 | 2/2021 | Factor et al. |
| 10,950,670 | B2 | 3/2021 | Luo |

(Continued)

FOREIGN PATENT DOCUMENTS

| | | |
|---|---|---|
| CN | 103079550 A | 5/2013 |
| CN | 103814046 A | 5/2014 |

(Continued)

OTHER PUBLICATIONS

Tatiana Bremova et al: "Acetyl-DL-leucine in Niemann-Pick type C: A case series", Neurology, vol. 85, No. 16, 2015, pp. 1368-1375 (Year: 2015).*

(Continued)

*Primary Examiner* — Deborah D Carr
(74) *Attorney, Agent, or Firm* — Sterne, Kessler, Goldstein & Fox P.L.L.C.

(57) ABSTRACT

The present disclosure provides methods of treating, preventing, or delaying the onset of a late-onset neurodegenerative disease, e.g., Niemann-Pick type C, or a symptom thereof in a subject in need thereof, comprising administering a therapeutically effective amount of acetyl-leucine to the subject, wherein the subject is heterozygous NPC1 gene mutation carrier.

20 Claims, 11 Drawing Sheets

(56) References Cited

U.S. PATENT DOCUMENTS

Figure 1:
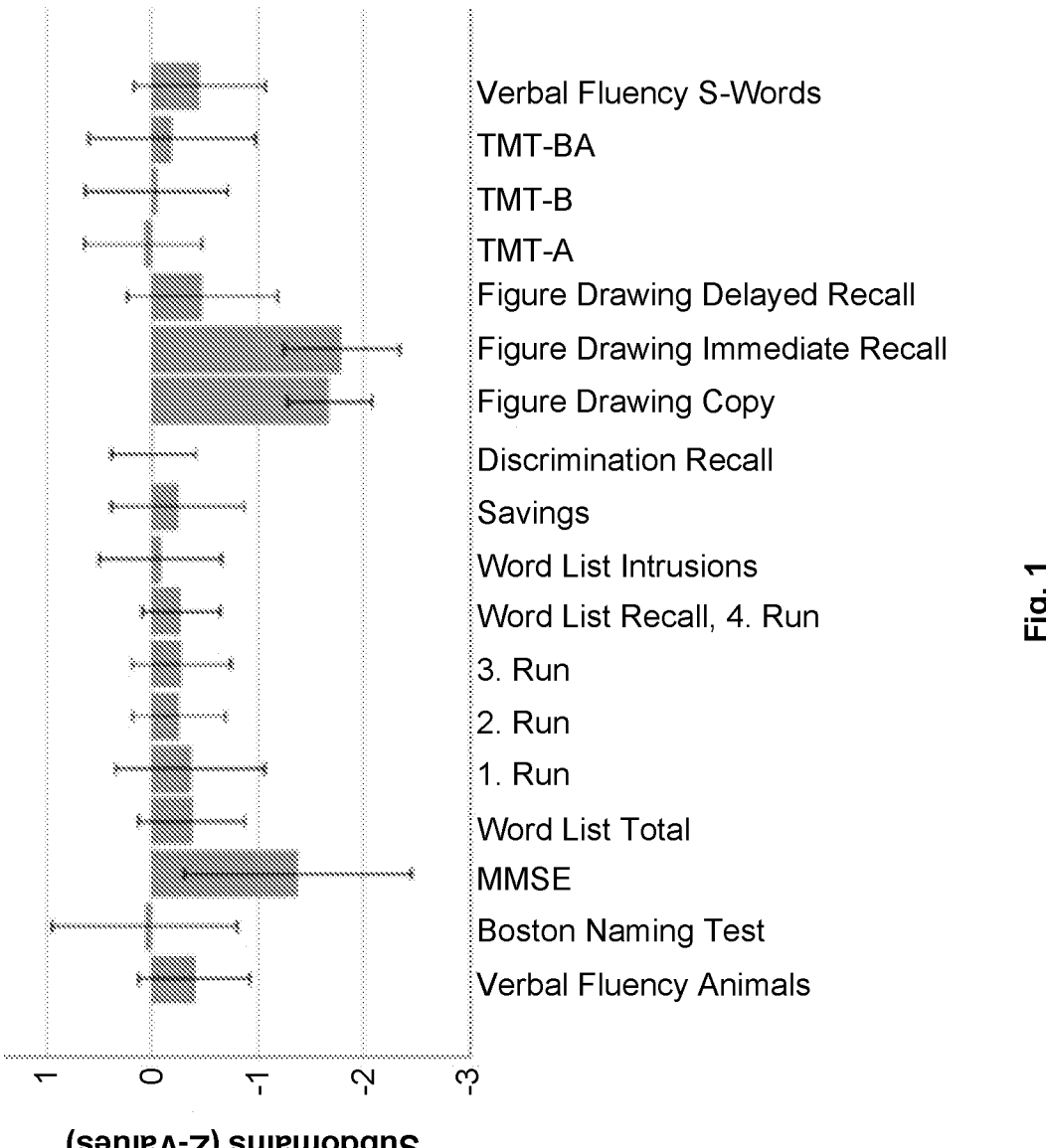

| | | | |
|---|---|---|---|
| 11,083,718 | B2 | 8/2021 | Strupp |
| 11,400,067 | B2 | 8/2022 | Strupp |
| 11,471,434 | B2 | 10/2022 | Strupp et al. |
| 11,660,279 | B2 | 5/2023 | Factor et al. |
| 11,793,782 | B2 | 10/2023 | Factor |
| 11,998,518 | B2 | 6/2024 | Factor et al. |
| 12,144,792 | B2 | 11/2024 | Strupp |
| 12,145,899 | B2 | 11/2024 | Mann |
| 12,329,733 | B2 | 6/2025 | Factor et al. |
| 2002/0095135 | A1 | 7/2002 | Meeker et al. |
| 2004/0127501 | A1 | 7/2004 | Chen et al. |
| 2006/0063827 | A1 | 3/2006 | Yu et al. |
| 2006/0128717 | A1 | 6/2006 | Sun et al. |
| 2006/0235022 | A1 | 10/2006 | Sun |
| 2006/0235055 | A1 | 10/2006 | Kyle et al. |
| 2006/0241117 | A1 | 10/2006 | Sun |
| 2007/0027159 | A1 | 2/2007 | Kyle et al. |
| 2007/0032500 | A1 | 2/2007 | Sun et al. |
| 2007/0276041 | A1 | 11/2007 | Oonuki et al. |
| 2008/0214649 | A1 | 9/2008 | Yu et al. |
| 2009/0318555 | A1 | 12/2009 | Fabre et al. |
| 2013/0123239 | A1 | 5/2013 | Kurose |
| 2013/0142888 | A1 | 6/2013 | Rekik |
| 2013/0317036 | A1 | 11/2013 | Rekik |
| 2014/0080885 | A1 | 3/2014 | Pennypacker et al. |
| 2014/0350056 | A1 | 11/2014 | Yu |
| 2019/0046486 | A1 | 2/2019 | De Rienzo et al. |
| 2019/0083438 | A1 | 3/2019 | Factor et al. |
| 2019/0201359 | A1 | 7/2019 | Strupp |
| 2020/0179320 | A1 | 6/2020 | Strupp |
| 2020/0253905 | A1 | 8/2020 | Strupp et al. |
| 2020/0338034 | A1 | 10/2020 | Factor |
| 2021/0106548 | A1 | 4/2021 | Factor et al. |
| 2021/0196659 | A1 | 7/2021 | Factor |
| 2021/0361632 | A1 | 11/2021 | Strupp |
| 2022/0024858 | A1 | 1/2022 | Mann |
| 2022/0142959 | A1 | 5/2022 | Factor et al. |
| 2022/0331278 | A1 | 10/2022 | Strupp |
| 2022/0362189 | A1 | 11/2022 | Factor et al. |
| 2023/0201150 | A1 | 6/2023 | Strupp |
| 2023/0210799 | A1 | 7/2023 | Strupp |
| 2023/0346732 | A1 | 11/2023 | Factor et al. |
| 2024/0189267 | A1 | 6/2024 | Strupp |
| 2024/0197663 | A1 | 6/2024 | Strupp |
| 2024/0208895 | A1 | 6/2024 | Churchill |
| 2025/0129011 | A1 | 4/2025 | Mann |

FOREIGN PATENT DOCUMENTS

| | | | |
|---|---|---|---|
| EP | 0226304 | A1 | 6/1987 |
| EP | 0288447 | A1 | 10/1988 |
| FR | 2905600 | A1 | 3/2008 |
| JP | 2009269856 | A | 11/2009 |
| JP | 2014503596 | A | 2/2014 |
| JP | 2016513084 | A | 5/2016 |
| RU | 2012151575 | A | 7/2014 |
| RU | 2680413 | C1 | 2/2019 |
| WO | WO-9526325 | A2 | 10/1995 |
| WO | WO-9621464 | A1 | 7/1996 |
| WO | WO-2006036634 | A2 | 4/2006 |
| WO | WO-2006097527 | A1 | 9/2006 |
| WO | WO-2006101940 | A2 | 9/2006 |
| WO | WO-2008032222 | A2 | 3/2008 |
| WO | WO-2008101693 | A2 | 8/2008 |
| WO | WO-2008101693 | A3 | 11/2008 |
| WO | WO-2009079790 | A1 | 7/2009 |
| WO | WO-2011097148 | A2 | 8/2011 |
| WO | WO-2011151685 | A1 | 12/2011 |
| WO | WO-2012064892 | A1 | 5/2012 |
| WO | WO-2013095275 | A1 | 6/2013 |
| WO | WO-2013182652 | A1 | 12/2013 |
| WO | WO-2014122184 | A1 | 8/2014 |
| WO | WO-2017182802 | A1 | 10/2017 |
| WO | WO-2018007864 | A1 | 1/2018 |
| WO | WO-2018029657 | A1 | 2/2018 |
| WO | WO-2018029658 | A1 * | 2/2018 | ............ A61K 31/13 |
| WO | WO-2018178670 | A1 | 10/2018 |
| WO | WO-2018229738 | A1 | 12/2018 |
| WO | WO-2019078915 | A1 | 4/2019 |
| WO | WO-2019079536 | A1 | 4/2019 |
| WO | WO-2019159110 | A1 | 8/2019 |
| WO | WO-2020052620 | A1 | 3/2020 |
| WO | WO-2020115715 | A1 | 6/2020 |
| WO | WO-2020178721 | A1 | 9/2020 |
| WO | WO-2020261230 | A1 | 12/2020 |
| WO | WO-2021048431 | A1 | 3/2021 |
| WO | WO-2021144720 | A1 | 7/2021 |
| WO | WO-2021234642 | A1 | 11/2021 |
| WO | WO-2022264037 | A1 | 12/2022 |
| WO | WO-2023196841 | A2 | 10/2023 |
| WO | WO-2025175092 | A1 | 8/2025 |
| WO | WO-2025264957 | A2 | 12/2025 |

OTHER PUBLICATIONS

Schneider Susanne A et al: "Do heterozygous mutations of Niemann-Pick type C predispose to late-onset neurodegeneration: a review of the literature", Journal of Neurology—Zeitschrift Fuer Neurologie, Springer Verlag, Berlin, DE, vol. 268, No. 6, 2019 , pp. 2055-2064, (Year: 2019).*

Abel, L.A., et al., "Saccades in adult Niemann-Pick disease type C reflect frontal, brainstem, and biochemical deficits," Neurology, 72(12): 1083-6, Wolters Kluwer, Netherlands (Mar. 2009).

Arbuthnott, K., et al., "Trail Making Test, Part B as a Measure of executive control: Validation Using a Set-Switching Paradigm," J Clin Exp Neuropsychol, 22(4): 518-528, Taylor and Francis Ltd., United Kingdom (Aug. 2000).

Battisti, C., et al., "Adult-Onset Niemann-Pick Type C Disease: A Clinical, Neuroimaging and Molecular Genetic Study," Movement Disorders, 18(11): 1405-9, Wiley, United States (Nov. 2003).

Beck, A.T., et al., "An Inventory for Measuring Depression," Archives of General Psychiatry, 4: 561-571, American Medical Association, United States (Jun. 1961).

Benussi, A., et al., "Phenotypic heterogeneity of Niemann-Pick disease type C in monozygotic twins," J Neurol, 262(3): 642-7, Springer Science+Business Media, United States (Mar. 2015).

Beyer, L., et al., "Clinical Routine FDG-PET Imaging of Suspected Progressive Supranuclear Palsy and Corticobasal Degeneration: A Gatekeeper for Subsequent Tau-PET Imaging?," Frontiers in Neurology, 9(483): 1-9, Frontiers Media, Switzerland (Jun. 2018).

Brandt, T., et al., "Plasticity of the Vestibular System: Central Compensation and Sensory Substitution for Vestibular Deficits," Brain Plasticity, Advances in Neurology, 73: 297-309, Ology Journals Kft., Hungary (1997).

Bremova, T., et al., "Acetyl-DL-leucine in Niemann-Pick type C: A case series," Neurology, 85(16): 1368-75, Wolters Kluwer, United States (Oct. 2015).

Bremova, T., et al., "Vestibular function in patients with Niemann-Pick type C disease," J Neurol, 263(11): 2260-2270, Springer Science+Business Media, United States (Nov. 2016).

Bremova-Ertl, T., et al., "Clinical, ocular motor, and imaging profile of Niemann-Pick type C heterozygosity," Neurology, 94(16): e1702-e1715, Wolters Kluwer, United States (Apr. 2020).

Bremova-Ertl, T., et al., "Oculomotor and Vestibular Findings in Gaucher Disease Type 3 and Their Correlation with Neurological Findings," Frontiers in Neurology, 8(711), 1-19, Frontiers Media, Switzerland (Jan. 2018).

Brendel, M., et al., "[$^{18}$F]-THK5351 Pet Correlates with Topology and Symptom Severity in Progressive Supranuclear Palsy," Frontiers in Aging Neuroscience, 9:440, 1-12, Frontiers Media, Switzerland (Jan. 2018).

Cheng, K.K., et al., "Highly Stabilized Curcumin Nanoparticles Tested in an In Vitro Blood-Brain Barrier Model and in Alzheimer's Disease Tg2576 Mice," The AAPS Journal, 15(2): 324-336, Springer Science+Business Media, United States (Apr. 2013).

Cupidi, C., et al., "Role of Niemann-Pick Type C Disease Mutations in Dementia," Journal of Alzheimer's Disease, 55: 1249-1259, IOS Press, Netherlands (2017).

(56) References Cited

OTHER PUBLICATIONS

Dieringer, N., "'Vestibular Compensation': Neural Plasticity and Its Relations to functional recovery after labyrinthine lesions in frogs and other vertebrates," *Progress in Neurobiology*, 46(2-3): 97-129, Elsevier, Netherlands (Jun. 1995).

Douglass, A., et al., "Behavioral Variant Frontotemporal Dementia Performance on a Range of Saccadic Tasks," *Journal of Alzheimer's Disease*, 65(1): 231-242, IOS Press, Netherlands (2018).

Ehrensperger, M.M., et al., "Early detection of Alzheimer's disease with a total score of the German Cerad," *J Int Neuropsychol Soc*, 16: 910-920, Cambridge University Press, United Kingdom (Sep. 2010).

Gray, A.J., et al., "Olfactory identification is impaired in clinic-based patients with vascular dementia and senile dementia of Alzheimer type," Int J Geriatr Psychiatry, 16(5): 513-7, Wiley, United States (May 2001).

Greer, W.L., et al., "Mutations in NPC1 Highlight a Conserved NPC1-Specific Cysteine-Rich Domain," *Am J Hum Genet*, 65(5): 1252-60, Elsevier, Netherlands (Nov. 1999).

Günther, L., et al., "N-Acetyl-L-Leucine Accelerates Vestibular Compensation after Unilateral Labyrinthectomy by Action in the Cerebellum and Thalamus," *PLoS One*, 10(3): e0120891, 18 pages, Plos One, United States (Mar. 2015).

Hanson, L.R., et al., "Intranasal delivery bypasses the blood-brain barrier to target therapeutic agents to the central nervous system and treat neurodegenerative disease," *BMC Neuroscience*, 9(Suppl 3): S5, 4 pages (Dec. 2008).

Harzer, K., et al., "Niemann-Pick Disease Type C: New Aspects in a Long Published Family—Partial Manifestations In Heterozygotes," *JIMD Reports*, 12: 25-29, Springer, Germany (May 2013).

Havla, J.B., et al., "Retinal axonal degeneration in Niemann-Pick type C disease," *J Neurol*, 267(7): 2070-82, Springer Science+Business Media, United States (Jul. 2020).

Heitz, C., et al., "Cognitive impairment profile in adult patients with Niemann pick type C disease," *Orphanet Journal of Rare Diseases*, 12:166, 10 pages, BioMed Central, United Kingdom (Oct. 2017).

Hoyles, K., et al., "Olfactory loss as a supporting feature in the diagnosis of Parkinson's disease: a pragmatic approach," *J Neurol*, 260(12): 2951-8, Springer Science+Business Media, United States (Dec. 2013).

Huang, J.Y., et al., "Neuroimaging Findings in a Brain With Niemann-Pick Type C Disease," *J Formos Med Assoc*, 110(8): 537-42, Excerpta Medica Asia Ltd., China (Aug. 2011).

Hummel, T., et al., "'Sniffin' Sticks': Olfactory Performance Assessed by the Combined Testing of Odor Identification, Odor Discrimination and Olfactory Threshold," *Chem Senses*, 22: 39-52, Oxford University Press, United Kingdom (Feb. 1997).

International Search Report and Written Opinion for International Application No. PCT/IB2021/050236, European Patent Office, Netherlands, mailed on Apr. 12, 2021, 12 pages.

Johnen, A., et al., "Distinguishing neurocognitive deficits in adult patients with NP-C from early onset Alzheimer's dementia," *Orphanet Journal of Rare Diseases*, 13(1): 91, 10 pages, BioMed Central, United Kingdom (Jun. 2018).

Josephs, K.A., et al., "Heterozygous Niemann-Pick disease type C presenting with tremor," *Neurology*, 63: 2189-90, Wolters Kluwer, Netherlands (Dec. 2004).

Kabanov, A.V., et al., "New Technologies for Drug Delivery across the Blood Brain Barrier," *Curr Pharm Des.*, 10(12): 1355-1363, Bentham Science Publishers, United Arab Emirates (2004).

Kluenemann, H.H., et al., "Parkinsonism Syndrome in Heterozygotes for Niemann Pick C1," *Journal of the Neurological Sciences*, 335(0): 219-220, Elsevier, Netherlands (Dec. 2013).

Kresojević, N., et al., "Mutations in Niemann Pick type C gene are risk factor for Alzheimer's disease," *Medical Hypotheses*, 83: 559-62, Elsevier, Netherlands (Nov. 2014).

Kumar, A., et al., "Niemann-Pick Disease Type C: Unique 2-Deoxy-2[$^{18}$F] Fluoro-D-Glucose PET Abnormality," *Pediatric Neurology*, 44(1): 57-60, Elsevier, Netherlands (Jan. 2011).

Lähde, A., et al., "Production of L-Leucine Nanoparticles under Various Conditions Using an Aerosol Flow Reactor Method," *Journal of Nanomaterials*, 2008: 680897, 9 pages, Hindawi, United Kingdom (May 2008).

Luppa, M., et al., "Age-related predictors of institutionalization: results of the German study on ageing, cognition and dementia in primary care patients (AgeCoDe)," *Soc Psychiatry Psychiatr Epidemiol*, 47(2): 263-70, Springer Science+Business Media, United States (Feb. 2012).

Olichney, J.M., et al., "Anosmia is very common in the Lewy body variant of Alzheimer's disease," *J Neurol Neurosurg Psychiatry*, 76(10): 1342-7, BMJ Group, United Kingdom (Oct. 2005).

Orasji, S.S.S., et al., "Olfactory dysfunction in behavioral variant frontotemporal dementia," *Clinical Neurology and Neurosurgery*, 141: 106-10, Elsevier, Netherlands (Feb. 2016).

Patel, M.M., et al., "Crossing the Blood-Brain Barrier: Recent Advances in Drug Delivery to the Brain," *CNS Drugs*, 31: 109-133, Springer Nature, Germany (Feb. 2017).

Patterson, M.C., et al., "Disease and patient characteristics in NP-C patients: findings from an international disease registry," *Orphanet Journal of Rare Diseases*, 8:12, 10 pages, BioMed Central, United Kingdom (Jan. 2013).

Patterson, M.C., et al., "Long-term Miglustat Therapy in Children With Niemann-Pick Disease Type C," *Journal of Child Neurology*, 25(3): 300-5, Sage Publications, United States (Mar. 2010).

Patterson, M.C., et al., "Recommendations for the detection and diagnosis of Niemann-Pick disease type C: An update," *Neurology: Clinical Practice*, 7: 499-511, Lippincott Williams and Wilkins, United States (Dec. 2017).

Patterson, M.C., et al., "Recommendations for the diagnosis and management of Niemann-Pick disease type C: An update," *Molecular Genetics and Metabolism*, 106(3): 330-44, Academic Press, United States (Jul. 2012).

Postuma, R.B., et al., "Advances in markers of prodromal Parkinson disease," *Nature Reviews Neurology*, 12(11): 622-634, Springer Nature, Germany (Oct. 2016).

Pretegiani, E., et al., "Eye Movements in Parkinson's Disease and Inherited Parkinsonian Syndromes," *Frontiers in Neurology*, 8: 592, 7 pages, Frontiers Media, Switzerland (Nov. 2017).

Probert, F., et al., "NMR analysis reveals significant differences in the plasma metabolic profiles of Niemann Pick C1 patients, heterozygous carriers, and healthy controls," Scientific Reports, 7: 6320, 12 pages, Springer, Netherlands (Jul. 2017).

Reunert, J., et al., "Niemann-Pick Type C-2 Disease: Identification by Analysis of Plasma Cholestane-3beta,5alpha,6beta-Triol and Further Insight into the Clinical Phenotype," *JIMD Reports*, 23: 17-26, Wiley, United States (Mar. 2015).

Royall, D.R., et al., "CLOX: an executive clock drawing task," *J Neurol Neurosurg Psychiatry*, 64(5): 588-94, BMJ Group, United Kingdom (May 1998).

Sánchez-Cubillo, I., et al., "Construct validity of the Trail Making Test: Role of task-switching, working memory, inhibition/interference control, and visuomotor abilities," *Journal of the International Neuropsychological Society*, 15(3): 438-50, Cambridge University Press, United Kingdom (May 2009).

Scaglione, C., et al., "REM sleep behaviour disorder in Parkinson's disease: a questionnaire-based study," *Neurol Sci*, 25(6): 316-21, Elsevier, Netherlands (Feb. 2005).

Schneider, E., et al., EyeSeeCam: An Eye Movement-Driven Head Camera for the Examination of Natural Visual Exploration, *Basic and Clinical Aspects of Vertigo and Dizziness: Annals of the New York Academy of Sciences*, 1164: 461-7, New York Academy of Sciences, United States (May 2009).

Schneider, S., "Do heterozygous mutations of Niemann-Pick type C predispose to late-onset neurodegeneration: a review of the literature," *Journal of Neurology*, 268(6): 2055-2064, Springer Science+Business Media, Germany (Jun. 2021).

Sévin, M., et al., "The adult form of Niemann- Pick disease type C," *Brain*, 130: 120-33, Oxford University Press, United Kingdom (Jan. 2007).

Sidransky, E., et al., "Multicenter Analysis of Glucocerebrosidase Mutations in Parkinson's Disease," *N Engl J Med*, 361(17): 1651-1661, Massachusetts Medical Society, United States (Oct. 2009).

(56)         References Cited

OTHER PUBLICATIONS

Stiasny-Kolster, K., et al., "The REM Sleep Behavior Disorder Screening Questionnaire—A New Diagnostic Instrument," *Movement Disorders,* 22: 2386-2393, Wiley, United States (Dec. 2007).

Written Opinion of International Preliminary Examining Authority of International Application No. PCT/IB2021/050236, European Patent Office, Netherlands, mailed on Dec. 17, 2021, 7 pages.

Yu, W., et al., "Neurodegeneration in Heterozygous Niemann-Pick type C1 (NPC1) Mouse: Implication of Heterozygous NPC1 Mutations Being a Risk for Tauopathy," *J Biol Chem,* 280(29): 27296-302, American Society for Biochemistry and Molecular Biology, United States (Jul. 2005).

Zech, M., et al., "Niemann-Pick C Disease Gene Mutations and Age-Related Neurodegenerative Disorders," *PLoS One,* 8(12): e82879, 8 pages, PLoS One, United States (Dec. 2013).

Barclay, L.L., et al., "The String Test: an Early Behavioral Change in Thiamine Deficiency," Pharmacology, Biochemistry, and Behavior 14(2):153-157, Elsevier, United States (Feb. 1981).

Boland, B., et al., "Macroautophagy is Not Directly Involved in the Metabolism of Amyloid Precursor Protein," The Journal of Biological Chemistry 285(48):37415-37426, American Society for Biochemistry and Molecular Biology, United States (Nov. 2010).

Bremova-Ertl, A., et al., "EPR1131 Acetyl-Leucine Slows Disease Progression in Lysosomal Storage Disorders," European Journal of Neurology 27(1):181, Wiley-Blackwell, United Kingdom (May 2020).

Champion, H., et al., "Dietary Modifications in Patients Receiving Miglustat," Journal of Inherited Metabolic Disease 33 (Suppl 3):S379-83, Wiley, United States (Dec. 2010).

Chida, J., et al., "An Efficient Extraction Method for Quantitation of Adenosine Triphosphate in Mammalian Tissues and Cells," Analytica Chimica Acta 727:8-12, Elsevier, Netherlands (May 2012).

Cortina-Borja, M., et al., "Annual Severity Increment Score as a Tool for Stratifying Patients with Niemann-Pick disease type C and for Recruitment to Clinical Trials," Orphanet Journal of Rare Diseases 13(1):143, BioMed Central, United Kingdom (Aug. 2018).

Hammond, N., et al., "The Complexity of a Monogenic Neurodegenerative Disease: More Than Two Decades of Therapeutic Driven Research Into Niemann-pick Type C Disease," Biochimica et Biophysica Acta-Molecular and Cell Biology of Lipids 1864(8):1109-1123, Elsevier, Netherlands (Aug. 2019).

Harris, R.A., et al., "Overview of the Molecular and Biochemical Basis of Branched-chain Amino Acid Catabolism" The Journal of Nutrition 135(6 Suppl):1527S-1530S, Elsevier, United States (Jun. 2005).

Harris, R.A., et al., "Physiological Covalent Regulation of Rat Liver Branched-chain Alpha-ketoacid Dehydrogenase," Archives of Biochemistry and Biophysics 243(2):542-555, Academic Press, United States (Dec. 1985).

Héron, B., et al., "Miglustat therapy in the French cohort of paediatric patients with Niemann-Pick disease type C," Orphanet Journal of Rare Diseases 7:36, pp. 1-14, BioMed Central, United Kingdom (Jun. 2012).

International Search Report and Written Opinion for International Application No. PCT/IB2020/056096, European Patent Office, Netherlands, mailed on Sep. 29, 2020, 11 pages.

Jeyakumar, M., et al., "Delayed Symptom Onset and Increased Life Expectancy in Sandhoff Disease Mice Treated With N-butyldeoxynojirimycin," Proceedings of the National Academy of Sciences of the United States of America 96(11):6388-6393, National Academy of Sciences, United States (May 1999).

Jha, M.K., et al., "Pyruvate Dehydrogenase Kinases in the Nervous System: Their Principal Functions in Neuronal-glial Metabolic Interaction and Neuro-metabolic Disorders," Current Neuropharmacology 10(4):393-403, Bentham Science Publishers, United Arab Emirates (Dec. 2012).

Kato, M., et al., "Structural Basis for Inactivation of the Human Pyruvate Dehydrogenase Complex by Phosphorylation: Role of Disordered Phosphorylation Loops," Structure 16(12):1849-1859, Cell Press, United States (Dec. 2008).

Kennedy, B.E., et al., "Pre-symptomatic Activation of Antioxidant Responses and Alterations in Glucose and Pyruvate Metabolism in Niemann-pick Type C1-deficient Murine Brain," PloS One 8(12):e82685, pp. 1-18, Public Library of Science, United States (Dec. 2013).

Kennedy, B.E., et al., "Presymptomatic Alterations in Amino Acid Metabolism and DNA Methylation in the Cerebellum of a Murine Model of Niemann-pick Type C Disease," The American Journal of Pathology 186(6):1582-1597, Elsevier, United States (Jun. 2016).

Kimball,S.R., et al., "Leucine Regulates Translation of Specific mRNAs in L6 Myoblasts through mTOR-mediated Changes in Availability of eIF4E and Phosphorylation of Ribosomal Protein S6," The Journal of Biological Chemistry 274(17):11647-11652, American Society for Biochemistry and Molecular Biology, United States (Apr. 1999).

Kirkegaard, T., et al., "Heat Shock Protein-based Therapy as a Potential Candidate for Treating the Sphingolipidoses," Science Translational Medicine 8(355):355ra118, American Association for the Advancement of Science, United States (Sep. 2016).

Klionsky, D.J., and Emr, S.D., "Autophagy as a Regulated Pathway of Cellular Degradation," Science 290(5497):1717-1721, American Association for the Advancement of Science, United States (Dec. 2000).

Liang, H., and Ward, W.F., "PGC-1alpha: A Key Regulator of Energy Metabolism," Advances in Physiology Education 30(4):145-151, American Physiological Society, United States (Dec. 2006).

Lloyd-Evans, E., and Platt, F.M., "Lipids on Trial: the Search for the Offending Metabolite in Niemann-Pick type C Disease," Traffic 11(4):419-428, John Wiley & Sons, United Kingdom (Apr. 2010).

Murphy, M.P., and Hartley, R.C., "Mitochondria as a Therapeutic Target for Common Pathologies," Nature Reviews Drug Discovery 17(12):865-886, Nature Pub. Group, United Kingdom (Dec. 2018).

Nagamori, S., et al., "Structure-activity Relations of Leucine Derivatives Reveal Critical Moieties for Cellular Uptake and Activation of mTORC1-mediated Signaling," Amino Acids 48(4):1045-1058, Springer-Verlag, Austria (Apr. 2016).

Neuzil, E., et al., "N-acetyl-DL-leucine, a Symptomatic Drug for Vertigo," Bulletin-societe De Pharmacie De Bordeaux 141(1-4):15-38, La Société, France (2002).

Neville, D.C., et al., "Analysis of Fluorescently Labeled Glycosphingolipid-derived Oligosaccharides Following Ceramide Glycanase Digestion and Anthranilic Acid Labeling," Analytical Biochemistry 331(2):275-282, Academic Press, United States (Aug. 2004).

Pankiv, S., et al., "P62/SQSTM1 Binds Directly to Atg8/LC3 to Facilitate Degradation of Ubiquitinated Protein Aggregates by Autophagy," The Journal of Biological Chemistry 282(33):24131-24145, American Society for Biochemistry and Molecular Biology, United States (Aug. 2007).

Patterson, M.C., et al., "Miglustat for treatment of Niemann-Pick C disease: a Randomised Controlled Study," The Lancet. Neurology 6(9):765-772, Lancet Pub. Group, United Kingdom (Sep. 2007).

Pentchev, P.G., et al., "A Lysosomal Storage Disorder in Mice Characterized by a Dual Deficiency of Sphingomyelinase and Glucocerebrosidase," Biochimica Et Biophysica Acta 619(3):669-679, Elsevier Pub. Co, Netherlands (Sep. 1980).

Pineda, M., et al., "Miglustat in Patients with Niemann-Pick Disease Type C (NP-C): a Multicenter Observational Retrospective Cohort Study," Molecular Genetics and Metabolism 98(3):243-249, Academic Press, United States (Nov. 2009).

Platt, F., and Strupp, M., "An Anecdotal Report by an Oxford Basic Neuroscientist: Effects of Acetyl-DL-leucine on Cognitive Function and Mobility in the Elderly," Journal of Neurology 263(6):1239-1240, Springer-Verlag, Germany (Jun. 2016).

Platt, F.M., "Emptying the Stores: Lysosomal Diseases and Therapeutic Strategies," Nature Reviews Drug Discovery 17(2):133-150, Nature Pub. Group, United Kingdom (Feb. 2018).

Platt, F.M., et al., "The Cell Biology of Disease: Lysosomal Storage Disorders: the Cellular Impact of Lysosomal Dysfunction," The Journal of Cell Biology 199(5):723-734, Rockefeller University Press, United States (Nov. 2012).

(56)　　　　　References Cited

OTHER PUBLICATIONS

Pliss, L., et al., "Cerebral Developmental Abnormalities in a Mouse With Systemic Pyruvate Dehydrogenase Deficiency," PloS One 8(6):e67473, Public Library of Science, United States (Jun. 2013).

Priestman, D.A., et al., "N-butyldeoxynojirimycin Causes Weight Loss as a Result of Appetite Suppression in Lean and Obese Mice," Diabetes, Obesity and Metabolism 10(2):159-166, Wiley-Blackwell, United Kingdom (Feb. 2008).

Ruiz-Rodado, V., et al., "1h NMR-linked Metabolomics Analysis of Liver From a Mouse Model of NP-C1 Disease," Journal of Proteome Research 15(10):3511-3527, American Chemical Society, United States (Oct. 2016).

Sandhoff, L., and Harzer, K., "Gangliosides and Gangliosidoses: Principles of Molecular and Metabolic Pathogenesis," The Journal of Neuroscience 33(25):10195-10208, Society for Neuroscience, United States (Jun. 2013).

Sango, K., et al., "Mouse Models of Tay-sachs and Sandhoff Diseases Differ in Neurologic Phenotype and Ganglioside Metabolism," Nature Genetics 11(2):170-176, Nature Pub. Co, United States (Oct. 1995).

Son, S.M., et al., "Leucine Signals to mTORC1 Via Its Metabolite Acetyl-Coenzyme A," Cell Metabolism 29(1):192-201.e7, Cell Press, United States (Jnauary 2019).

Stein, L.R., and Imai, S-I., "The Dynamic Regulation of NAD Metabolism in Mitochondria," Trends in Endocrinology and Metabolism 23(9):420-428, Elsevier Science Pub. Co, United States (Sep. 2012).

Strupp, M., et al., "Effects of Acetyl-dl-leucine in Patients with Cerebellar Ataxia: A Case Series," Journal of neurology, 260(10):2556-2561, Springer-Verlag, Germany (2013).

Te Vruchte, D., et al., "Relative Acidic Compartment Volume as a Lysosomal Storage Disorder-associated Biomarker," The Journal of Clinical Investigation 124(3):1320-1328, American Society for Clinical Investigation, United States (Mar. 2014).

Tighilet, B., et al., "Comparative Analysis of Pharmacological Treatments With N-acetyl-dl-leucine (Tanganil) and Its Two Isomers (N-acetyl-L-leucine and N-acetyl-D-leucine) on Vestibular Compensation: Behavioral Investigation in the Cat," European Journal of Pharmacology 769:342-349, Elsevier Science, Netherlands (Dec. 2015).

Vibert, N. and Vidal, P.P., "In Vitro Effects of Acetyl-dl-leucine(Tanganil) on Central Vestibular Neurons and Vestibulo-ocular Networks of the Guinea-pig," The European Journal of Neuroscience 13(4):735-748, Wiley-Blackwell, France (Feb. 2001).

Williams, I.M., et al., "Improved Neuroprotection Using Miglustat, Curcumin and Ibuprofen as a Triple Combination Therapy in Niemann-pick Disease Type C1 Mice," Neurobiology of Disease 67:9-17, Academic Press, United States (Jul. 2014).

Yanagisawa, H., et al., "L-leucine and SPNS1 Coordinately Ameliorate Dysfunction of Autophagy in Mouse and Human Niemann-Pick type C disease," Scientific Reports 7(1):15944, Nature Publishing Group, United Kingdom (Nov. 2017).

Yanjanin, N.M., et al., "Linear Clinical Progression, Independent of Age of Onset, in Niemann-pick Disease, Type C," American Journal of Medical Genetics Neuropsychiatric Genetics 153B(1):132-140, Wiley-Blackwell, United States (Jan. 2010).

Yudkoff, M., "Brain Metabolism of Branched-chain Amino Acids," Glia 21(1):92-98, Wiley-Liss, United States (Sep. 1997).

Schniepp, R., et al., "Acetyl-DL-leucine improves gait variability in patients with cerebellar ataxia-a case series," Cerebellum Ataxias 3:8, BioMed Central, United Kingdom (Apr. 2016).

Wiederschain, G.Y., "The Metabolic and Molecular Bases of Inherited Disease," Biochemistry (Moscow) 67(5):611-612, Pleiades Publishing, Ltd., Russia (May 2002).

Abdulkhaleq, L.A., et al., "The Crucial roles of Inflammatory Mediators in Inflammation: A Review," Veterinary World 11(5):627-635, Veterinary World, India (May 2018).

Aerts, J.M.F.G., et al., "Biomarkers in the Diagnosis of Lysosomal Storage Disorders: Proteins, Lipids, and Inhibodies," Journal of Inherited Metabolic Disease 34(3):605-619, Wiley, United States (Jun. 2011).

Akita, H., et al., "Creation of a Thermostable NADP?-dependent D-amino Acid Dehydrogenase from Ureibacillus Thermosphaericus Strain A1 Meso-diaminopimelate Dehydrogenase by Site-directed Mutagenesis," Biotechnology Letters 34(9):1693-1699, Kluwer Academic Publishers, Netherlands (Sep. 2012).

Akita, H., et al., "Spectrophotometric Assay of D-isoleucine Using an Artificially Created D-amino Acid Dehydrogenase," Biotechnology Letters 36(11):2245-2248, Kluwer Academic Publishers, Netherlands (Nov. 2014).

Almanov, G.A., et al., "Structure of Free Radicals in Irradiated Acetyl-L-leucine Single Crystals at 77 K," Journal of Structural Chemistry 29(2):216-220, Plenum Publishing Corporation, United States (Mar.-Apr. 1988).

Almanov, G.A., et al., "Structure of Free Radicals in Irradiated Acetyl-L-leucine Single Crystals," Khimia Vysokikh Energii 20(5):430-435, Nauka, Union of Soviet Socialist Republics (Sep.-Oct. 1986).

Amor, S., et al., "Inflammation in Neurodegenerative Diseases—an Update," Immunology 142(2):151-166, Blackwell Scientific Publications, United Kingdom (Jun. 2014).

Angelini, C., et al., "Major Intra-familial Phenotypic Heterogeneity and Incomplete Penetrance Due to a CACNAIA Pathogenic Variant," European Journal of Medical Genetics 62(6):103530, Elsevier, Netherlands (Jun. 2019).

Antonenko, L.M., "The Second Congress International Academy of Dizziness," Neurological Journal 20(4):51-53, Federal State Autonomous Institution "National Medical Research Center for Children's Health" of the Ministry of Health of the Russian Federation, Russia (Dec. 2015).

Ashizawa, T., and Xia, G., "Ataxia," Continuum (Minneap Minn) 22(4 Movement Disorders):1208-1226, Wolters Kluwer, Netherlands (Aug. 2016).

August, R.A., et al., "Stereospecific Synthesis of (2S,4R)-[5,5,5-2H3]-leucine," Tetrahedron Letters 33:4617-4620, Elsevier, Netherlands (Aug. 1992).

Baci, D., et al., "Acetyl-L-Carnitine Downregulates Invasion (CXCR4/CXCL12, MMP-9) and Angiogenesis (VEGF, CXCL8) Pathways in Prostate Cancer Cells: Rationale for Prevention and Interception Strategies," Journal of Experimental & Clinical Cancer Research 38(1):464, pp. 1-17, BioMed Central, United Kingdom (Nov. 2019).

Beaudin, M., et al., "Systematic Review of Autosomal Recessive Ataxias and Proposal for a Classification," Cerebellum and Ataxias 4:3, BioMed Central, United Kingdom (Feb. 2017).

Becker-Bense, S., et al., "P37. Effects of Acetyl-dl-leucine on the Cerebral Activation Pattern in Cerebellar Ataxia (FDG-PET Study)," Clinical Neurophysiology 126(8):e115, Elsevier, (Aug. 2015), 1 page.

Belarbi, K., et al., "TNF-a Protein Synthesis Inhibitor Restores Neuronal Function and Reverses Cognitive Deficits Induced by Chronic Neuroinflammation," Journal of Neuroinflammation 9:23, pp. 1-13, BioMed Central, United Kingdom (Jan. 2012).

Belikov, V.G., Pharmaceutical Chemistry: Manual, 4th edition, pp. 27-29, MEDpress-inform, Moscow, Russia (2007).

Bingham, A.L., et al., "Over one Hundred Solvates of Sulfathiazole," Chemical Communications, pp. 603-604, The Royal Society of Chemistry, United Kingdom (2001).

Bird, T.D., "Hereditary Ataxia Overview," in GeneReviews® (Internet), Adam, M.P., Ardinger H.H,, Pagon, R.A., et al., eds., pp. 1993-2020, University of Washington, Seattle, United States, Oct. 1998 (Updated Jul. 2019).

Caira, M.R., et al., "Preparation and Crystal Characterization of a Polymorph, a Monohydrate, and an Ethyl Acetate Solvate of the Antifungal Fluconazole," Journal of Pharmaceutical Sciences 93(3):601-611, Elsevier, United States (Mar. 2004).

Cardellicchio, C., et al., "Synthesis of a-amino Acid Derivatives by Copper(I)-catalyzed Conjugate Addition of Grignard Reagents to Methyl Acetamidoacrylate," Tetrahedron Letters 26(36):4387-4390, Pergamon Press Ltd, United Kingdom (May 1985).

(56) References Cited

OTHER PUBLICATIONS

Chakrabarti, S., et al., "Upregulation of Suppressor of Cytokine Signaling 3 in Microglia by Cinnamic Acid," Current Alzheimer Research 15(10):894-904, Bentham Science Publishers, United Arab Emirates (2018).

Chatterjee, B., et al., "Selective a-Deuteration of Amines and Amino Acids Using D$_2$O," Organic Letters 18(22):5892-5895, American Chemical Society, United States (Nov. 2016).

Chen, W-W., et al., "Role of Neuroinflammation in Neurodegenerative Diseases (Review)," Molecular Medicine Reports 13(4):3391-3396, D. A. Spandidos, Greece (Apr. 2016).

Cherry, J.D., et al., "Neuroinflammation and M2 Microglia: the Good, the Bad, and the Inflamed," Journal of Neuroinflammation 11:98, pp. 1-15, BioMed Central, United Kingdom (Jun. 2014).

Choi, K.D., and Choi, J.H., "Episodic Ataxias: Clinical and Genetic Features," Journal of Movement Disorders 9(3):129-135, Korean Movement Disorder Society, Korea (Sep. 2016).

Coccia, M., et al., "IL-1β Mediates Chronic Intestinal Inflammation by Promoting the Accumulation of IL-17A Secreting Innate Lymphoid Cells and CD4(+) Th17 Cells," The Journal of Experimental Medicine 209(9):1595-609, Rockefeller University Press, United States (Aug. 2012).

Davies, S.G., et al., "Asymmetric Conjugate Reductions with Samarium Diiodide: Asymmetric Synthesis of (2S,3R)- and (2S,3S)-[2-2H,3-2H]-leucine-(S)-phenylalanine Dipeptides and (2S,3R)-[2-(2)H,3-2H]-phenylalanine Methyl Ester," Organic Biomolecular Chemistry 3(8):1435-1447, Royal Society of Chemistry, United Kingdom (Apr. 2005).

Debray, F-G., et al., "Disorders of Mitochondrial Function," Current Opinion in Pediatrics 20(4):471-482, Lippincott Williams and Wilkins, United States (Aug. 2008).

Denier, C., et al., "High prevalence of CACNAIA Truncations and Broader Clinical Spectrum in Episodic Ataxia Type 2," Neurology 52(9):1816-1821, Wolters Kluwer, Netherlands (Jun. 1999).

Disabato, D.J., et al., "Neuroinflammation: the Devil Is in the Details," Journal of Neurochemistry 139 Suppl 2(Suppl 2):136-153, Wiley on behalf of the International Society for Neurochemistry, United Kingdom (Oct. 2016).

Dyck, L.E., et al., "Effects of Deuterium Substitution on the Catabolism of Beta-Phenylethylamine: an in Vivo Study," Journal of Neurochemistry 46(2):399-404, Wiley, United Kingdom (Feb. 1986).

Dyson, G., et al., "The Mechanism of Action of Medicinal Substances," in Chemistry of Synthetic Drugs, pp. 12-19, Mir Publishers, Moscow, Union of Soviet Socialist Republics (1964).

English language translation of Office Action for Russian Patent Application No. 2021119633, dated May 22, 2023, Federal Service for Intellectual Property, Moscow, Russia, 6 pages.

Fang, J., et al., "Dose Staggering as a Strategy to Reduce Drug--drug Interactions Due to Reversible Enzyme Inhibition Between Orally Administered Drugs With High First Pass Effect: A Computer Simulation Study," Biopharmaceutics & Drug Disposition 21(7):249-259, Wiley, United Kingdom (Oct. 2000).

Feil, K., et al., "Update on the Pharmacotherapy of Cerebellar Ataxia and Nystagmus," Cerebellum 15(1):38-42, Springer Nature, Germany (Feb. 2016).

Final Office Action for U.S. Appl. No. 17/247,757, mailed on May 5, 2023, 17 pages.

Fletcher, M.D., et al., "Three Approaches to the Synthesis of L-leucine Selectively Labelled with Carbon-13 or Deuterium in Either Diastereotopic Methyl Group," Journal of the Chemical Society 43-52, 10 Pages, Royal Society of Chemistry, United Kingdom (Jan. 2000).

Frank-Cannon, T.C., et al., "Does Neuroinflammation Fan the Flame in Neurodegenerative Diseases?" Molecular Neurodegeneration 4:47, pp. 1-13, BioMed Central, United Kingdom (Nov. 2009).

Frankola, K.A., et al., "Targeting TNF-a to Elucidate and Ameliorate Neuroinflammation in Neurodegenerative Diseases," CNS & Neurological Disorders Drug Targets 10(3):391-403, Bentham Science Publishers, United Arab Emirates (May 2011), 25 pages.

Gandini, J., et al., "The Neurological Update: Therapies for Cerebellar Ataxias in 2020," Journal of Neurology 267(4):1211-1220, Springer Nature, Germany (Apr. 2020).

Giese, A.K., et al., "A Novel, Highly Sensitive and Specific Biomarker for Niemann-pick Type C1 Disease," Orphanet Journal of Rare Diseases 10:78, 8 Pages, BioMed Central, United Kingdom (Jun. 2015).

Ginger, M.L., et al., "The Biosynthetic Incorporation of the Intact Leucine Skeleton Into Sterol by the Trypanosomatid Leishmania Mexicana," The Journal of Biological Chemistry 276(15):11674-11682, Elsevier Inc, United States (Apr. 2001).

Griggs, R.C., et al., "Hereditary Paroxysmal Ataxia: Response to Acetazolamide," Neurology 28(12):1259-1264, Wolters Kluwer, Netherlands (Dec. 1978).

Gu, Y., et al., "Role of TNF in Mast Cell Neuroinflammation and Pain," Journal of Biological Regulators and Homeostatic Agents 29(4):787-791, Biolife, Italy (Oct.-Dec. 2015).

Guterman, E.L., et al., "Pearls & Oy-sters: Episodic Ataxia Type 2: Case Report and Review of the Literature," Neurology 86(23):e239-e241, Wolters Kluwer, Netherlands (Jun. 2016).

Habbas, S., et al., "Neuroinflammatory TNFa Impairs Memory via Astrocyte Signaling," Cell 163(7):1730-1741, Cell Press, United States (Dec. 2015).

Hill, R.K., et al., "Synthesis of (2S,4S)- and (2S,4R)-[5,5,5-$^2$H$_3$] Leucine from (R)-pulegone[1]," Canadian Journal of Chemistry 72(1):110-113 NRC Research Press, Canada (Jan. 1994).

Homer, R.J., et al., "The Use of Cystathionine Gamma-synthase in the Production of Alpha and Chiral Beta Deuterated Amino Acids," Analytical Biochemistry 215(2):211-215, Elsevier, United States (Dec. 1993).

Hong, H., et al., "Pathophysiological Role of Neuroinflammation in Neurodegenerative Diseases and Psychiatric Disorders," International Neurourology Journal 20(Suppl 1):S2-S7, Korean Continence Society, Korea (May 2016).

Huang, H., et al., "Effects of Acetylleucine on the Recovery of Motor Balance and Discharge Activity of Neurons in the Medial Vestibular Nucleus in Rats after Labyrinthine Injury," Collection of Abstracts of the 21st National Congress and Academic Conference of the Chinese Physiological Society, Abstract 243, p. 66, Chinese Physiological Society, China (Oct. 2002).

Ilg, W., "Consensus Paper: Management of Degenerative Cerebellar Disorders," Cerebellum 13(2):248-268, Springer Nature, Germany (Apr. 2014).

Imbrici, P., et al., "Late-onset Episodic Ataxia Type 2 Due to an In-frame Insertion in CACNAIA," Neurology 65(6):944-946, Wolters Kluwer, Netherlands (Sep. 2005).

Inacio, A.R., et al., "Endogenous IFN-β Signaling Exerts Anti-inflammatory Actions in Experimentally Induced Focal Cerebral Ischemia," Journal of Neuroinflammation 12:211, pp. 1-18, BioMed Central, United Kingdom (Nov. 2015).

International Search Report and Written Opinion for Application No. PCT/IB2019/060525, mailed on Feb. 3, 2020, 14 pages.

International Search Report and Written Opinion for Application No. PCT/IB2021/054399, mailed on Aug. 18, 2021, 9 pages.

International Search Report and Written Opinion of International Application No. PCT/IB2020/051767, mailed on Jul. 30, 2020, 19 pages.

Isaacs, D.A., et al., "Case report of novel CACNAIA Gene Mutation Causing Episodic Ataxia Type 2," SAGE Open Medical Case Reports 5:1-3, SAGE Publications, United States (May 2017).

Jen, J., et al., "Clinical Spectrum of Episodic Ataxia Type 2," Neurology 62(1):17-22, Wolters Kluwer, Netherlands (Jan. 2004).

Jen, J.C., and Wan, J., "Episodic Ataxias," Handbook of Clinical Neurology 155:205-215, Elsevier, Netherlands (2018).

Jen, J.C., et al., "Primary Episodic Ataxias: Diagnosis, Pathogenesis and Treatment," Brain 130(Pt 10):2484-2493, Oxford University Press, United Kingdom (Oct. 2007).

Jeyakumar, M., et al., "Central Nervous System Inflammation is a Hallmark of Pathogenesis in Mouse Models of GM1 and GM2 Gangliosidosis," Brain 126(Pt 4):974-987, Oxford University Press, United Kingdom (Apr. 2003).

(56)        References Cited

OTHER PUBLICATIONS

Kalla, R., and Strupp, M., "Aminopyridines and Acetyl-DL-leucine: New Therapies in Cerebellar Disorders," Current Neuropharmacology 17(1):7-13, Bentham Science Publishers, United Arab Emirates (Jan. 2019).

Karve, I.P., et al., "Ablation of Type-1 IFN Signaling in Hematopoietic Cells Confers Protection Following Traumatic Brain Injury," eNeuro 3(1):Eneuro.0128-15, Society for Neuroscience, United States (Feb. 2016).

Kelly, N.M., et al., "Chemo-enzymatic Synthesis of Isotopically Labelled L-valine, L-isoleucine and Allo-isoleucine," Tetrahedron Letters 37(9):1517-1520, Elsevier, United Kingdom (Feb. 1996).

Kelly, N.M., et al., "Methods for the Synthesis of L-Leucine Selectively Labelled with Carbon-13 or Deuterium in either Diastereotopic Methyl Group," Tetrahedron Letters 36:8315-8318, Elsevier, United Kingdom (Nov. 1995).

Kelly, N.M., et al., "Syntheses of Amino Acids Incorporating Stable Isotopes," Nat Prod Rep 14:205-219, Royal Society of Chemistry, United Kingdom (Jan. 1997).

Khelimsky, A.M., et al., *Clinic Picture, Diagnosis and Treatment of Cranio-Brain Injuries*, pp. 22-24 (2003), 8 pages.

Kim, J.M., et al., "Episodic Ataxia Type 2 due to a Deletion Mutation in the CACNA1A Gene in a Korean Family," Journal of Clinical Neurology 2(4):268-271, Korean Neurological Association, Korea (Dec. 2006).

Kinney, C.R., and Adams, R., "Dideuteriovaline and Dideuterioleucine," Journal of the American Chemical Society 59(5):897-898, American Chemical Society, United States (May 1937).

Kipfer, S., and Strupp, M., "The Clinical Spectrum of Autosomal-Dominant Episodic Ataxias," Movement Disorder Clinical Practice 1(4):285-290, Wiley, United States (Jul. 2014).

Kummerer, K., "Pharmaceuticals in the Environment," Annual Review of Environment and Resources 35:57-75, Annual Reviews, United States (Aug. 2010).

Lappalainen, U., et al., "Interleukin-1beta Causes Pulmonary Inflammation, Emphysema, and Airway Remodeling in the Adult Murine Lung," American Journal of Respiratory Cell and Molecular Biology 32(4):311-318, American Thoracic Society, United States (Apr. 2005).

Lee, J.H., et al., "Anti-inflammatory and Anti-genotoxic Activity of Branched Chain Amino Acids (BCAA) in Lipopolysaccharide (LPS) Stimulated Raw 264.7 Macrophages," Food Science and Biotechnology 26(5):1371-1377, Korean Society of Food Science and Technology, Korea (Aug. 2017).

Liu, S.Q., et al., Leucine Alters Immunoglobulin a Secretion and Inflammatory Cytokine Expression Induced by Lipopolysaccharide via the Nuclear Factor-kb Pathway in Intestine of Chicken Embryos, Animal : an International Journal of Animal Bioscience 12(9):1903-1911, Elsevier, United Kingdom (Sep. 2018).

Lobato, J.B., et al., "Biomarkers in Lysosomal Storage Diseases," Diseases 4(4):40, 17 Pages, MDPI AG, Switzerland (Dec. 2016).

Maksemous, N., et al., "Next-generation Sequencing Identifies Novel CACNA1A Gene Mutations in Episodic Ataxia Type 2," Molecular Genetics and Genomic Medicine 4(2):211-222, Wiley, United States (Jan. 2016).

Mantuano, E., et al., "Identification of Novel and Recurrent CACNA1A Gene Mutations in Fifteen Patients with Episodic Ataxia Type 2," Journal of Neurological Sciences 291(1-2):30-36, Elsevier, Netherlands (Apr. 2010).

Miyanoiri, Y., et al., "Differential Isotope-labeling for Leu and Val Residues in a Protein by *E. coli* Cellular Expression Using Stereo-specifically Methyl Labeled Amino Acids," Journal of Biomolecular NMR 57(3):237-249, Springer, Netherlands (Nov. 2013).

Moss, G.P., "Basic Terminology of Stereochemistry," Pure and Applied Chemistry 68(12):2193-2222, IUPAC, United Kingdom (1996).

Nakajima, N., et al., "Enzymatic Conversion of Racemic Methionine to the L-enantiomer," Journal of the Chemical Society 13:947-948, Royal Society of Chemistry, United Kingdom (1990).

Niyazov, D.M., et al., "Primary Mitochondrial Disease and Secondary Mitochondrial Dysfunction: Importance of Distinction for Diagnosis and Treatment," Molecular Syndromology 7(3):122-137, S. Karger, Switzerland (Jul. 2016).

Non-Final Office Action for U.S. Appl. No. 17/247,757, mailed on Oct. 4, 2023, 16 pages.

Non-Final Office Action for U.S. Appl. No. 17/247,757, mailed on Oct. 6, 2022, 14 pages.

Notice of Allowance for U.S. Appl. No. 17/247,757, mailed on Apr. 10, 2024, 13 pages.

Oba, M., et al., "Stereoselective Deuterium-labelling of Diastereotopic Methyl and Methylene Protons of L-leucine," Tetrahedron Letters 39:1595-1598, Elsevier, Netherlands (Mar. 1998).

Oba, M., et al., "Synthesis of (13)C/D Doubly Labeled L-leucines: Probes for Conformational Analysis of the Leucine Side-chain," The Journal of Organic Chemistry 66(17):5919-5922, American Chemical Society, United States (Aug. 2001).

Oba, M., et al., "Synthesis of L-threo- and L-erythro-[1-$^{13}$C, 2,3-$^{2}$H$_2$] Amino Acids: Novel Probes for Conformational Analysis of Peptide Side Chains" Journal of the Chemical Society 12:1603-1609, Royal Society of Chemistry, United Kingdom (1995).

Ophoff, R.A., et al., "Familial Hemiplegic Migraine and Episodic Ataxia Type-2 Are Caused by Mutations in the Ca2+ Channel Gene CACNL1A4," Cell 87(3):543-552, Cell Press, United States (Nov. 1996).

Oxbridge Solutions Limited, "Acetylation of drugs," GPnotebook, published on Jan. 1, 2018, accessed at https://gpnotebook.com/pages/surgery/acetylation-of-drugs, accessed on Feb. 26, 2025, 2 Pages.

Pelz, J.O., et al., "Failure to Confirm Benefit of Acetyl-dl-leucine in Degenerative Cerebellar Ataxia: A Case Series," Journal of Neurology, 262(5):1373-1375, Springer-Verlag, Germany (2015).

Penkava, J., et al., "A Novel Pathogenic CACNA1A Variant Causing Episodic Ataxia Type 2 (EA2) Spectrum Phenotype in Four Family Members and a Novel Combined Therapy," Journal of Neurology 267(Suppl 1):181-184, Springer Nature, Germany (Dec. 2020).

PubChem, "Acetylleucine," CID 1995, accessed at https://pubchem.ncbi.nlm.nih.gov/compound/1995#section= 2D-Structure, 3 pages.

Ray, K.K., "Interleukin-1 Revisited: Further Insights Into Its Role in Atherosclerosis and as a Potential Therapeutic Target for Treatment," Journal of the American College of Cardiology 63(17):1735-1738, Elsevier Biomedical, United States (May 2014).

Ren, K., and Torres, R., "Role of Interleukin-1beta during Pain and Inflammation," Brain Research Reviews 60(1):57-64, Elsevier B.V., Netherlands (2009).

Riant, F., et al., "Ataxies Episodiques Genetiques [Hereditary Episodic Ataxia]," Revue Neurologique 167(5):401-407, Elsevier, Netherlands (May 2011).

Richards, S., et al., "Standards and Guidelines for the Interpretation of Sequence Variants: a Joint Consensus Recommendation of the American College of Medical Genetics and Genomics and the Association for Molecular Pathology," Genetics in Medicine 17(5):405-424, Elsevier, Netherlands (May 2015).

Rose, J.E., et al., "Stereospecific Synthesis of a-Deuteriated a-Amino Acids: Regiospecific Deuteriation of Chiral 3-Isopropyl-2,5-Dimethoxy-3,6-Dihydropyrazines," Journal of the Chemical Society 2:157-165, Royal Society of Chemistry, United Kingdom (1995).

Rozenbaum, H., "How to Evaluate the Risk-benefit Ratio of the Low-dose Hormone Replacement Therapy?" The Journal of Steroid Biochemistry and Molecular Biology 102(1-5):256-260, Pergamon, United Kingdom (Dec. 2006).

Sarkar, C., et al., "Impaired Autophagy Flux is Associated With Neuronal Cell Death After Traumatic Brain Injury," Autophagy 10(12):2208-2222, Taylor & Francis, United States (2014).

Sarkar, C., et al., "N-acetyl-L-leucine Treatment Attenuates Neuronal Cell Death and Suppresses Neuroinflammation After Traumatic Brain Injury in Mice," bioRxiv, pp. 1-20, accessed at https://www.biorxiv.org/content/10.1101/759894v1.full.pdf, accessed on Sep. 8, 2019.

Sarkar, C., et al., "PLA2G4A/cPLA2-Mediated Lysosomal Membrane Damage Leads to Inhibition of Autophagy and Neurodegenera-

(56)        References Cited

OTHER PUBLICATIONS tion After Brain Trauma," Autophagy 16(3):466-485, Taylor & Francis, United States (Mar. 2020).

Shah, S.A., et al., "Enantiomeric Conversion of Racemic Amino Acid Mixtures via an Oxidase-Aminotransferase Coupled System," Tetrahedron Letters 35:29-32, Elsevier, United Kingdom (Jan. 1994).

Shao, L., and Hewitt, M.C., "The Kinetic Isotope Effect in the Search for Deuterated Drugs," Drug News & Perspectives 23(6)398-404, Thomson Reuters, United States (Jul.-Aug. 2010).

Shibanuma, M., et al., "Inhibition by N-acetyl-L-cysteine of Interleukin-6 mRNA Induction and Activation of NF Kappa B by Tumor Necrosis Factor Alpha in a Mouse Fibroblastic Cell Line, Balb/3T3," FEBS Letters 353(1):62-66, John Wiley & Sons Ltd, United Kingdom (Oct. 1994).

Simonaro, C.M., "Lysosomes, Lysosomal Storage Diseases, and Inflammation," Journal of Inborn Errors of Metabolism & Screening 4:1-8, Latin American Society of Inborn Errors of Metabolism and Newborn Screening, Uruguay (2016).

Sintas, C., et al., "Mutation Spectrum in the CACNAIA Gene in 49 Patients with Episodic Ataxia," Scientific Reports 7(1):2514, Springer Nature, Germany (May 2017).

Strupp, M., et al., "A Randomized Trial of 4-Aminopyridine in Ea2 and Related Familial Episodic Ataxias," Neurology 77(3):269-275, Wolters Kluwer, United States (Jul. 2011).

Strupp, M., et al., "Fampridine and Acetazolamide for the Treatment of Episodic Ataxia Type 2 Eat2treat): a Randomised, Double-blind, Placebo-controlled, Three-period Crossover Trial (2331)," Neurology 94(15_supplement): Abstract 2331, Wolters Kluwer, United States (Apr. 2020).

Strupp, M., et al., "Treatment of Episodic Ataxia Type 2 with the Potassium Channel Blocker Aminopyridine," Neurology 62(9):1623-1625, Wolters Kluwer, United States (May 2004).

The Definition of "Disease Prevention", accessed from Free Dictionary Web, Retrieved from Internet URL: https://web.archive.org/web/20150910204016/https://medical-dictionary.thefreedictionary.com/Prevention+(medical), 2 Pages (Sep. 2018).

Timmins, G.S., "Deuterated Drugs: Where Are We Now?" Expert Opinion on Therapeutic Patents 24(10):1067-1075, Taylor & Francis, United Kingdom (Oct. 2014).

Tuttolomondo, A., et al., "Studies of Selective TNF Inhibitors in the Treatment of Brain Injury from Stroke and Trauma: a Review of the Evidence to Date," Drug Design, Development and Therapy 8:2221-2238, Dove Press Limited, New Zealand (Nov. 2014).

Upson, D.A., and Hruby, V.J., "A General Method for the Preparation of Alpha-labeled Amino Acids," The Journal of Organic Chemistry 42(13):2329-2330, American Chemical Society, United States (Jun. 1977).

Van Tonder, E.C., et al., "Preparation and Physicochemical Characterization of 5 Niclosamide Solvates and 1 Hemisolvate," AAPS PharmSciTech 5(1):E12, pp. 1-10, Springer, United States (Feb. 2004).

Xu, H., and Ren, D., "Lysosomal Physiology," Annual Review of Physiology 77:57-80, Annual Reviews, United States (2015).

Yamauchi, N., and Endoh, S., "IMproved Isotopic Deuterium Labeling at the Diastereotopic Methyl Group of Leucine: a Synthetic Route to (4S)- and (4R)-[5-$^2$H$_1$] Leucine," Bioscience, Biotechnology, and Biochemistry 70(1):276-278, Oxford University Press, United Kingdom (Jan. 2006).

Yuan, S.S., and Ajami, A.M., "Trideuteromethyl Labeled Leucine and Valine," Hua Xue - Chemistry 49(4):257-260, Zhonggguo Huaxuehui, Taiwan (Dec. 1991).

Zwergal A., et al., "Sequential [(18)F]FDG μPET Whole-brain Imaging of Central Vestibular Compensation: A Model of Deafferentation-induced Brain Plasticity," Brain Structure and Function, 221(1):159-170, Springer-Verlag, Germany (2016).

PCT Application No. PCT/US2025/015918, inventors Billington, I.M., et al., filed on Feb. 14, 2025, 58 pages (Not yet Published).

PCT Application No. PCT/US2025/034430, inventors Factor, M., et al., filed on Jun. 20, 2025, 106 pages (Not yet Published).

European Medicines Agency, "Zavesca," European Public Assessment Report—Product Information, accessed at ec.europa.eu/health/documents/community-register/2010/2010060278532/anx_78532_en.pdf, accessed on Apr. 16, 2025, 25 pages (Jun. 2010).

Patterson, M., et al., "Niemann-Pick Disease Type C," in GeneReviews® [Internet], Adam, M.P., et al., eds., 2 pages, University of Washington, Seattle, United States (Dec. 10, 2020).

Stiasny-Kolster, K., et al., "Diagnostic value of the REM sleep behavior disorder screening questionnaire in Parkinson's disease," Sleep Medicine 16(1):186-189, Elsevier, Netherlands (Jan. 2015).

Armstrong, C., "Aan/Ahs Update Recommendations for Migraine Prevention in Adults," American Family Physician 87(8):584-585, American Academy of General Practice, United States (2013).

Bartleson, J.D. and Cutrer F. M., "Migraine Update Diagnosis and Treatment," Minnesota Medicine 93(5):36-41, Minnesota Medical Assn, United States (May 2010).

Buchfuhrer, M.J., "Strategies for the Treatment of Restless Legs Syndrome," Neurotherapeutics 9(4):776-790, Springer, United States (Oct. 2012).

Bose, P. and Goadsby, P.J., "The Migraine Postdrome," Current Opinion in Neurology 29(3):299-301, Lippincott Williams & Wilkins, United Kingdom (Jun. 2016).

Buzzi, M.G., et al., "Prodromes and The Early Phase of The Migraine Attack: Therapeutic Relevance," Functional neurology 20(4):179-183, CIC Edizioni Internazionali, Italy (October-Dec. 2005).

Colman, I., et al., "Parenteral Dexamethasonefor Acute Severe Migraine Headache: Meta-analysis of Randomised Controlled Trials for Preventing Recurrence," BMJ (Clinical research ed.) 336(7657):1359-1361, British Medical Association, United Kingdom (Jun. 2008).

Derry, S., et al., "Diclofenac with or without an Antiemetic for Acute Migraine Headaches in Adults," The Cochrane Database of Systematic Reviews 2013(4): CD008783, Wiley, United Kingdom (Apr. 2013), 43 Pages.

Ferber-Viart, C., et al., "Effects of Acetyl-dl-leucine in Vestibular Patients: A Clinical Study Following Neurotomy and Labyrinthectomy," Audiology and Neuro- otology 14(1):17-25, Karger, Switzerland (2009).

Gilmore, B. and Michael, M., "Treatment of Acute Migraine Headache," American family physician, 83(3):271-280, American Academy of General Practice, United States (2011).

Headache Classification Subcommittee of the International Headache Society, The International Classification of Headache Disorders: 2nd edition, Cephalalgia 24(Suppl 1): 150 pages, Sage, United Kingdom (2004).

Kelman, L., "The Postdrome of the Acute Migraine Attack," Cephalalgia: An International Journal of Headache 26(2):214-220, Blackwell Publishing Ltd, United Kingdom (Feb. 2006).

Kirthi, V., et al., "Aspirin with or without an Antiemetic For Acute Migraine Headaches in Adults," The Cochrane database of systematic reviews 2013(4):CD008041, Wiley, United Kingdom (2010).

Lempert, T., et al., "Vestibular Migraine: Diagnostic Criteria," Journal of Vestibular Research: Equilibrium & Orientation 22(4): 167-172, SAGE Publications, United States (2012).

Ory, D.S., et al., "Intrathecal 2-hydroxypropyl-ß-cyclodextrin Decreases Neurological Disease Progression in Niemann-Pick Disease, Type C1: a Non- randomised, Open-label, Phase 1-2 Trial," Lancet 390(10104):1758-1768, Elsevier, United Kingdom (Oct. 2017).

Rabbie, R., et al., "Ibuprofen with Or without an Antiemetic for Acute Migraine Headaches in Adults," The Cochrane database of systematic reviews 6:(10):CD008039, Wiley, United Kingdom (Oct. 2010).

RAE-GRANT., [edited by] Lynn, J.D., et al., "The 5-Minute Neurology Consult, 2nd Edition," Lippincott Williams & Wilkins, Philadelphia, p. 26 (2004).

Rossi, P., et al., "Prodromes and Predictors of Migraine Attack," Functional Neurology 20(4): 185-191, CIC Edizioni Internazionali, Italy (October-Dec. 2005).

Wheeler, S., and Sillence, D.J., "Niemann-Pick type C Disease: Cellular Pathology and Pharmacotherapy," Journal of Neurochemistry 153(6):674-692, Wiley on behalf of the International Society for Neurochemistry, United Kingdom (Jun. 2020).

(56)                    References Cited

OTHER PUBLICATIONS

Tepper, S.J. and Tepper D.E., "Breaking the Cycle of Medication Overuse Headache," Cleveland Clinic Journal of Medicine, 77(4):236-242, Cleveland Clinic Educational Foundation, United States (2010).

Domitrz, I., et al., "Changes in Serum Amino Acids in Migraine Patients without and with Aura and their Possible Usefulness in the Study of Migraine Pathogenesis," CNS and Neurological Disorders Drug Targets, 14(3):345-349, Bentham Science Publishers, United Arab Emirates (2015).

Salzman, B., et al., "Gait and Balance Disorders in Older Adults," American Family Physician 82(1):61-68, American Academy of General Practice, United States (Jul. 2010).

Jahn, K., et al., "Dizziness and Unstable Gait in Old Age: Etiology, Diagnosis and Treatment," German Medical Journal International 112(23):387-393, German Doctors Publishing House, Germany (Jun. 2015).

Abe, et al., "Medium-Chain Triglycerides in Combination with Leucine and Vitamin D Increase Muscle Strength and Function in Frail Elderly Adults in a Randomized Controlled Trial" The Journal of Nutrition 146(5): 1017-1026, Elsevier, United States (May 2016).

Iwasaki, S., and Yamasobaet, T., "Dizziness and Imbalance in the Elderly: Age-related Decline in the Vestibular System," Aging and Disease 6(1):38-47, JKL International, United States (Feb. 2014).

Davis, O.B., et al., "NPC1-mTORC1 Signaling Couples Cholesterol Sensing to Organelle Homeostasis and Is a Targetable Pathway in Niemann-Pick Type C," Developmental Cell 56(3):260-276, Cell Press, United States (Feb. 2021).

Churchill, G.C., et al., "Acetylation Turns Leucine Into a Drug by Membrane Transporter Switching," Scientific Reports 11(1):15812, pp. 1-10, Nature Publishing Group, United Kingdom (Aug. 2021).

Auer, I.A., et al., "Paired Helical Filament Tau (PHFtau) in Niemann-pick Type C Disease is Similar to PHFtau in Alzheimer's Disease," Acta Neuropathologica 90(6):547-551, Springer Verlag, Germany (1995).

Nixon, R.A., "Niemann-Pick Type C Disease and Alzheimer's Disease: The APP- endosome Connection Fattens Up," The American Journal of Pathology 164(3):757- 761, Elsevier, United States (Mar. 2004).

Castellano, B.M., et al., "Lysosomal Cholesterol Activates Mtorc1 via an Slc38a9-niemann-pick C1 Signaling Complex," Science 355(6331): 1306-1311, American Association for the Advancement of Science, United States (Mar. 2017).

English Translation of Decision of Refusal issued in related Japanese Application No. 2021-164793, dated Apr. 25, 2023, 3 pages.

English Translation of Notice of Reason for Refusal issued in related Japanese Application No. 2021-164793, dated Sep. 29, 2022, 4 pages.

English Translation of Notice of Final Rejection issued in related Korean Application No. KR 10-2022-7021012, dated Apr. 3, 2023, 4 pages.

Communication from the European Patent Office issued in related EP Application No. 19174007.5, mailed Nov. 26, 2019, 5 pages.

English Translation of The Second Office Action issued in related Chinese Application No. CN 201780059708.6, dated Dec. 15, 2021, 4 pages.

English Translation of The First Office Action issued in related Chinese Application No. CN 201780059708.6, dated Jul. 29, 2021, 5 pages.

English Translation of Search Report issued by the Registered Search Organization in related Japanese Application No. JP 2019-507819, dated Apr. 2, 2021, 14 pages.

English Translation of Written Opinion issued in related Japanese Application No. JP 2019-507819, dated Aug. 11, 2021, 5 pages.

English Translation of Notice of Reasons for Refusal issued in related Application No. JP 2019-507819, dated Apr. 27, 2021, 4 pages.

Lukas, J., et al., "Enzyme Enhancers for the Treatment of Fabry and Pompe Disease," Molecular Therapy 23(3):456-464, Cell Press, United States (Mar. 2015).

Reagan-Shaw, S., et al., "Dose translation from animal to human studies revisited," FASEB journal 22(3):659-661, Federation of American Societies for Experimental Biology, United States (Mar. 2008).

Bremova, T., "Niemann-pick Type C: Effects of a Therapy With Acetyl-dl-leucine and Vestibular Function," Disseration for Graduate School Systemic Neurosciences Der Ludwig-maximiliansuniversitat Munchen. Presented Orally to the Public on Sep. 19, 2016 (2016), 93 Pages.

English Translation of Japanese Office Action in Counterpart Application No. 2019- 507811 dated Apr. 27, 2021, 4 pages.

English Translation of Search Report in Chinese Application No. 201780062740X, dated Aug. 14, 2021, 1 page.

Search Report in Russian Application No. 2019106493, dated Oct. 26, 2020 with English Translation.

Olesen, J., et al., "The International Classification of Headache Disorders, 3rd Edition (Beta Version)," Cephalalgia 33(9):629-808, Sage, United Kingdom (Jul. 2013).

English language Translation of Pertinent Portion of Office Action for Japanese Patent Application No. 2020-519196, dated Apr. 26, 2022, 5 pages.

Dos Santos, A.B., et al., "Treatment of Sleeping Disorders Should Be Considered in Clinical Management of Parkinson's Disease," Frontiers in Aging Neuroscience 6:273, Frontiers Research Foundation, Switzerland (Oct. 2014).

Murofushi, T., "Migraine Associated Vertigo," Equilibrium Research 70(3): 172- 175, Japan Society for Equilibrium Research, Japan (2011).

Kurokawa, K., et al., "Migraine and Vertigo: Introduction to Migrainous Vertigo," Journal of Clinical and Experimental Medicine 255(7):757-761, Springer, Switzerland (2015).

Fernandez, M., et al., " Pharmacological agents for the prevention of vestibular migraine," The Cochrane Database of Systematic Reviews 2015(6):CD010600, Wiley, United Kingdom (Jun. 2015).

Velazquez-Perez, L., et al., "Lisuride Reduces Involuntary Periodic Leg Movements in Spinocerebellar Ataxia Type 2 Patients," Cerebellum (London, England) 11(4):1051-1056, Springer, United States (Dec. 2012).

Porter, V.R., et al., "Sleep, Cognition and Dementia," Current Psychiatry Reports 17(12):1-11, Current Science, United States (Oct. 2015).

Suzuki, K., et al., "Sleep Disturbances in Neurodegenerative Diseases," Nihon Naika Gakkai zasshi. The Journal of the Japanese Society of Internal Medicine 106(2):309- 318, Nihon Naika Gakkai, Japan (Feb. 2017).

English Translation of Office Action for Japanese Patent Application No. 2020- 521938, mailed on Apr. 1, 2022, 3 Pages.

Abe, S., et al., "Medium-Chain Triglycerides in Combination with Leucine and Vitamin D Benefit Cognition in Frail Elderly Adults: A Randomized Controlled Trial," Journal of Nutritional Science and Vitaminology 63(2):133-140, University of Tokyo Press, Japan (2017).

Dehay, B., et al., "Lysosomal Impairment in Parkinson's Disease, " Movement Disorders 28(6):725-732, Wiley-Liss, United States (Jun. 2013).

Xu, J., et al., "Cholesterol Trafficking Is Required for mTOR Activation in Endothelial Cells," Proceedings of the National Academy of Sciences of the United States of America 107(10):4764-4769, National Academy of Sciences, United States (Mar. 2010).

Oldendorf, W.H., "Stereospecificity of Blood-brain Barrier Permeability to Amino Acids," The American Journal of Physiology 224(4):967-969, American Physiological Society, United States (Apr. 1973).

Shemesh, A., et al., "Suppression of mTORCI Activation in Acid -- Glucosidase- deficient Cells and Mice Is Ameliorated by Leucine Supplementation," American Journal of Physiology. Regulatory, Integrative and Comparative Physiology 307(10):R1251-R1259, American Physiological Society, United States (Nov. 2014).

Ropper, A.H. and Samuels, M.A., "Adam's And Victor's Principles of Neurology," 9th Edition, Chapter 10, McGraw Hill Education, New York (2009).

(56)　　　　　References Cited

OTHER PUBLICATIONS

Brueggemann, A., et al., "Effects of Acetyl-DL-Leucine on Ataxia and Downbeat-Nystagmus in Six Patients With Ataxia Telangiectasia," Journal of Child Neurology 37(1):20-27, Sage, United States (Jan. 2022).

Ananieva, E.A., et al., "Leucine Metabolism in T Cell Activation: mTOR Signaling and Beyond," Adv Nutr 7(4):798S-805S, American Society for Nutrition, United States (Jul. 2016).

Benard, P., et al., "Autoradiography in brain of Macaca fascicularis monkeys after injection of acetyl-DL-leucine [2-14C] (Tanganil)," Eur J Drug Metab Pharmacokinet 26(1-2):71-76, Springer Paris, France (January-Jun. 2001).

Birnbaum, S.M., et al., "Specificity of amino acid acylases," J Biol Chem 194(1):455-470, Elsevier Inc., United States (Jan. 1952).

Bloch, K., and Rittenberg, D., "The metabolism of acetylamino acids," J Biol Chem 169(3):467-476, Elsevier Inc., United States (Aug. 1947).

Brandsch, M., et al., "The intestinal H+/peptide symporter PEPT1: structure- affinity relationships," Eur J Pharm Sci 21(1):53-60, Elsevier, Netherlands (Jan. 2004).

Broer, S., and Fairweather, S.J., "Amino Acid Transport Across the Mammalian Intestine," Compr Physiol 9(1):343-373, John Wiley and Sons Inc., United States (Jan. 1, 2019).

Camenisch, G., et al., "Review of theoretical passive drug absorption models: historical background, recent developments and limitations," Pharm Acta Helv 71(5):309-327, Elsevier, Netherlands (Nov. 1996).

Cheng, Y., and Prusoff, W.H., "Relationship between the inhibition constant (K1) and the concentration of inhibitor which causes 50 per cent inhibition (150) of an enzymatic reaction," Biochem Pharmacol 22(23):3099-3108, Elsevier Inc., United States (Dec. 1973).

Churchill, G.C., et al., "Unexpected differences in the pharmacokinetics of N-acetyl-DL-leucine enantiomers after oral dosing and their clinical relevance," PLoS One 15(2):e0229585, Public Library of Science, United States (Feb. 2020).

Del Amo, E.M., et al., "Pharmacokinetic role of L-type amino acid transporters LAT1 and LAT2," Eur J Pharm Sci 35(3):161-174, Elsevier, Netherlands (Oct. 2008).

Enerson, B.E., and Drewes, L.R., "Molecular features, regulation, and function of monocarboxylate transporters: implications for drug delivery," J Pharm Sci 92(8):1531-1544, John Wiley & Sons, United States (Aug. 2003).

Eriksson, T., et al., "Clinical pharmacology of thalidomide," Eur J Clin Pharmacol 57(5):365-376, Springer Verlag, Germany (Aug. 2001).

Fagan, T., "The Lactic Acid Shuttle- It May Change How We Image the Brian," Alzforum.org, Jul. 3, 2004, accessed at https://www. alzforum.org/news/research-news/lactic-acid-shuttle-it-may-change-how-we-image-brain, accessed on Jan. 30, 2024, 4 pages.

Fagerberg, L., et al., "Analysis of the human tissue-specific expression by genome-wide integration of transcriptomics and antibody-based proteomics," Mol Cell Proteomics 13(2):397-406, Elsevier BV, United States (Feb. 2014).

Feil, K., et al., "Effects of acetyl-DL-leucine on cerebellar ataxia (ALCAT trial): study protocol for a multicenter, multinational, randomized, double-blind, placebo- controlled, crossover phase III trial," BMC Neurol 17(1):7, BioMed Central Ltd., United Kingdom (Jan. 2017).

Fields, T., et al., "A master protocol to investigate a novel therapy acetyl-L-leucine for three ultra-rare neurodegenerative diseases: Niemann-Pick type C, the GM2 gangliosidoses, and ataxia telangiectasia," Trials 22(1):84, BioMed Central, United Kingdom (Jan. 2021).

Gleeson, M.P., et al., "Probing the links between in vitro potency, ADMET and physicochemical parameters," Nat Rev Drug Discov 10(3):197-208, Nature Publishing Group, United Kingdom (Mar. 2011).

Gregori-Puigjane, E., et al., "Identifying mechanism-of-action targets for drugs and probes," Proc Natl Acad Sci USA 109(28): 11178-11183, National Academy of Sciences, United States (Jul. 2012).

Halestrap, A.P., and Wilson, M.C., "The monocarboxylate transporter family—role and regulation," IUBMB Life 64(2):109-119, Wiley-Blackwell, United States (Feb. 2012).

Hashimoto, T., et al., "Lactate sensitive transcription factor network in L6 cells: activation of MCT1 and mitochondrial biogenesis," Faseb J 21(10):2602-2612, John Wiley & Sons, United States (Aug. 2007).

Im, H.A., et al., "N-acetyl-L-tyrosine as a tyrosine source during total parenteral nutrition in adult rats," Pediatr Res 19(6):514-518, Lippincott Williams and Wilkins Ltd., United States (Jun. 1985).

International Search Report and Written Opinion for International Application No. PCT/IB2022/055513, European Patent Office, Netherlands, mailed on Sep. 20, 2022, 14 pages.

International Transporter Consortium, et al., "Membrane transporters in drug development," Nat Rev Drug Discov 9(3):215-236, Nature Publishing Group, United Kingdom (Mar. 2010).

Izyumov, D.S., et al., ""Wages of fear": transient threefold decrease in intracellular ATP level imposes apoptosis," Biochim Biophys Acta 1658(1-2):141-147, Elsevier, Netherlands (Jul. 2004).

Jha, M.K., et al., "Metabolic Connection of Inflammatory Pain: Pivotal Role of a Pyruvate Dehydrogenase Kinase-Pyruvate Dehydrogenase-Lactic Acid Axis," J Neurosci 35(42):14353-14369, Society for Neuroscience, United States (Oct. 2015).

Kalogeropoulou, D., et al., "Leucine, when ingested with glucose, synergistically stimulates insulin secretion and lowers blood glucose, " Metabolism 57(12): 1747-1752, Elsevier, Netherlands (Dec. 2008).

Kanai, Y., et al., "Expression cloning and characterization of a transporter for large neutral amino acids activated by the heavy chain of 4F2 antigen (CD98)," J Biol Chem 273(37):23629-23632, Elsevier Inc., United States (Sep. 1998).

Kaya, E., et al., "Acetyl-leucine slows disease progression in lysosomal storage disorders," Brain Commun 3(1):fcaa148, Oxford University Press, United States (Dec. 2020).

Kaya, E., et al., "Beneficial Effects of Acetyl-DL-Leucine (ADLL) in a Mouse Model of Sandhoff Disease," J Clin Med 9(4): 1050, Mdpi Ag, Switzerland (Apr. 2020).

Kennedy, B.E., et al., "Adaptations of energy metabolism associated with increased levels of mitochondrial cholesterol in Niemann-Pick type C1-deficient cells," J Biol Chem 289(23): 16278-16289, Elsevier Inc., United States (Jun. 2014).

Keogh, J.P., "Membrane transporters in drug development," Adv Pharmacol 63:1- 42, Academic Press Inc., United States (2012).

Koepsell, H. and Endou, H., "The SLC22 drug transporter family," Pflugers Arch 447(5):666-676, Springer Verlag, Germany (Feb. 2004).

Krehbiel, C.R ., and Matthews, J.C., "Absorption of Amino Acids and Peptides" in Amino Acids in Animal Nutrition, D'Mello, J.P.F., ed., pp. 41-70, CABI Publishing, United Kingdom (2003).

Leeson, P.D., and Springthorpe, B., "The influence of drug-like concepts on decision-making in medicinal chemistry," Nat Rev Drug Discov 6(11):881-890, Nature Publishing Group, United Kingdom (Nov. 2007).

Lin, L., et al., "SLC transporters as therapeutic targets: emerging opportunities," Nat Rev Drug Discov 14(8):543-560, Nature Publishing Group, United Kingdom (Aug. 2015).

Lipinski, C.A., "Drug-like properties and the causes of poor solubility and poor permeability," J Pharmacol Toxicol Methods 44(1):235-249, Elsevier Inc., United States (July-Aug. 2000).

Missner, A., and Pohl, P., "110 years of the Meyer-Overton rule: predicting membrane permeability of gases and other small compounds," Chemphyschem 10(9- 10): 1405-1414, Wiley-VCH Verlag, Germany (Jul. 2009).

Neuhauser, M., et al., "Utilization of N-acetyl-L-tyrosine and glycyl-L-tyrosine during long-term parenteral nutrition in the growing rat," Am J Clin Nutr 42(4):585- 596, American Society for Nutrition, United States (Oct. 1985).

(56)                  References Cited

OTHER PUBLICATIONS

Neuhoff, S., et al., "pH-Dependent passive and active transport of acidic drugs across Caco-2 cell monolayers," Eur J Pharm Sci 25(2-3):211-220, Elsevier, Netherlands (Jun. 2005).

Newington, J.T., et al., "Reevaluating Metabolism in Alzheimer's Disease from the Perspective of the Astrocyte-Neuron Lactate Shuttle Model," J Neurodegener Dis 2013:234572, S. Karger AG, Switzerland (2013).

Nicklin, P., et al., "Bidirectional transport of amino acids regulates mTOR and autophagy," Cell 136(3):521-534, Cell Press, United States (Feb. 2009).

Nigam, S.K., et al., "The organic anion transporter (OAT) family: a systems biology perspective," Physiol Rev 95(1):83-123, American Psychlogical Society, United States (Jan. 2015).

Olah, J., et al., "Increased glucose metabolism and ATP level in brain tissue of Huntington's disease transgenic mice, " Febs J 275(19):4740-4755, Wiley-Blackwell Publishing Ltd., United States (Oct. 2008).

Patet, C., et al., "Cerebral Lactate Metabolism After Traumatic Brain Injury," Curr Neurol Neurosci Rep 16(4):31, Current Medicine Group, United States (Apr. 2016).

Pochini, L., et al., "Membrane transporters for the special amino acid glutamine: structure/function relationships and relevance to human health," Front Chem 2:61, Frontiers Media S.A., Switerland (Aug. 2014).

PubChem, "Cyclopentyl (2S)-2-(hexanoylamino)-4-methylpentatnoate," PubChem CID 143660433, accessed at https://pubchem.ncbi.nlm.nih.gov/compound/143660433, accessed on Jan. 30, 2024, 8 pages.

Puri, S., and Juvale, K., "Monocarboxylate transporter 1 and 4 inhibitors as potential therapeutics for treating solid tumours: A review with structure-activity relationship insights," Eur J Med Chem 199:112393, Elsevier Masson, France (Aug. 2020).

Rubio-Aliaga, I. and Daniel, H., "Peptide transporters and their roles in physiological processes and drug disposition," Xenobiotica 38(7-8): 1022-1042, Informa Healthcare, United Kingdom (Jul. 2008).

Sala, N., et al., "Cerebral extracellular lactate increase is predominantly nonischemic in patients with severe traumatic brain injury," J Cereb Blood Flow Metab 33(11): 1815-1822, SAGE Publications, United States (Nov. 2013).

Sawada, K., et al., "Recognition of L-amino acid ester compounds by rat peptide transporters PEPT1 and PEPT2," J Pharmacol Exp Ther 291(2): 705-709, American Society for Pharmacology and Experimental Therapeutics, United States (Nov. 1999).

Scalise, M., et al., "The Human SLC7A5 (LAT1): The Intriguing Histidine/Large Neutral Amino Acid Transporter and Its Relevance to Human Health," Front Chem 6:243, Frontiers Media S.A., Switzerland (Jun. 2018).

Schoser, B., et al., "Treatment of restless legs syndrome with acetyl-DL-leucine—accidental findings and a small case series," Neurology 26(694):EPO2251, Lippincott Williams and Wilkins Ltd., United States (Mar. 2021).

Sheffner, A.L., et al., "Metabolic studies with acetylcysteine," Biochem Pharmacol 15(10):1523-1535, Elsevier Inc., United States (Oct. 1966).

Smith, Q.R., et al., "Kinetics of neutral amino acid transport across the blood-brain barrier," J Neurochem 49(5):1651-1658, Wiley-Blackwell Publishing Ltd., United Kingdom (Nov. 1987).

Soares-Da-Silva, P., and Serrao, M.P., "High- and low-affinity transport of L- leucine and L-DOPA by the hetero amino acid exchangers LAT1 and LAT2 in Llc- PK1 renal cells," Am J Physiol Renal Physiol 287(2):F252-F261, American Physiological Society, United States (Aug. 2004).

Strupp, M., et al., "Prophylactic treatment of migraine with and without aura with acetyl-DL-leucine: a case series," J Neurol 266(2):525-529, Springer Science + Business Media, Germany (Feb. 2019).

Sugano, K., et al., "Coexistence of passive and carrier-mediated processes in drug transport," Nat Rev Drug Discov 9(8):597-614, Nature Publishing Group, United Kingdom (Aug. 2010).

Sun, S., et al., "Lactic Acid: No. Longer an Inert and End-Product of Glycolysis," Physiology (Bethesda) 32(6):453-463, American Physiological Society, United States (Nov. 2017).

Thompson, B.R., et al., "Pharmacokinetics of gemcitabine and its amino acid ester prodrug following intravenous and oral administrations in mice, " Biochem Pharmacol 180:114127, Elsevier Inc., United States (Oct. 2020).

Van De Waterbeemd, H., et al., "Estimation of blood-brain barrier crossing of drugs using molecular size and shape, and H-bonding descriptors," J Drug Target 6(2): 151-165, Informa Healthcare, United Kingdom (1998).

Vruchte, E., et al., "Effects of N-Acetyl-Leucine and its enantiomers in Niemann- Pick disease type C cells," BioRxiv.org, accessed at https://www.biorxiv.org/content/10.1101/82622v1, accessed on Jan. 30, 2024, 13 pages.

Walter, A., and Gutknecht, J., "Monocarboxylic acid permeation through lipid bilayer membranes," J Membr Biol 77(3):255-264, Springer New York, United States (1984).

Wang, G., et al., "Intestinal OCTN2- and MCT1-targeted drug delivery to improve oral bioavailability," Asian J Pharm Sci 15(2):158-173, Shenyang Pharmaceutical University, China (Mar. 2020).

Waring, M.J., "Defining optimum lipophilicity and molecular weight ranges for drug candidates-Molecular weight dependent lower logD limits based on permeability," Bioorg Med Chem Lett 19(10):2844-2851, Elsevier Ltd., United Kingdom (May 2009).

Patterson, M.C., et al., "Oral Miglustat in Niemann-Pick type C (Npc) Disease: 1-year Interim Analysis," 11th International Congress of Human Genetics - Brisbane, Australia (Aug. 6-10, 2006) Final Program and Abstract Book, Abstract 1513, p. 267, Human Genetics Society of Australasia, Australia (Aug. 2006).

Haripriya, G.R., et al., "Incidence and Treatment Outcomes of Post Traumatic BPPV in Traumatic Brain Injury Patients," Indian J Otolaryngol Head Neck Surg 70(3):337-341, Springer, India (Apr. 2018).

Platt, F.M., et al., "Lysosomal storage diseases," Nature Reviews Disease Primers 4(1):27, pp. 1-25, Nature Publishing Group, United Kingdom (Oct. 2018).

Strupp, M., et al., "Episodic ataxia type 2," Neurotherapeutics 4(2):267-273, Elsevier, United States (Apr. 2007).

Vanier, M.T., et al., "Niemann-Pick disease type C," Orphanet Journal of Rare Diseases 5:16, pp. 1-18, BioMed Central, United Kingdom (Jun. 2010).

Las Heras, M., et al., "Understanding the phenotypic variability in Niemann-Pick disease type C (Npc): a need for precision medicine," NPJ Genome Medicine 8(1):21, Nature Publishing Group, United Kingdom (Aug. 2023).

Bremova-Ertl, T., et al., "Trial of N-Acetyl-l-Leucine in Niemann-Pick Disease Type C," New England Journal of Medicine 390(5):421-431, Massachusetts Medical Society, United States (Feb. 2024).

Fields, T., et al., "N-acetyl-L-leucine for Niemann-Pick type C: a multinational double-blind randomized placebo-controlled crossover study," Trials 24(1):361, BioMed Central, United Kingdom (May 2023).

Mengel, E., et al., "Clinical disease progression and biomarkers in Niemann-Pick disease type C: a prospective cohort study," Orphanet Journal of Rare Diseases 15(1):328, BioMed Central, United Kingdom (Nov. 2020).

Schmitz-Hubsch, T., "Scale for the assessment and rating of ataxia: development of a new clinical scale," Neurology 66(11): 1717-1720, Lippincott Williams & Wilkins, United States (Jun. 2006).

U.S. Food and Drug Administration, AQNEURSATM (levacetylleucine) for oral suspension Approval Label and Prescribing Information, IntraBio Ltd., revised Sep. 2024, 15 pages.

U.S. Food and Drug Administration, MIPLYFFA (arimoclomol) capsules, for oral use, Approval Label and Prescribing Information, Zevra Therapeutics, Inc., revised Oct. 2025, accessed at https://zevra.com/documents/MIPLYFFA-Prescribing- Information.pdf, accessed on Jan. 29, 2025, 16 pages.

Li, B., et al., "Identification and functional characterization of de novo variant in the SYNGAP1 gene causing intellectual disability,"

(56) References Cited

OTHER PUBLICATIONS

Frontiers in Genetics 14:1270175, pp. 1-7, Frontiers Research Foundation, Switzerland (Oct. 2023).

International Search Report and Written Opinion for International Application No. PCT/US2025/015918, Commissioner for Patents, United States, mailed on Apr. 2, 2025, 16 pages.

Sodhi, D.K., and Hagerman, R., "Fragile X Premutation: Medications, Therapy and Lifestyle Advice," Pharmacogenomics and Personalized Medicine 14:1689-1699, Dove Medical Press, New Zealand (Dec. 2021).

International Search Report and Written Opinion for International Application No. PCT/US2025/034430, European Patent Office, Netherlands, mailed on Jan. 30, 2026, 33 pages.

Palacios, N., et al., "Circulating plasma metabolites and cognitive function in a Puerto Rican cohort," Journal of Alzheimer's Disease 76(4): 1267-1280, IOS Press, Netherlands (May 2020).

Colaco, A., et al., "Mechanistic convergence and shared therapeutics agents in Niemann-Pick disease," Journal of Inherited Metabolic Disease 43(3):574-585, Wiley, United States (Jan. 2020).

Sindelar, M., et al., "Untargeted metabolite profiling of cerebrospinal fluid uncovers biomarkers for severity of late infantile neuronal ceroid lipofuscinosis (CLN2, Batten disease)," Scientific Reports 8:15229, pp. 1-12, Nature Publishing Group, United Kingdom (Oct. 2018).

Amador, M., et al., "Targeted versus untargeted omics - the CAFSA story," Journal of Inherited Metabolic Disease 41(3):447-456, Wiley, United States (Feb. 2018).

Kalla, R., et al., "Update on the pharmacotherapy of cerebellar and central vestibular disorders," Journal of Neurology 263:S24-S29, Springer Science+Business Media, United States (Apr. 2016).

Williams, G., "A searchable cross-platform gene expression database reveals connections between drug treatments and disease, " BMC Genomics 13:12, pp. 1-14, BioMed Central, United Kingdom (Jan. 2012).

Huhtiniemi, T., et al., "Structure-based design of pseudopeptidic inhibitors for SIRT1 and SIRT2," Journal of Medicinal Chemistry 54(19):6456-6468, American Chemical Society, United States (Oct. 2011).

Saberi-Karimian, M., et al., "The Effect of N-Acetyl-DL-Leucine on Neurological Symptoms in a Patient with Ataxia-Telangiectasia: a Case Study," Cerebellum 22(1):96-101, Springer, United States (Feb. 2023).

Pedroso, J.L., et al., "Acute cerebellar ataxia: differential diagnosis and clinical approach," Arquivos de Neuro-Psiquiatria 77(3):184-193, Brazilian Academy of Neurology, Brazil (Mar. 2019).

Tomimitsu H., and Mizusawa H., "[Episodic ataxia type 2]," Clinical Calcium 11(11):1456-1459, Abstract only, Iyaku (Medicine & Drug) Journal Co., Ltd, Japan (Nov. 2001).

* cited by examiner

TREATMENT OF LATE-ONSET NEURODEGENERATIVE DISEASES IN HETEROZYGOUS NPC1 GENE MUTATION CARRIERS

BACKGROUND OF THE INVENTION

Field of the Invention

The present disclosure provides methods of treating, preventing, or delaying the onset of a late-onset neurodegenerative disease in a subject in need thereof, and/or treating, preventing, or delaying the onset of one or more symptoms of a late-onset neurodegenerative disease in a subject in need thereof, comprising administering a therapeutically effective amount of acetyl-leucine to the subject, wherein the subject is a heterozygous NPC1 gene mutation carrier.

Background

Niemann-Pick type C (NPC) is an autosomal recessive lysosomal storage disease affecting an estimated 1:100.000 people. The disease presents with cerebellar ataxia, vertical and subsequently horizontal supranuclear saccade and gaze palsy, dystonia, pyramidal features, dysarthria, dysphagia, seizures, cognitive decline, and hepatosplenomegaly (Patterson 1993). Early-infantile, late-infantile, juvenile (31%) and adolescent/adult-onset (27%) forms occur. A positive family history of late-onset neurodegenerative disease such as Alzheimer's dementia, amyotrophic lateral sclerosis, Parkinson's disease (PD), or multiple system atrophy is common in NPC families, reported by (50.9% or 29 of 57 families) (Kresojevic et al. 2014).

NPC is metabolically and clinically closely related to Gaucher's disease (GD) where homozygosity causes a complex metabolic disease, while heterozygosity predisposes to late-onset neurodegeneration. Indeed, heterozygous glucosidase beta acid (GBA) mutations are the strongest known genetic risk factor for developing late-onset (GD) (Sidransky et al. 2009) Similarly, NPC heterozygosity may manifest clinically with a neurodegenerative disorder (Josephs et al. 2004; Harzer et al. 2014; Kluenemann et al. 2013), and genetic sequencing studies revealed NPC1 mutations in cohorts of adults with dementia or parkinsonism (Cupidi et al. 2017; Zech et al. 2013). Plasma metabolic profiles from heterozygotes are also abnormal (Probert et al. 2017). NPC heterozygosity occurs with a carrier frequency of 1:200 in the general population. But there are no systematic clinical studies of NPC heterozygotes, and it remains unknown to what degree heterozygosity may predispose a subject to late-onset neurodegeneration. Bremova-Ertl et al., *Neurology* April 2020, 94 (16) e1702-e1715.

There exists a need in the art to treat, prevent, or delay the onset of late-onset neurodegenerative diseases, e.g., NPC; and/or to treat, prevent, or delay the onset of one or more symptoms associated with late-onset neurodegenerative diseases, e.g., NPC, in heterozygous NPC1 gene mutation carriers (referred to herein as NPC heterozygotes).

BRIEF SUMMARY OF THE INVENTION

Applicant unexpectedly discovers that acetyl-leucine can be administered to NPC heterozygotes to treat, prevent, or delay the onset of NPC; and/or treat, prevent, or delay the onset of one or more symptoms associated with NPC. Thus, in one aspect, the present disclosure provides methods of: (i)

treating, preventing, or delaying the onset of a late-onset neurodegenerative disease; (ii) treating, preventing, or delaying the onset of one or more symptoms of a late-onset neurodegenerative disease; or (iii) treating, preventing, or delaying the onset of a late-onset neurodegenerative disease and preventing or delaying the onset of one or more symptoms of a late-onset neurodegenerative disease, comprising administering an effective amount of acetyl-leucine to a human subject in need thereof, wherein the subject is a heterozygous NPC1 gene mutation carrier. In another aspect, the subject is asymptomatic for the late-onset neurodegenerative disease at the time the initial dose of acetyl-leucine is administered to the subject. In another aspect, the late-onset neurodegenerative disease is NPC. In another embodiment, the acetyl-leucine is acetyl-L-leucine.

It is to be understood that both the foregoing summary and the following detailed description are exemplary and explanatory only, and are not restrictive of the invention as claimed.

DETAILED DESCRIPTION OF DRAWINGS

FIG. 1 is a bar graph showing the results of neuropsychological testing in the battery proposed by the Consortium to Establish a Registry for Alzheimer's Disease (CERAD) in heterozygous NPC1 gene mutation carriers.

Figure 2A:
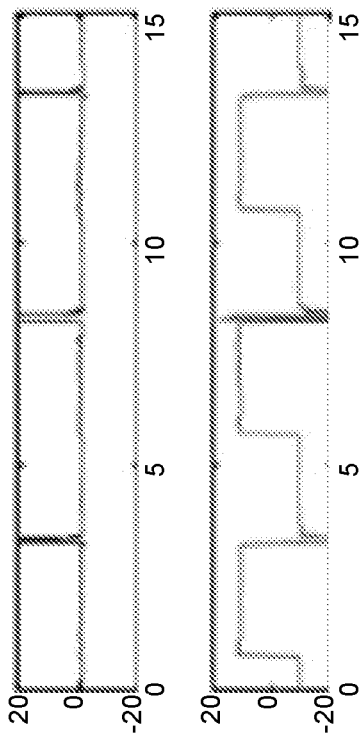
Figure 2A:
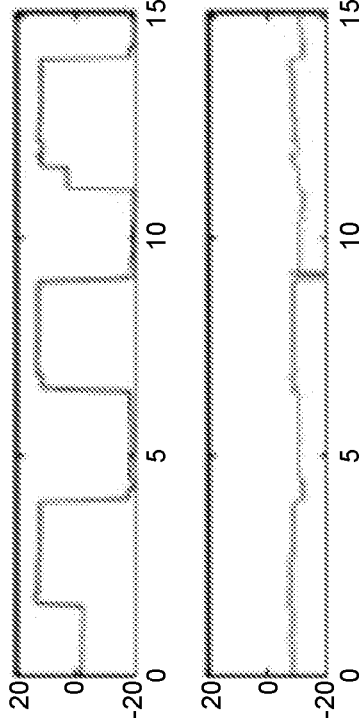

FIG. 2A is a line graph showing representative ocular motor findings with respect to 20° reflexive downward saccades in a heterozygous NPC1 gene mutation carrier. In the left-hand graphs the subject performs horizontal reflexive saccades, and in the right-hand graphs the subject performs vertical reflexive saccades. The upper panels indicate horizontal eye movement, and the lower panels indicate vertical eye movement. For example, this study shows that horizontal saccades are almost intact and that peak velocity of vertical saccades downward is lower than that of upward saccades.

Figure 2B:
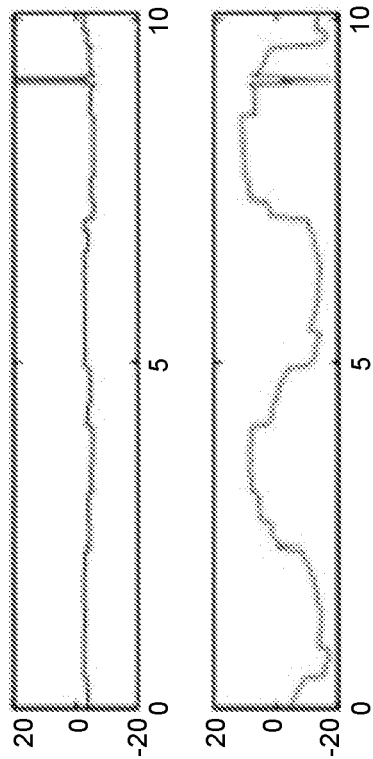
Figure 2B:
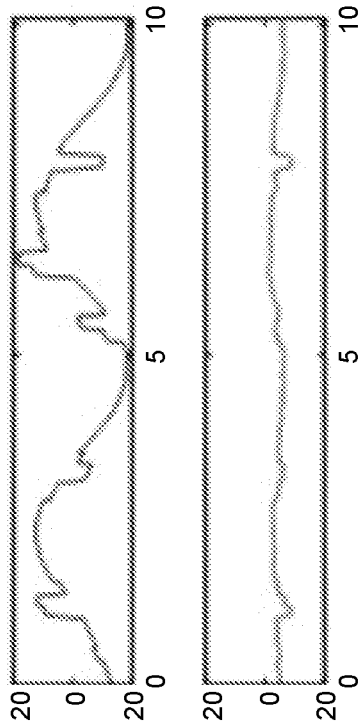

FIG. 2B is a line graph showing representative ocular motor findings with respect to 30° reflexive saccades in a heterozygous NPC1 gene mutation carrier. In the left-hand graphs the subject performs horizontal reflexive saccades, and in the right-hand graphs the subject performs vertical reflexive saccades. The upper panels indicate horizontal eye movement, and the lower panels indicate vertical eye movement.

Figure 2C:
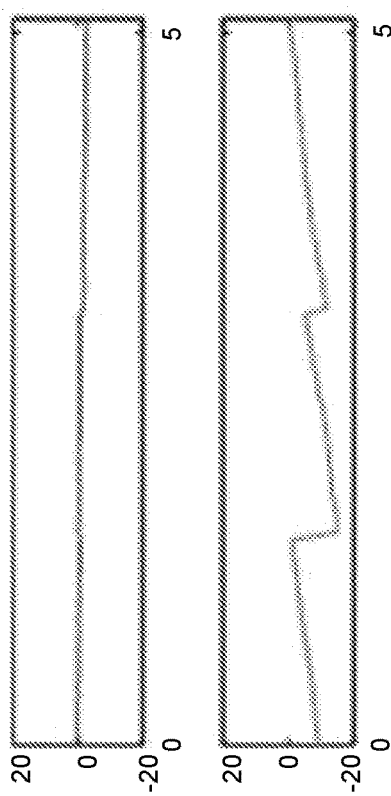
Figure 2C:
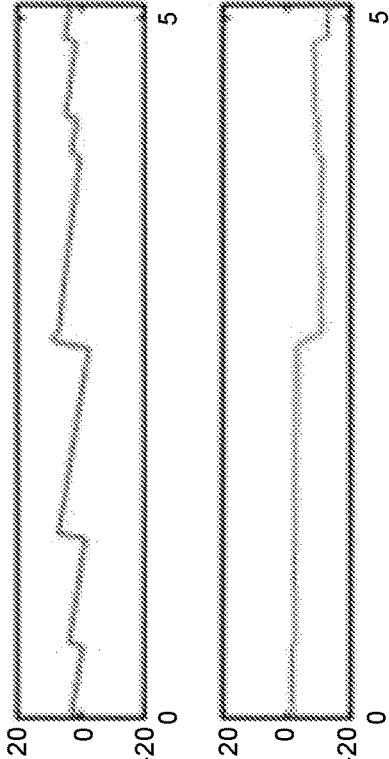
Figure 2D:
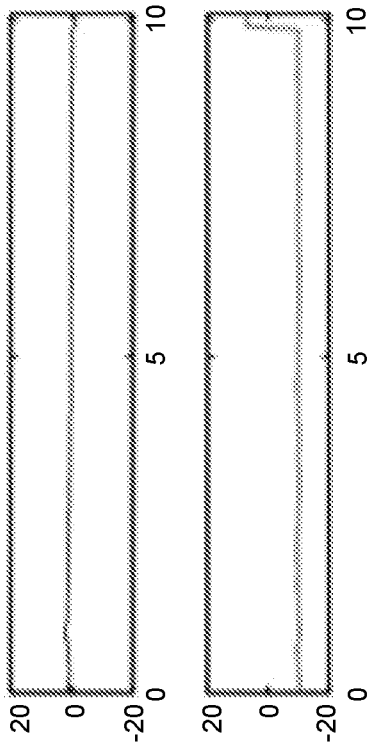
Figure 2D:
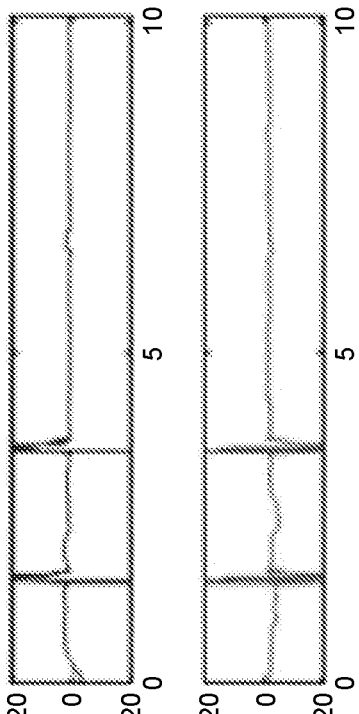
Figure 3A:
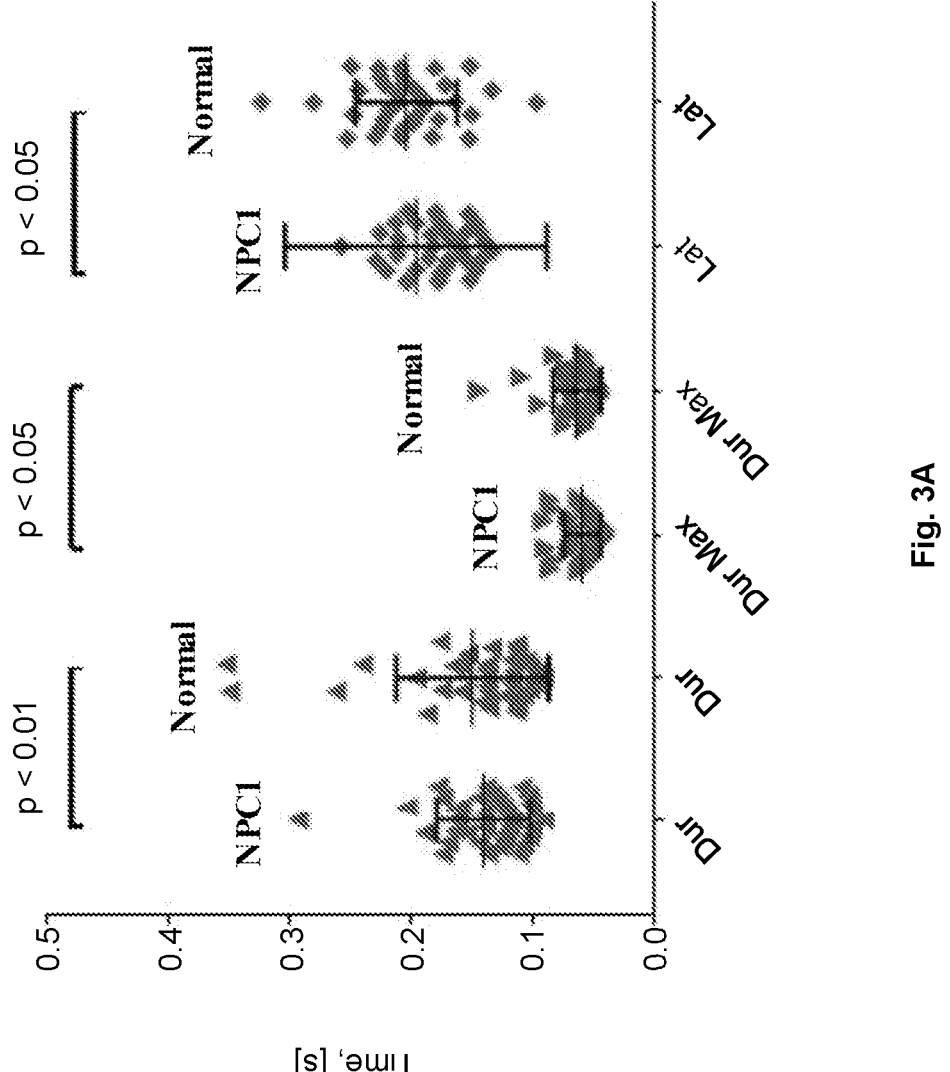

FIG. 2C is a line graph showing representative ocular motor findings with respect to horizontal and vertical self-paced saccades in a heterozygous NPC1 gene mutation carrier. In the left-hand graphs the subject performs horizontal reflexive saccades, and in the right-hand graphs the subject performs vertical reflexive saccades. The upper panels indicate horizontal eye movement, and the lower panels indicate vertical eye movement FIG. 2D is a line graph showing representative ocular motor findings with respect to gaze holding nystagmus in 10° upgaze in a heterozygous NPC1 gene mutation carrier. In the left-hand graphs, the subject performs horizontal reflexive saccades, and in the right-hand graphs, the subject performs vertical reflexive saccades. The upper panels indicate horizontal eye movement, and the lower panels indicate vertical eye movement FIG. 3A is a scatter graph showing the mean duration ("Dur"), duration to reach peak velocity ("Dur Max") and latency of 20° reflexive downward saccades in heterozygous NPC1 gene mutation carriers ("NPC1") as compared to a normal control subjects ("Normal").

Figure 3B:
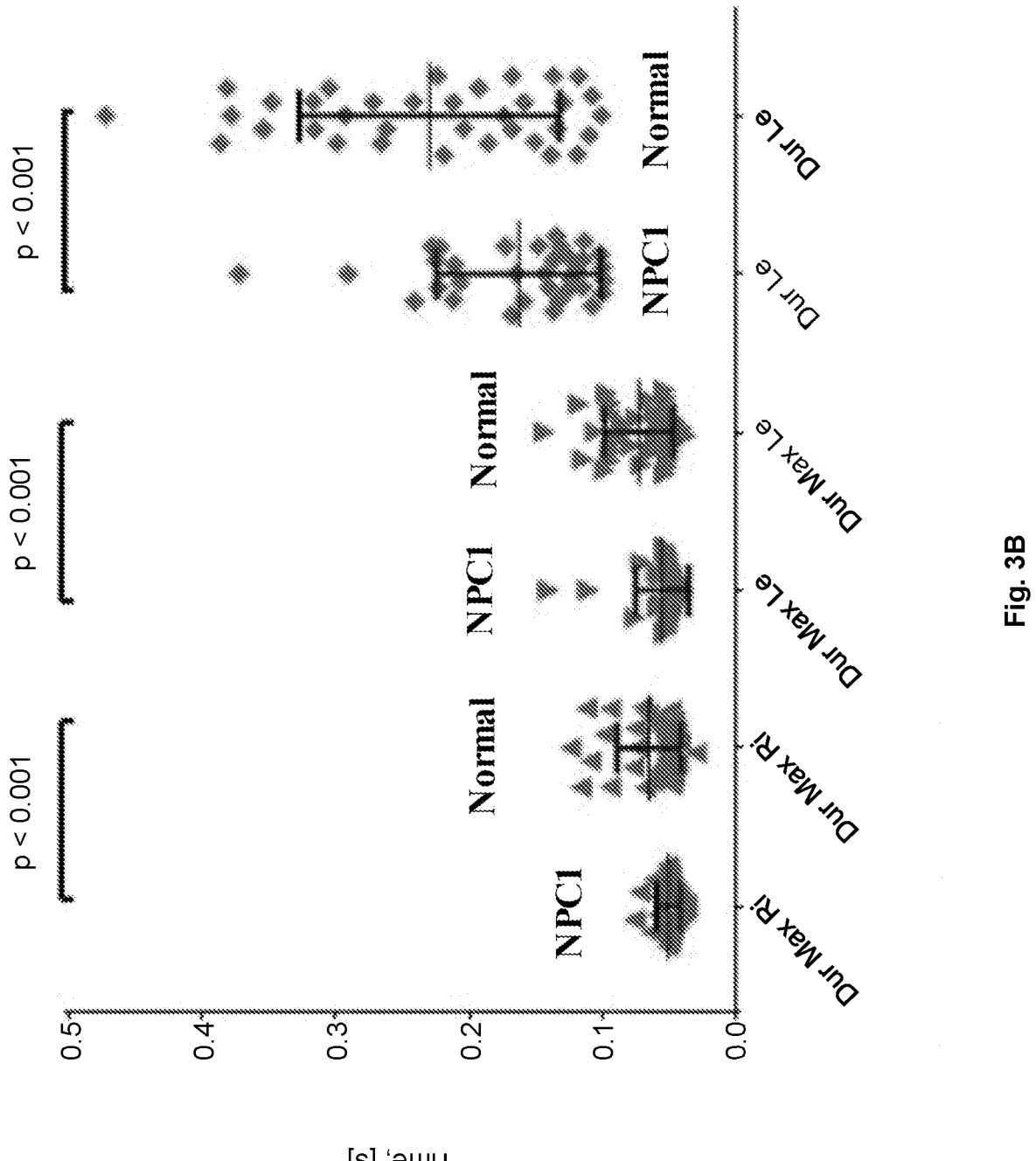

FIG. 3B is a scatter graph showing the mean duration ("Dur") and duration maximal ("Dur Max") both rightward ("Ri") and leftward ("Le") of 30° reflexive saccades in heterozygous NPC1 gene mutation carriers ("NPC1") as compared to a normal control subjects ("Normal").

Figure 3C:
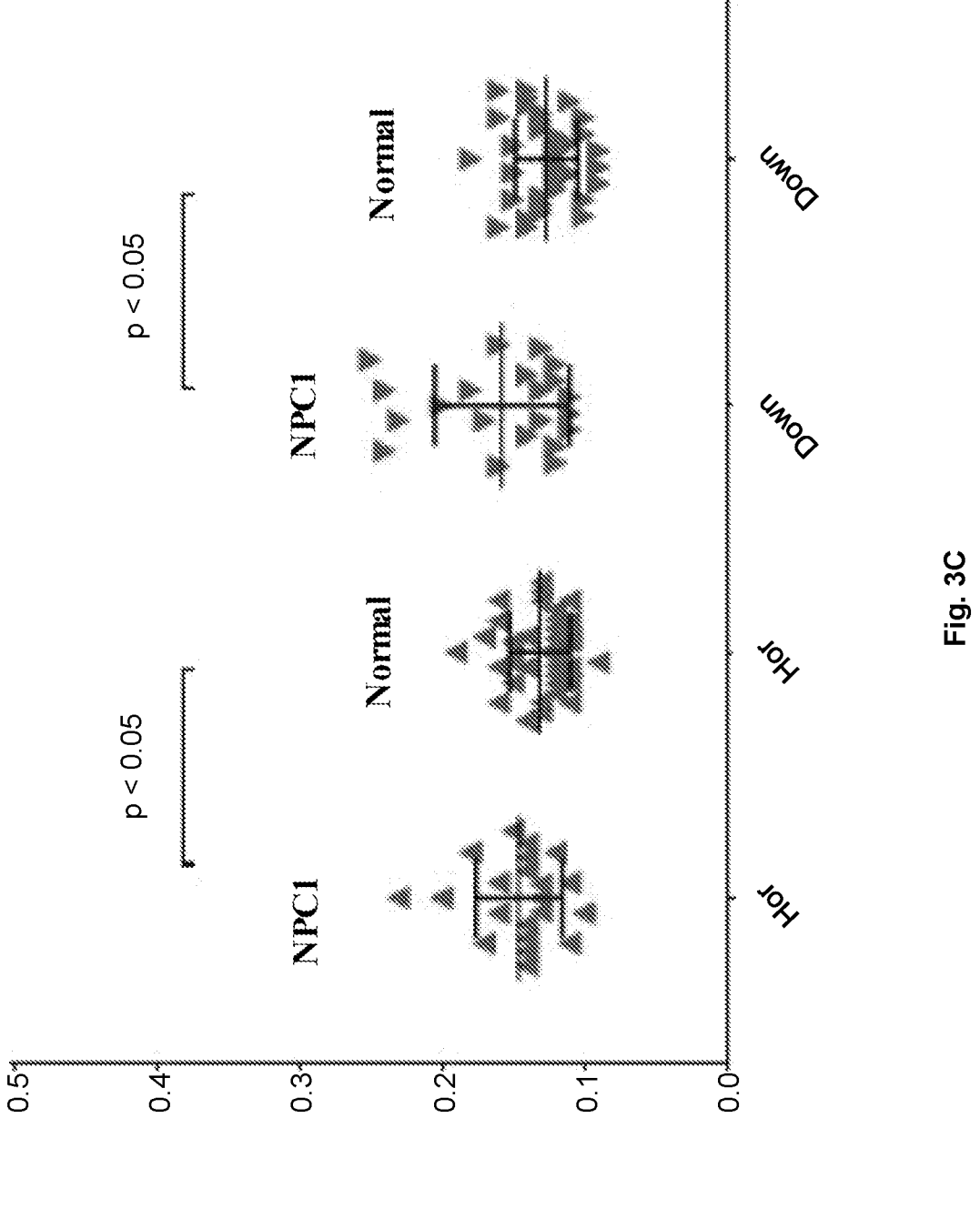
Figure 3D:
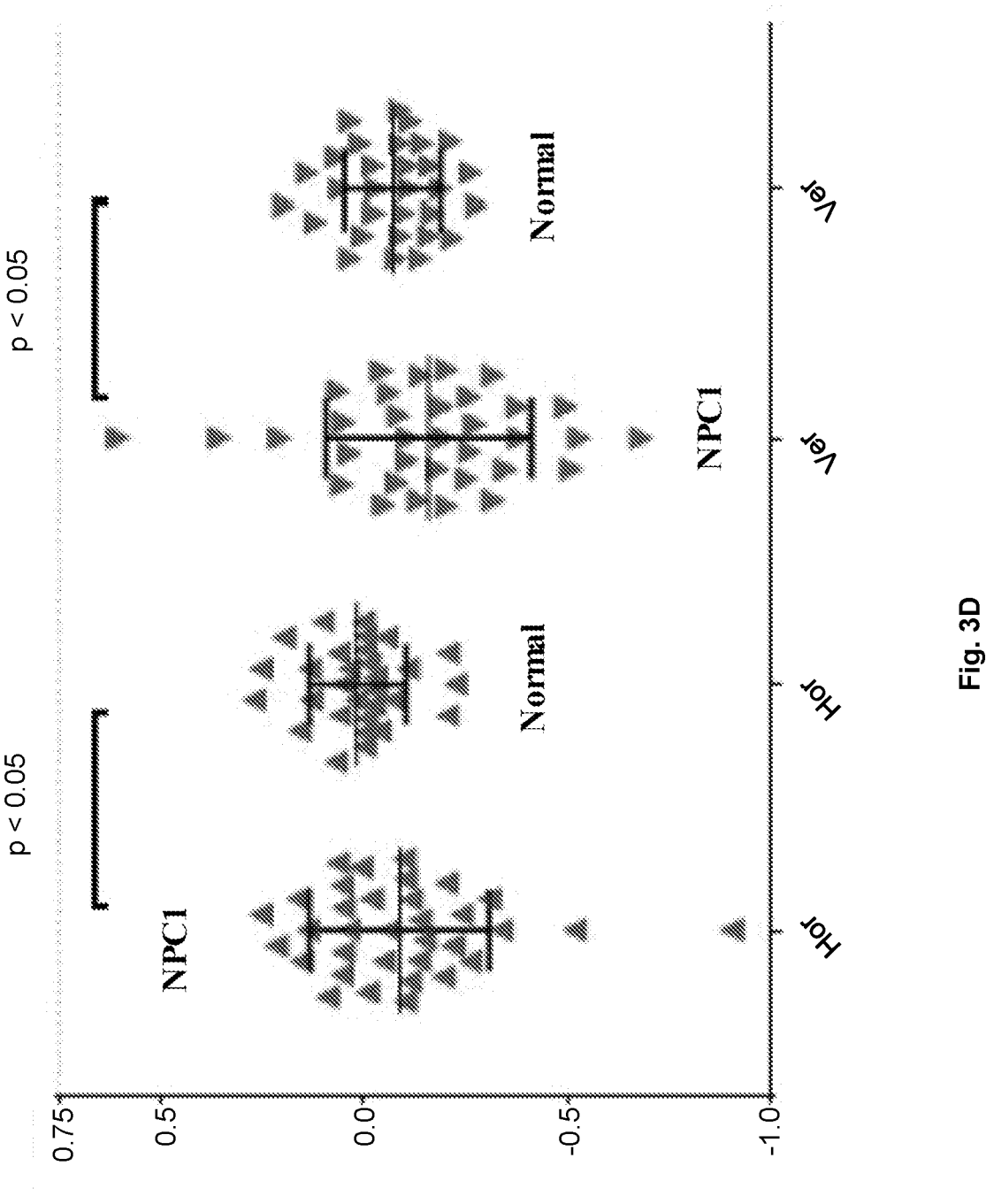

FIG. 3C is a scatter graph showing the mean duration of horizontal ("Hor") and vertical ("Down") of self-paced saccades in heterozygous NPC1 gene mutation carriers ("NPC1") as compared to a normal control subjects ("Normal"). FIG. 3D is a scatter graph showing the mean slow-phase velocity of horizontal ("Hor") and vertical ("Ver") gaze-evoked nystagmus in 10° upgaze in a heterozygous NPC1 gene mutation carriers ("NPC1") as compared to a normal control subjects ("Normal").

Figure 4:
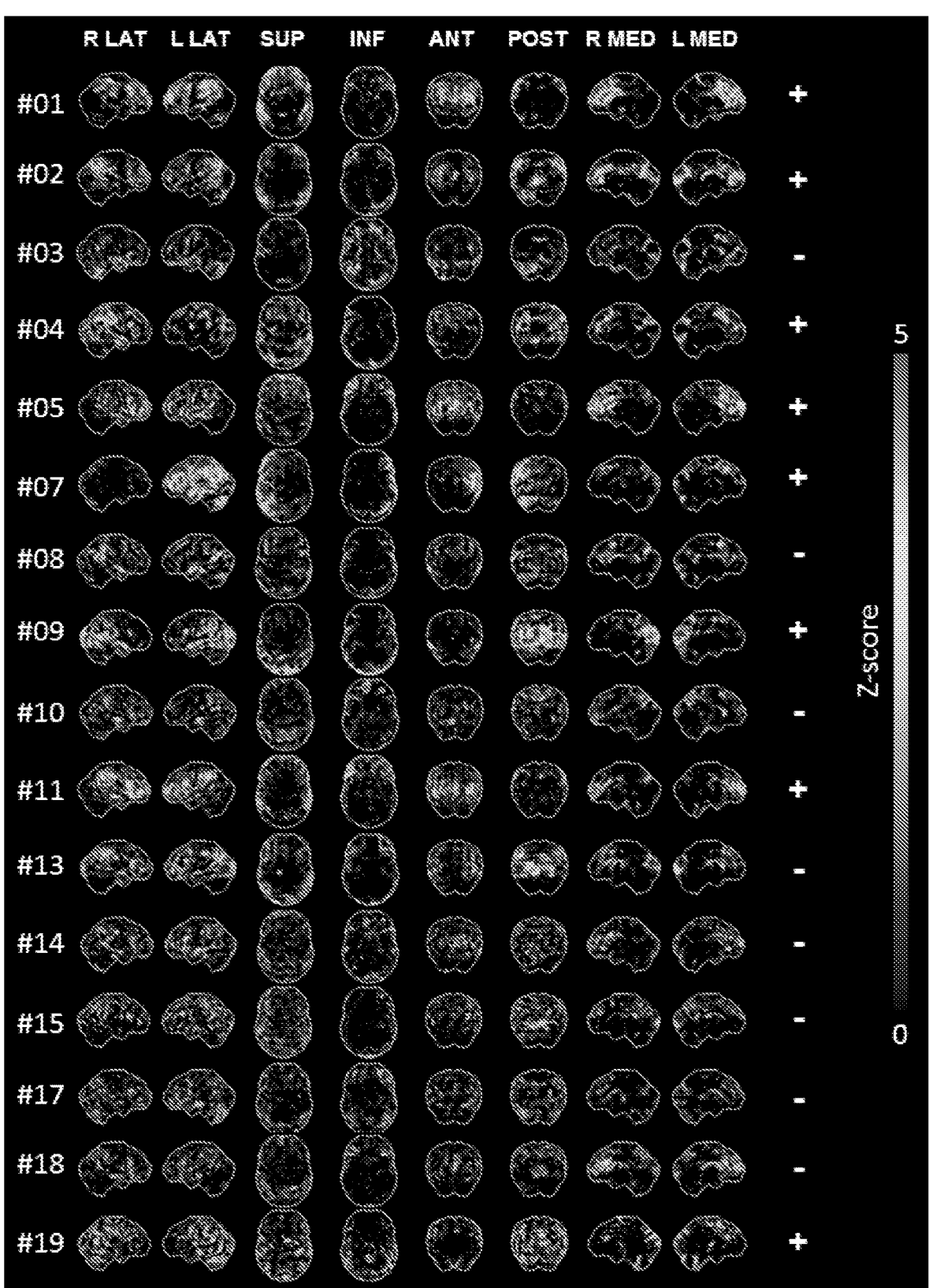

FIG. 4 is an image showing the stereotactic surface projections with individual hypometabolism patterns of NPC heterozygote subjects studied with brain FDG PET. Colored regions indicate less glucose metabolism as compared to age matched controls. The binary read of a significant pattern of neuronal injury is given as +=positive/−= negative.

Figure 5:
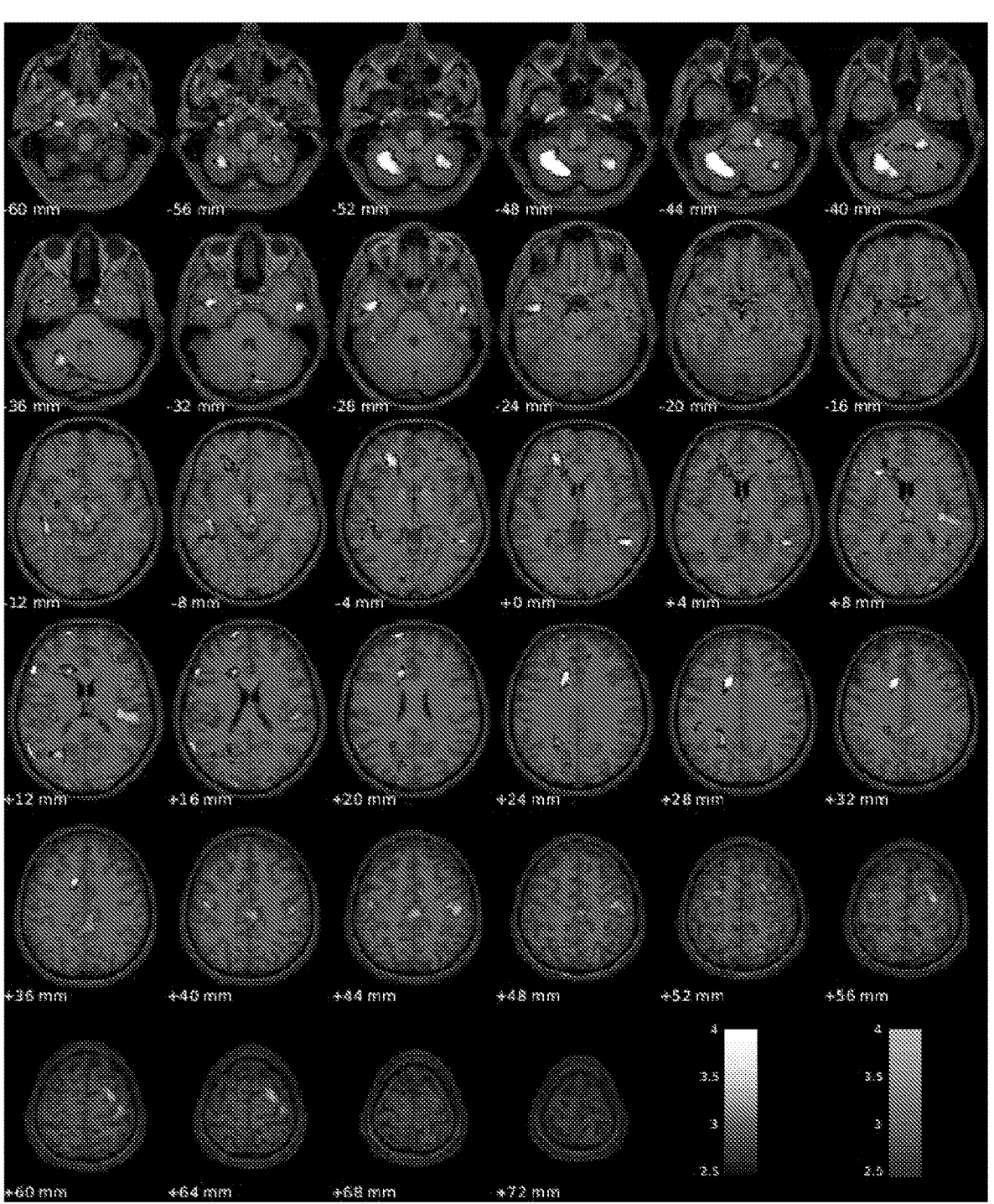

FIG. 5 is an image showing voxelwise brain FDG PET analysis in NPC heterozygote subjects.

DETAILED DESCRIPTION OF THE INVENTION

In one embodiment, the present disclosure provides a method of treating, preventing, or delaying the onset of a late-onset neurodegenerative disease and/or one or more symptoms thereof, comprising administering a therapeutically effective amount of acetyl-leucine to a human subject in need thereof, wherein the subject is a heterozygous NPC1 gene mutation carrier. This is referred to as "Embodiment 1."

The disclosure provides the following particular embodiments related to Embodiment 1.

Embodiment 2. The method of Embodiment 1, wherein the subject has any one or more of (a) an elevated level of chitotriosidase in blood or plasma; (b) an elevated level of cholestane-3β,5α,6β-triol in blood or plasma; (c) oculomotor abnormalities; or (d) hepatosplenomegaly.

Embodiment 3. The method of Embodiments 1 or 2, wherein the subject is asymptomatic for the late-onset neurodegenerative disease at the time of the initial administration of the acetyl-leucine.

Embodiment 4. The method of any one of Embodiments 1-3 for preventing or delaying the onset of the late-onset neurodegenerative disease.

Embodiment 5. The method of Embodiment 4 for delaying the onset of the late-onset neurodegenerative disease.

Embodiment 6. The method of any one of Embodiments 1-5, wherein the late-onset neurodegenerative disease is Niemann-Pick type C, Alzheimer's disease, amyotrophic lateral sclerosis, Parkinson's disease, or dementia.

Embodiment 7. The method of Embodiment 6, wherein the late-onset neurodegenerative disease is Niemann-Pick type C.

Embodiment 8. The method of Embodiment 6, wherein the late-onset neurodegenerative disease is Alzheimer's disease.

Embodiment 9. The method of Embodiment 6, wherein the late-onset neurodegenerative disease is amyotrophic lateral sclerosis.

Embodiment 10. The method of Embodiment 6, wherein the late-onset neurodegenerative disease is Parkinson's disease.

Embodiment 11. The method of Embodiment 6, wherein the late-onset neurodegenerative disease is dementia.

Embodiment 12. The method of any one of Embodiment 1-3 for preventing or delaying the onset of one or more symptoms of the late-onset neurodegenerative disease.

Embodiment 13. The method of Embodiment 12 for delaying the onset of one or more symptoms of the late-onset neurodegenerative disease.

Embodiment 14. The method of Embodiments 12 or 13, wherein the late-onset neurodegenerative disease is Niemann-Pick type C, Alzheimer's disease, amyotrophic lateral sclerosis, Parkinson's disease, or dementia.

Embodiment 15. The method of Embodiment 14, wherein the late-onset neurodegenerative disease is Niemann-Pick type C.

Embodiment 16. The method of Embodiment 15, wherein the one or more symptoms comprise cerebellar ataxia, dysarthria, dysphagia tremor, epilepsy, vertical supranuclear palsy, sleep inversion, gelastic cataplexy, dystonia, spasticity, hypotonia, ptosis, microcephaly, psychosis, progressive dementia, progressive hearing loss, bipolar disorder, or depression.

Embodiment 17. The method of Embodiment 14, wherein the late-onset neurodegenerative disease is Alzheimer's disease.

Embodiment 18. The method of Embodiment 17, wherein the one or more symptoms comprise difficulty performing familiar tasks, memory loss, disorientation to time and place, loss of good judgment, problems with abstract thinking, misplacing things, rapid mood swings, sudden and dramatic personality changes, loss of initiative, sleeping longer than usual, or loss of interest in usual activities.

Embodiment 19. The method of Embodiment 14, wherein the late-onset neurodegenerative disease is amyotrophic lateral sclerosis.

Embodiment 20. The method of Embodiment 19, wherein the one or more symptoms comprise muscle weakness or atrophy, spasticity, trouble swallowing or breathing, cramping, or slurred and nasal speech.

Embodiment 21. The method of Embodiment 14, wherein the late-onset neurodegenerative disease is Parkinson's disease.

Embodiment 22. The method of Embodiment 21, wherein the one or more symptoms comprise tremor, bradykinesia, muscle stiffness, impaired posture and balance, loss of automatic movements, speech changes, or writing changes.

Embodiment 23. The method of Embodiment 14, wherein said late-onset neurodegenerative disease is dementia.

Embodiment 24. The method of Embodiment 23, wherein the one or more symptoms comprise memory loss, difficulty communicating or finding words, difficulty with visual and spatial abilities, difficulty reasoning or problem-solving, difficulty handling complex tasks, difficulty with planning and organizing, difficulty with coordination and motor functions, confusion, or disorientation.

Embodiment 25. The method of any one of Embodiments 1-24, wherein 1 gram to 30 grams of acetyl-leucine are administered to the subject per day.

Embodiment 26. The method of any one of Embodiments 1-25, wherein the acetyl-leucine is administered to the subject in combination with another therapeutic agent.

Embodiment 27. The method of any one of Embodiments 1-26 wherein acetyl-DL-leucine is administered to the subject.

Embodiment 28. The method of any one of Embodiments 1-26 wherein acetyl-L-leucine is administered to the subject.

Embodiment 29. The method of any one of Embodiments 1-28, wherein the NPC1 gene mutation is a c.3246-25A>G mutation.

Embodiment 30. The method of any one of Embodiments 1-28, wherein the NPC1 gene mutation is a c.3246-5_3246-7del mutation.

Embodiment 31. The method of any one of Embodiments 1-28, wherein the NPC1 gene mutation is a c.2660C>T mutation.

Embodiment 32. The method of any one of Embodiments 1-28, wherein the NPC1 gene mutation is a c.2861C>T [S954L] mutation.

Embodiment 33. The method of any one of Embodiments 1-28, wherein the NPC1 gene mutation is a c.2861C>T mutation.

Embodiment 34. The method of any one of Embodiments 1-28, wherein the NPC1 gene mutation is a c.2776G>A mutation.

Embodiment 35. The method of any one of Embodiments 1-28, wherein the NPC1 gene mutation is a c.3010T>C mutation.

Embodiment 36. The method of any one of Embodiments 1-28, wherein the NPC1 gene mutation is a c.2474A>G mutation.

Embodiment 37. The method of any one of Embodiments 1-28, wherein the NPC1 gene mutation is a c.2978delG mutation.

Embodiment 38. The method of any one of Embodiments 1-28, wherein the NPC1 gene mutation is a c.3245+1dup mutation.

Embodiment 39. The method of any one of Embodiments 1-28, wherein the NPC1 gene mutation is a c.1211G>A mutation.

Embodiment 40. The method of any one of Embodiments 1-28, wherein the NPC1 gene mutation is a c.1843C>T mutation.

Embodiment 41. The method of any one of Embodiments 1-28, wherein the NPC1 gene mutation is a c.3182T>C mutation.

In another embodiment, the present disclosure provides acetyl-leucine for use in treating, preventing, or delaying the onset of a late-onset neurodegenerative disease and/or one or more symptoms thereof, wherein the subject is a heterozygous NPC1 gene mutation carrier. This is referred to as "Embodiment I."

The disclosure provides the following particular embodiments related to Embodiment I.

Embodiment II. The acetyl-leucine for use of Embodiment I, wherein the subject has any one or more of (a) an elevated level of chitotriosidase in blood or plasma; (b) an elevated level of cholestane-3β,5α,6β-triol in blood or plasma; (c) oculomotor abnormalities; or (d) hepatosplenomegaly.

Embodiment III. The acetyl-leucine for use of Embodiments I or II, wherein the subject is asymptomatic for the late-onset neurodegenerative disease at the time of the initial administration of the acetyl-leucine.

Embodiment IV. The acetyl-leucine for use of any one of Embodiments I-III for preventing or delaying the onset of the late-onset neurodegenerative disease.

Embodiment V. The acetyl-leucine for use of Embodiment IV for delaying the onset of the late-onset neurodegenerative disease.

Embodiment VI. The acetyl-leucine for use of any one of Embodiments I-V, wherein the late-onset neurodegenerative disease is Niemann-Pick type C, Alzheimer's disease, amyotrophic lateral sclerosis, Parkinson's disease, or dementia.

Embodiment VII. The acetyl-leucine for use of Embodiment VI, wherein the late-onset neurodegenerative disease is Niemann-Pick type C.

Embodiment VIII. The acetyl-leucine for use of Embodiment VI, wherein the late-onset neurodegenerative disease is Alzheimer's disease.

Embodiment IX. The acetyl-leucine for use of Embodiment VI, wherein the late-onset neurodegenerative disease is amyotrophic lateral sclerosis.

Embodiment X. The acetyl-leucine for use of Embodiment VI, wherein the late-onset neurodegenerative disease is Parkinson's disease.

Embodiment XI. The acetyl-leucine for use of Embodiment VI, wherein the late-onset neurodegenerative disease is dementia.

Embodiment XII. The acetyl-leucine for use of any one of Embodiments I-III for preventing or delaying the onset of one or more symptoms of the late-onset neurodegenerative disease.

Embodiment XIII. The acetyl-leucine for use of Embodiment XII for delaying the onset of one or more symptoms of the late-onset neurodegenerative disease.

Embodiment XIV. The acetyl-leucine for use of Embodiments XII or XIII, wherein the late-onset neurodegenerative disease is Niemann-Pick type C, Alzheimer's disease, amyotrophic lateral sclerosis, Parkinson's disease, or dementia.

Embodiment XV. The acetyl-leucine for use of Embodiment XIV, wherein the late-onset neurodegenerative disease is Niemann-Pick type C.

Embodiment XVI. The acetyl-leucine for use of Embodiment XV, wherein the one or more symptoms comprise cerebellar ataxia, dysarthria, dysphagia tremor, epilepsy, vertical supranuclear palsy, sleep inversion, gelastic cataplexy, dystonia, spasticity, hypotonia, ptosis, microcephaly, psychosis, progressive dementia, progressive hearing loss, bipolar disorder, or depression.

Embodiment XVII. The acetyl-leucine for use of Embodiment XIV, wherein the late-onset neurodegenerative disease is Alzheimer's disease.

Embodiment XVIII. The acetyl-leucine for use of Embodiment XVII, wherein the one or more symptoms comprise difficulty performing familiar tasks, memory loss, disorientation to time and place, loss of good judgment, problems with abstract thinking, misplacing things, rapid mood swings, sudden and dramatic personality changes, loss of initiative, sleeping longer than usual, or loss of interest in usual activities.

Embodiment XIX. The acetyl-leucine for use of Embodiment XIV, wherein the late-onset neurodegenerative disease is amyotrophic lateral sclerosis.

Embodiment XX. The acetyl-leucine for use of Embodiment XIX, wherein the one or more symptoms comprise muscle weakness or atrophy, spasticity, trouble swallowing or breathing, cramping, or slurred and nasal speech.

Embodiment XXI. The acetyl-leucine for use of Embodiment XIV, wherein the late-onset neurodegenerative disease is Parkinson's disease.

Embodiment XXII. The acetyl-leucine for use of Embodiment XXI, wherein the one or more symptoms comprise tremor, bradykinesia, muscle stiffness, impaired posture and balance, loss of automatic movements, speech changes, or writing changes.

Embodiment XXIII. The acetyl-leucine for use of Embodiment XIV, wherein said late-onset neurodegenerative disease is dementia.

Embodiment XXIV. The acetyl-leucine for use of Embodiment XXIII, wherein the one or more symptoms comprise memory loss, difficulty communicating or finding words, difficulty with visual and spatial abilities, difficulty reasoning or problem-solving, difficulty handling complex tasks, difficulty with planning and organizing, difficulty with coordination and motor functions, confusion, or disorientation.

Embodiment XXV. The acetyl-leucine for use of any one of Embodiments I-XXIV, wherein 1 gram to 30 grams of acetyl-leucine are administered to the subject per day.

Embodiment XXVI. The acetyl-leucine for use of any one of Embodiments I-XXV, wherein the acetyl-leucine is to be administered to the subject in combination with another therapeutic agent.

Embodiment XXVII. The acetyl-leucine for use of any one of Embodiments I-XXVI wherein acetyl-DL-leucine is administered to the subject.

Embodiment XXVIII. The acetyl-leucine for use of any one of Embodiments I-XXVI wherein acetyl-L-leucine is administered to the subject.

Embodiment XXIX. The acetyl-leucine for use of any one of Embodiments I-XXVIII, wherein the NPC1 gene mutation is a c.3246-25A>G mutation.

Embodiment XXX. The acetyl-leucine for use of any one of Embodiments I-XXVIII, wherein the NPC1 gene mutation is a c.3246-5_3246-7del mutation.

Embodiment XXXI. The acetyl-leucine for use of any one of Embodiments I-XXVIII, wherein the NPC1 gene mutation is a c.2660C>T mutation.

Embodiment XXXII. The acetyl-leucine for use of any one of Embodiments I-XXVIII, wherein the NPC1 gene mutation is a c.2861C>T [S954L] mutation.

Embodiment XXXIII. The acetyl-leucine for use of any one of Embodiments I-XXVIII, wherein the NPC1 gene mutation is a c.2861C>T mutation.

Embodiment XXXIV. The acetyl-leucine for use of any one of Embodiments I-XXVIII, wherein the NPC1 gene mutation is a c.2776G>A mutation.

Embodiment XXXV. The acetyl-leucine for use of any one of Embodiments I-XXVIII, wherein the NPC1 gene mutation is a c.3010T>C mutation.

Embodiment XXXVI. The acetyl-leucine for use of any one of Embodiments I-XXVIII, wherein the NPC1 gene mutation is a c.2474A>G mutation.

Embodiment XXXVII. The acetyl-leucine for use of any one of Embodiments I-XXVIII, wherein the NPC1 gene mutation is a c.2978delG mutation.

Embodiment XXXVIII. The acetyl-leucine for use of any one of Embodiments I-XXVIII, wherein the NPC1 gene mutation is a c.3245+1dup mutation.

Embodiment XXXIX. The acetyl-leucine for use of any one of Embodiments I-XXVIII, wherein the NPC1 gene mutation is a c.1211G>A mutation.

Embodiment XL. The acetyl-leucine for use of any one of Embodiments I-XXVIII, wherein the NPC1 gene mutation is a c.1843C>T mutation.

Embodiment XLI. The acetyl-leucine for use of any one of Embodiments I-XXVIII, wherein the NPC1 gene mutation is a c.3182T>C mutation.

In another embodiment, the present disclosure provides the use of acetyl-leucine for the manufacture of a medicament for treating, preventing, or delaying the onset of a late-onset neurodegenerative disease and/or one or more symptoms thereof, wherein the subject is a heterozygous NPC1 gene mutation carrier. This is referred to as "Embodiment A-I."

The disclosure also provides the following particular embodiments related to Embodiment A-I.

Embodiment A-II. The use of Embodiment A-I, wherein the subject has any one or more of (a) an elevated level of chitotriosidase in blood or plasma; (b) an elevated level of cholestane-3β,5α,6β-triol in blood or plasma; (c) oculomotor abnormalities; or (d) hepatosplenomegaly.

Embodiment A-III. The use of Embodiments A-I or A-II, wherein the subject is asymptomatic for the late-onset neurodegenerative disease at the time of the initial administration of the acetyl-leucine.

Embodiment A-IV. The use of any one of Embodiments A-I to A-III for preventing or delaying the onset of the late-onset neurodegenerative disease.

Embodiment A-V. The use of Embodiment A-IV for delaying the onset of the late-onset neurodegenerative disease.

Embodiment A-VI. The use of any one of Embodiments A-I to A-V, wherein the late-onset neurodegenerative disease is Niemann-Pick type C, Alzheimer's disease, amyotrophic lateral sclerosis, Parkinson's disease, or dementia.

Embodiment A-VII. The use of Embodiment A-VI, wherein the late-onset neurodegenerative disease is Niemann-Pick type C.

Embodiment A-VIII. The use of Embodiment A-VI, wherein the late-onset neurodegenerative disease is Alzheimer's disease.

Embodiment A-IX. The use of Embodiment A-VI, wherein the late-onset neurodegenerative disease is amyotrophic lateral sclerosis.

Embodiment A-X. The use of Embodiment A-VI, wherein the late-onset neurodegenerative disease is Parkinson's disease.

Embodiment A-XI. The use of Embodiment A-VI, wherein the late-onset neurodegenerative disease is dementia.

Embodiment A-XII. The use of any one of Embodiments A-I to A-III for preventing or delaying the onset one or more symptoms of the late-onset neurodegenerative disease.

Embodiment A-XIII. The use of Embodiment A-XII for delaying the onset one or more symptoms of the late-onset neurodegenerative disease.

Embodiment A-XIV. The use of Embodiments A-XII or A-XIII, wherein the late-onset neurodegenerative disease is Niemann-Pick type C, Alzheimer's disease, amyotrophic lateral sclerosis, Parkinson's disease, or dementia.

Embodiment A-XV. The use of Embodiment A-XIV, wherein the late-onset neurodegenerative disease is Niemann-Pick type C.

Embodiment A-XVI. The use of Embodiment A-XV, wherein the one or more symptoms comprise cerebellar ataxia, dysarthria, dysphagia tremor, epilepsy, vertical supranuclear palsy, sleep inversion, gelastic cataplexy, dystonia, spasticity, hypotonia, ptosis, microcephaly, psychosis, progressive dementia, progressive hearing loss, bipolar disorder, or depression.

Embodiment A-XVII. The use of Embodiment A-XIV, wherein the late-onset neurodegenerative disease is Alzheimer's disease.

Embodiment A-XVIII. The use of Embodiment A-XVII, wherein the one or more symptoms comprise difficulty performing familiar tasks, memory loss, disorientation to time and place, loss of good judgment, problems with abstract thinking, misplacing things, rapid mood swings, sudden and dramatic personality changes, loss of initiative, sleeping longer than usual, or loss of interest in usual activities.

Embodiment A-XIX. The use of Embodiment A-XIV, wherein the late-onset neurodegenerative disease is amyotrophic lateral sclerosis.

Embodiment A-XX. The use of Embodiment A-XIX, wherein the one or more symptoms comprise muscle weakness or atrophy, spasticity, trouble swallowing or breathing, cramping, or slurred and nasal speech.

Embodiment A-XXI. The use of Embodiment A-XIV, wherein the late-onset neurodegenerative disease is Parkinson's disease.

Embodiment A-XXII. The use of Embodiment A-XXI, wherein the one or more symptoms comprise tremor, bradykinesia, muscle stiffness, impaired posture and balance, loss of automatic movements, speech changes, or writing changes.

Embodiment A-XXIII. The use of Embodiment A-XIV, wherein said late-onset neurodegenerative disease is dementia.

Embodiment A-XXIV. The use of Embodiment A-XXIII, wherein the one or more symptoms comprise memory loss, difficulty communicating or finding words, difficulty with visual and spatial abilities, difficulty reasoning or problem-solving, difficulty handling complex tasks, difficulty with planning and organizing, difficulty with coordination and motor functions, confusion, or disorientation.

Embodiment A-XXV. The use of any one of Embodiments A-I to A-XXIV, wherein 1 gram to 30 grams of acetyl-leucine are administered to the subject per day.

Embodiment A-XXVI. The use of any one of Embodiments A-I to A-XXV, wherein the acetyl-leucine is to be administered to the subject in combination with another therapeutic agent.

Embodiment A-XXVII. The use of any one of Embodiments A-I to A-XXVI wherein acetyl-DL-leucine is administered to the subject.

Embodiment A-XXVIII. The use of any one of Embodiments A-I to A-XXVI wherein acetyl-L-leucine is administered to the subject.

Embodiment A-XXIX. The use of any one of Embodiments A-I to A-XXVIII, wherein the NPC1 gene mutation is a c.3246-25A>G mutation.

Embodiment A-XXX. The use of any one of Embodiments A-I to A-XXVIII, wherein the NPC1 gene mutation is a c.3246-5_3246-7del mutation.

Embodiment A-XXXI. The use of any one of Embodiments A-I to A-XXVIII, wherein the NPC1 gene mutation is a c.2660C>T mutation.

Embodiment A-XXXII. The use of any one of Embodiments A-I to A-XXVIII, wherein the NPC1 gene mutation is a c.2861C>T [S954L] mutation.

Embodiment A-XXXIII. The use of any one of Embodiments A-I to A-XXVIII, wherein the NPC1 gene mutation is a c.2861C>T mutation.

Embodiment A-XXXIV. The use of any one of Embodiments A-I to A-XXVIII, wherein the NPC1 gene mutation is a c.2776G>A mutation.

Embodiment A-XXXV. The use of any one of Embodiments A-I to A-XXVIII, wherein the NPC1 gene mutation is a c.3010T>C mutation.

Embodiment A-XXXVI. The use of any one of Embodiments A-I to A-XXVIII, wherein the NPC1 gene mutation is a c.2474A>G mutation.

Embodiment A-XXXVII. The use of any one of Embodiments A-I to A-XXVIII, wherein the NPC1 gene mutation is a c.2978delG mutation.

Embodiment A-XXXVIII. The use of any one of Embodiments A-I to A-XXVIII, wherein the NPC1 gene mutation is a c.3245+1dup mutation.

Embodiment A-XXXIX. The use of any one of Embodiments A-I to A-XXVIII, wherein the NPC1 gene mutation is a c.1211G>A mutation.

Embodiment A-XL. The use of any one of Embodiments A-I to A-XXVIII, wherein the NPC1 gene mutation is a c.1843C>T mutation.

Embodiment A-XLI. The use of any one of Embodiments A-I to A-XXVIII, wherein the NPC1 gene mutation is a c.3182T>C mutation.

In another embodiment, the present disclosure provides a pharmaceutical composition comprising acetyl-leucine for use in treating, preventing, or delaying the onset of a late-onset neurodegenerative disease and/or one or more symptoms thereof, wherein the subject is a heterozygous NPC1 gene mutation carrier. This is referred to as "Embodiment B-I."

The disclosure provides the following particular embodiments related to Embodiment B-I.

Embodiment B-II. The pharmaceutical composition for use of Embodiment B-I, wherein the subject has any one or more of (a) an elevated level of chitotriosidase in blood or plasma; (b) an elevated level of cholestane-3β,5α,6β-triol in blood or plasma; (c) oculomotor abnormalities; or (d) hepatosplenomegaly.

Embodiment B-III. The pharmaceutical composition for use of Embodiments B-I or B-II, wherein the subject is asymptomatic for the late-onset neurodegenerative disease at the time of the initial administration of the acetyl-leucine.

Embodiment B-IV. The pharmaceutical composition for use of any one of Embodiments B-I to B-III for preventing or delaying the onset of the late-onset neurodegenerative disease.

Embodiment B-V. The pharmaceutical composition for use of Embodiment B-IV for delaying the onset of the late-onset neurodegenerative disease.

Embodiment B-VI. The pharmaceutical composition for use of any one of Embodiments B-I to B-V, wherein the late-onset neurodegenerative disease is Niemann-Pick type C, Alzheimer's disease, amyotrophic lateral sclerosis, Parkinson's disease, or dementia.

Embodiment B-VII. The pharmaceutical composition for use of Embodiment B-VI, wherein the late-onset neurodegenerative disease is Niemann-Pick type C.

Embodiment B-VIII. The pharmaceutical composition for use of Embodiment B-VI, wherein the late-onset neurodegenerative disease is Alzheimer's disease.

Embodiment B-IX. The pharmaceutical composition for use of Embodiment B-VI, wherein the late-onset neurodegenerative disease is amyotrophic lateral sclerosis.

Embodiment B-X. The pharmaceutical composition for use of Embodiment B-VI, wherein the late-onset neurodegenerative disease is Parkinson's disease.

Embodiment B-XI. The pharmaceutical composition for use of Embodiment B-VI, wherein the late-onset neurodegenerative disease is dementia.

Embodiment B-XII. The pharmaceutical composition for use of any one of Embodiments B-I to B-III for preventing or delaying the onset one or more symptoms of the late-onset neurodegenerative disease.

Embodiment B-XIII. The pharmaceutical composition for use of Embodiment B-XII for delaying the onset one or more symptoms of the late-onset neurodegenerative disease.

Embodiment B-XIV. The pharmaceutical composition for use of Embodiments B-XII or B-XIII, wherein the late-onset neurodegenerative disease is Niemann-Pick type C, Alzheimer's disease, amyotrophic lateral sclerosis, Parkinson's disease, or dementia.

Embodiment B-XV. The pharmaceutical composition for use of Embodiment B-XIV, wherein the late-onset neurodegenerative disease is Niemann-Pick type C.

Embodiment B-XVI. The pharmaceutical composition for use of Embodiment B-XV, wherein the one or more symptoms comprise cerebellar ataxia, dysarthria, dysphagia tremor, epilepsy, vertical supranuclear palsy, sleep inversion, gelastic cataplexy, dystonia, spasticity, hypotonia, ptosis, microcephaly, psychosis, progressive dementia, progressive hearing loss, bipolar disorder, or depression.

Embodiment B-XVII. The pharmaceutical composition for use of Embodiment B-XIV, wherein the late-onset neurodegenerative disease is Alzheimer's disease.

Embodiment B-XVIII. The pharmaceutical composition for use of Embodiment B-XVII, wherein the one or more symptoms comprise difficulty performing familiar tasks, memory loss, disorientation to time and place, loss of good judgment, problems with abstract thinking, misplacing things, rapid mood swings, sudden and dramatic personality changes, loss of initiative, sleeping longer than usual, or loss of interest in usual activities.

Embodiment B-XIX. The pharmaceutical composition for use of Embodiment B-XIV, wherein the late-onset neurodegenerative disease is amyotrophic lateral sclerosis.

Embodiment B-XX. The pharmaceutical composition for use of Embodiment B-XIX, wherein the one or more symptoms comprise muscle weakness or atrophy, spasticity, trouble swallowing or breathing, cramping, or slurred and nasal speech.

Embodiment B-XXI. The pharmaceutical composition for use of Embodiment B-XIV, wherein the late-onset neurodegenerative disease is Parkinson's disease.

Embodiment B-XXII. The pharmaceutical composition for use of Embodiment B-XXI, wherein the one or more symptoms comprise tremor, bradykinesia, muscle stiffness, impaired posture and balance, loss of automatic movements, speech changes, or writing changes.

Embodiment B-XXIII. The pharmaceutical composition for use of Embodiment B-XIV, wherein said late-onset neurodegenerative disease is dementia.

Embodiment B-XXIV. The pharmaceutical composition for use of Embodiment B-XXIII, wherein the one or more symptoms comprise memory loss, difficulty communicating or finding words, difficulty with visual and spatial abilities, difficulty reasoning or problem-solving, difficulty handling complex tasks, difficulty with planning and organizing, difficulty with coordination and motor functions, confusion, or disorientation.

Embodiment B-XXV. The pharmaceutical composition for use of any one of Embodiments B-I to B-XXIV, wherein 1 gram to 30 grams of acetyl-leucine are administered to the subject per day.

Embodiment B-XXVI. The pharmaceutical composition for use of any one of Embodiments B-I to B-XXV, wherein the acetyl-leucine is to be administered to the subject in combination with another therapeutic agent.

Embodiment B-XXVII. The pharmaceutical composition for use of any one of Embodiments B-I to B-XXVI, wherein acetyl-DL-leucine is administered to the subject.

Embodiment B-XXVIII. The pharmaceutical composition for use of any one of Embodiments B-I to B-XXVI, wherein acetyl-L-leucine is administered to the subject.

Embodiment B-XXIX. The pharmaceutical composition for use of any one of Embodiments B-I to B-XXVIII, wherein the NPC1 gene mutation is a c.3246-25A>G mutation.

Embodiment B-XXX. The pharmaceutical composition for use of any one of Embodiments B-I to B-XXVIII, wherein the NPC1 gene mutation is a c.3246-5_3246-7del mutation.

Embodiment B-XXXI. The pharmaceutical composition for use of any one of Embodiments B-I to B-XXVIII, wherein the NPC1 gene mutation is a c.2660C>T mutation.

Embodiment B-XXXII. The pharmaceutical composition for use of any one of Embodiments B-I to B-XXVIII, wherein the NPC1 gene mutation is a c.2861C>T [S954L] mutation.

Embodiment B-XXXIII The pharmaceutical composition for use of any one of Embodiments B-I to B-XXVIII, wherein the NPC1 gene mutation is a c.2861C>T mutation.

Embodiment B-XXXIV. The pharmaceutical composition for use of any one of Embodiments B-I to B-XXVIII, wherein the NPC1 gene mutation is a c.2776G>A mutation.

Embodiment B-XXXV. The pharmaceutical composition for use of any one of Embodiments B-I to B-XXVIII, wherein the NPC1 gene mutation is a c.3010T>C mutation.

Embodiment B-XXXVI. The pharmaceutical composition for use of any one of Embodiments B-I to B-XXVIII, wherein the NPC1 gene mutation is a c.2474A>G mutation.

Embodiment B-XXXVII. The pharmaceutical composition for use of any one of Embodiments B-I to B-XXVIII, wherein the NPC1 gene mutation is a c.2978delG mutation.

Embodiment B-XXXVIII. The pharmaceutical composition for use of any one of Embodiments B-I to B-XXVIII, wherein the NPC1 gene mutation is a c.3245+1dup mutation.

Embodiment B-XXXIX. The pharmaceutical composition for use of any one of Embodiments B-I to B-XXVIII, wherein the NPC1 gene mutation is a c.1211G>A mutation.

Embodiment B-XL. The pharmaceutical composition for use of any one of Embodiments B-I to B-XXVIII, wherein the NPC1 gene mutation is a c.1843C>T mutation.

Embodiment B-XLI. The pharmaceutical composition for use of any one of Embodiments B-I to B-XXVIII, wherein the NPC1 gene mutation is a c.3182T>C mutation.

Definitions

In some embodiments, the prophylactic methods described herein are contemplated for a subject, e.g., a human heterozygous NPC1 gene mutation carrier, at risk for developing a late-onset neurodegenerative disease, but who do not yet meet the clinical criteria for the diagnosis as having the disease. See, e.g., Patterson et al., *Neurol Clin Pract.* 7:499-511 (2017). Without being bound to a particular theory, it is believed that subjects in this preclinical disease stage represent a continuum from completely symptom-free subjects to subjects who demonstrate deficits and abnormalities but do not yet meet the clinical criteria for diagnosis as having a late-onset neurodegenerative disease. The term "asymptomatic" as used herein refers to a subject who falls within this continuum.

Methods such as Polymerase Chain Reaction (PCR) to determine whether a subject is a heterozygous NPC1 gene mutation carrier are known in the art. See, e.g., Zech et al., *PLoS One* 8(12):e82879 (2013).

As used herein, the singular forms "a," "an," and "the" include plural reference.

The term "acetyl-leucine" refers collectively to N-acetyl-DL-leucine (ADLL), or a pharmaceutically acceptable salt thereof; N-acetyl-D-leucine (ADL), or a pharmaceutically acceptable salt thereof; and N-acetyl-L-leucine (ALL), or a pharmaceutically acceptable salt thereof. The term acetyl-leucine includes isotopically-labelled analogs of N-acetyl-DL-leucine, N-acetyl-D-leucine, and N-acetyl-L-leucine, wherein one or more atoms are replaced by an atom having a different atomic mass or mass number. Examples of isotopes that can be incorporated include isotopes of hydrogen, carbon, nitrogen, and oxygen, such as $^2H$ (or deuterium (D)), $^3H$, $^{11}C$, $^{13}C$, $^{14}C$, $^{15}N$, and $^{17}O$. In one embodiment, provided is an isotopically-labelled analog of acetyl-leucine, wherein substantially all of the atoms at a position within acetyl-leucine are replaced by an atom having a different atomic mass or mass number. In another embodiment, provided is an isotopically-labelled analog of acetyl-leucine, wherein a portion of the atoms at a position within acetyl-leucine are replaced, e.g., acetyl-leucine is enriched at one or more positions with an atom having a different atomic mass or mass number. Isotopically-labelled acetyl-leucine can be prepared by methods known in the art.

In one embodiment, the N-acetyl-DL-leucine, N-acetyl-D-leucine, or N-acetyl-L-leucine used in the methods of the present disclosure is not isotopically-labelled.

In one embodiment, the isotopically-labelled analog is a deuterated analog of N-acetyl-DL-leucine, N-acetyl-D-leucine, or N-acetyl-L-leucine, wherein one or more hydrogen atoms are replaced with deuterium. In one embodiment, one hydrogen atom of N-acetyl-DL-leucine, N-acetyl-D-leucine, or N-acetyl-L-leucine is replaced with deuterium. In another embodiment, two hydrogen atoms of N-acetyl-DL-leucine, N-acetyl-D-leucine, or N-acetyl-L-leucine are replaced with deuterium. In another embodiment, three hydrogen atoms of N-acetyl-DL-leucine, N-acetyl-D-leucine, or N-acetyl-L-leucine are replaced with deuterium. In another embodiment, four hydrogen atoms of N-acetyl-DL-leucine, N-acetyl-D-leucine, or N-acetyl-L-leucine are replaced with deuterium. In another embodiment, five hydrogen atoms of N-acetyl-DL-leucine, N-acetyl-D-leucine, or N-acetyl-L-leucine are replaced with deuterium. In another embodiment, six hydrogen atoms of N-acetyl-DL-leucine, N-acetyl-D-leucine, or N-acetyl-L-leucine are replaced with deuterium.

In one embodiment, the acetyl-leucine used in the methods of the present disclosure is N-acetyl-DL-leucine, or a deuterated analog thereof. In another embodiment, the acetyl-leucine used in the methods of the present disclosure is N-acetyl-D-leucine, or a deuterated analog thereof. In another embodiment, the acetyl-leucine used in the methods of the present disclosure is N-acetyl-L-leucine, or a deuterated analog thereof. In another embodiment, the acetyl-leucine used in the methods of the present disclosure is N-acetyl-L-leucine.

The terms "administer," "administration," or "administering" as used herein refer to (1) providing, giving, dosing and/or prescribing by either a health practitioner or his authorized agent or under his direction, acetyl-leucine, or a pharmaceutical composition thereof, and (2) putting into, taking or consuming by the patient or person himself or herself, acetyl-leucine or a pharmaceutical composition thereof.

Any reference to "acetyl-leucine" includes pharmaceutically acceptable salts of the same, even if not expressly stated.

A "pharmaceutically acceptable salt" as referred to herein, is any salt preparation that is appropriate for use in a pharmaceutical application. Pharmaceutically acceptable salts include, but are not limited to, amine salts, such as N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chloro-benzyl-2-pyrrolidin-1'-ylmethylbenzimidazole, diethylamine and other alkylamines, piperazine, tris(hydroxymethyl)aminomethane and the like; alkali metal salts, such as lithium, potassium, sodium and the like; alkali earth metal salts, such as barium, calcium, magnesium and the like; transition metal salts, such as zinc, aluminum and the like; other metal salts, such as sodium hydrogen phosphate, disodium phosphate and the like; mineral acids, such as hydrochlorides, sulfates and the like; and salts of organic acids, such as acetates, lactates, malates, tartrates, citrates, ascorbates, succinates, butyrates, valerates, fumarates and the like.

Acetyl-leucine may be formulated and administered to a subject in accordance with known teachings in the art. For example, acetyl-DL-leucine, acetyl-D-leucine, or acetyl-L-leucine may be formulated as a pharmaceutical composition. In some embodiments, acetyl-DL-leucine, acetyl-D-leucine, or acetyl-L-leucine are administered to a subject as a part of pharmaceutical composition. Such pharmaceutical compositions comprise acetyl-DL-leucine, acetyl-D-leucine, or acetyl-L-leucine, and a pharmaceutically acceptable carrier. Reference to the pharmaceutical composition encompasses the active agent alone, i.e., acetyl-DL-leucine, acetyl-D-leucine, or acetyl-L-leucine, or in the form of a pharmaceutical composition.

The pharmaceutical composition may take any of a number of different forms depending, in particular, on the manner in which it is to be used. Thus, for example, it may be in the form of a powder, tablet, capsule, liquid, ointment, cream, gel, hydrogel, aerosol, spray, micellar solution, transdermal patch, liposome suspension or any other suitable form that may be administered to a person or animal in need of treatment.

A "pharmaceutically acceptable carrier" as referred to herein, is any known compound or combination of known compounds, e.g., excipients, carriers, etc., that are known to those skilled in the art to be useful in formulating pharmaceutical compositions. It will be appreciated that the carrier of the pharmaceutical composition should be one which is tolerated by the subject to whom it is given.

In one embodiment, the pharmaceutically acceptable carrier may be a solid, and the composition may be in the form of a powder or tablet. A solid pharmaceutically acceptable carrier may include, but is not limited to, one or more substances which may also act as flavouring agents, buffers, lubricants, stabilisers, solubilisers, suspending agents, wetting agents, emulsifiers, dyes, fillers, glidants, compression aids, inert binders, sweeteners, preservatives, dyes, coatings, or tablet-disintegrating agents. The carrier may also be an encapsulating material. In powders, the carrier may be a finely divided solid that is in admixture with the finely divided active agents according to the invention. In tablets, the active agent may be mixed with a carrier having the necessary compression properties in suitable proportions and compacted in the shape and size desired. The powders and tablets may, for example, contain up to 99% of the active agents. Suitable solid carriers include, for example, calcium phosphate, magnesium stearate, talc, sugars, lactose, dextrin, starch, gelatin, cellulose, polyvinylpyrrolidine, low melting waxes and ion exchange resins. In another embodiment, the pharmaceutically acceptable carrier may be a gel and the composition may be in the form of a cream or the like.

The carrier may include, but is not limited to, one or more excipients or diluents. Examples of such excipients are gelatin, gum arabicum, lactose, microcrystalline cellulose, starch, sodium starch glycolate, calcium hydrogen phosphate, magnesium stearate, talcum, colloidal silicon dioxide, and the like.

In another embodiment, the pharmaceutically acceptable carrier may be a liquid. In one embodiment, the pharmaceutical composition is in the form of a solution. Liquid carriers are used in preparing solutions, suspensions, emulsions, syrups, elixirs and pressurized compositions. Acetyl-leucine may be dissolved or suspended in a pharmaceutically acceptable liquid carrier such as water, an organic solvent, a mixture of both or pharmaceutically acceptable oils or fats. The liquid carrier may contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid carriers for oral and parenteral administration include water (partially containing additives as above, e.g. cellulose derivatives, such as sodium carboxymethyl cellulose solution), alcohols (including monohydric alcohols and polyhydric alcohols, e.g. glycols) and their derivatives, and oils (e.g. fractionated coconut oil and *arachis* oil). For parenteral administration, the carrier may also be an oily ester such as ethyl oleate and isopropyl myristate. Sterile liquid carriers are useful in sterile liquid form compositions for parenteral administration. The liquid carrier for pressurised compositions may be a halogenated hydrocarbon or other pharmaceutically acceptable propellant.

Liquid pharmaceutical compositions, which are sterile solutions or suspensions, may be utilised by, for example, intramuscular, intrathecal, epidural, intraperitoneal, intravenous and subcutaneous injection. The active agent may be prepared as a sterile solid composition that may be dissolved or suspended at the time of administration using sterile water, saline, or other appropriate sterile injectable medium.

The compositions may be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The compositions may also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Compositions may alternatively be administered by inhalation (e.g. intranasally). Compositions may also be formulated for topical use. For instance, creams or ointments may be applied to the skin.

Acetyl-leucine may be incorporated within a slow- or delayed-release device. Such devices may, for example, be inserted on or under the skin, and the medicament may be released over weeks or even months. Such devices may be advantageous when long-term treatment with acetyl-leucine used according to the present disclosure is required and which may require frequent administration (e.g. at least daily administration).

In one embodiment, the pharmaceutical composition is a solid oral dosage form, such as a tablet. In tablets, the active agent may be mixed with a vehicle, such as a pharmaceutically acceptable carrier, having the necessary compression properties in suitable proportions and compacted in the shape and size desired. The tablets may contain up to 99% by weight of the active agents.

Pharmaceutical compositions in solid oral dosage form, such as tablets, may be prepared by any method known in the art of pharmacy. Pharmaceutical compositions are usually prepared by mixing the active agent with conventional pharmaceutically acceptable carriers.

A tablet may be formulated as is known in the art. Tanganil®, for example, includes wheat starch, pregelatinised maize (corn) starch, calcium carbonate and magnesium stearate as excipients. The same, or similar, excipients, for example, may be employed with the present disclosure.

The composition of each 700 mg Tanganil® tablet is as follows: 500 mg acetyl-DL-leucine, 88 mg wheat starch, 88 mg pregelatinised maize (corn) starch, 13 mg calcium carbonate and 11 mg magnesium stearate. The same tablets, for example, may be employed in the methods of the present disclosure.

As discussed above, acetyl-leucine may be formulated and administered as a pharmaceutical composition taking any number of different forms. For example, acetyl-leucine may be formulated as a pharmaceutical composition to facilitate its delivery across the blood-brain barrier. As a further example, acetyl-leucine may be formulated as a pharmaceutical composition for bypassing the blood-brain barrier. Formulations that facilitate delivery across the blood-brain barrier or that are suitable for administration in a manner that bypasses the blood-brain barrier may be used to prepare and administer leucine (not acetylated) as described herein.

In one embodiment, the pharmaceutical composition, e.g., comprising acetyl-L-leucine, or salt thereof, is formulated for nanodelivery, e.g., colloidal drug-carrier systems. Suitable examples include but are not limited to liposomes, nanoparticles (e.g., polymeric, lipid and inorganic nanoparticles), nanogels, dendrimers, micelles, nanoemulsions, polymersomes, exosomes, and quantum dots. See, e.g., Patel et al., "Crossing the Blood-Brain Barrier: Recent Advances in Drug Delivery to the Brain," CNS Drugs 31:109-133 (2017); Kabanov et al., "New Technologies for Drug Delivery across the Blood Brain Barrier," Curr Pharm Des., 10(12):1355-1363 (2004); Cheng et al., "Highly Stabilized Curcumin Nanoparticles Tested in an In Vitro Blood-Brain Barrier Model and in Alzheimer's Disease Tg2576 Mice," The AAPS Journal, vol. 15, no. 2, pp. 324-336 (2013); Lande et al. "Production of L-Leucine Nanoparticles under Various Conditions Using an Aerosol Flow Reactor Method," Journal of Nanomaterials, vol. 2008, article ID 680897 (2008).

In one embodiment, the pharmaceutical composition, e.g., comprising acetyl-L-leucine, or salt thereof, is formulated for direct delivery to the central nervous system (CNS), such as by injection or infusion. Formulations for and methods of direct delivery to the CNS are known in the art. See, e.g., U.S. Pat. No. 9,283,181. Examples of such administration include but are not limited to intranasal, intraventricular, intrathecal, intracranial, and delivery via nasal mucosal grafting.

In one embodiment, the pharmaceutical composition is formulated for (and administered by) intranasal delivery. See, e.g., Hanson et al., "Intranasal delivery bypasses the blood-brain barrier to target therapeutic agents to the central nervous system and treat neurodegenerative disease," *BMC Neurosci.* 9(Suppl 3):S5 (2008). In one embodiment, the pharmaceutical composition is formulated for (and administered by) delivery via a nasal mucosal graft. In one embodiment, the pharmaceutical composition is formulated for (and administered by) intracerebroventricular injection or infusion. In another embodiment, the pharmaceutical composition is formulated for (and administered by) intrathecal intracisternal injection or infusion. In one embodiment, the pharmaceutical composition is formulated for (and administered by) intrathecal lumbar injection or infusion.

Various techniques may be used including, without limitation, injection through a burrhole or cisternal or lumbar puncture or the like as known in the art. Various devices, whether internal (e.g., implanted) or external, may be used for delivery as known in the art, such as pumps, catheters, reservoirs, etc. In one embodiment, the administration interval is once every two weeks.

In one embodiment, the administration interval is once every month. In one embodiment, the administration interval is once every two months. In one embodiment, the administration interval is twice per month. In one embodiment, the administration interval is once every week. In one embodiment, the administration interval is twice or several times per week. In one embodiment, the administration interval is daily. In one embodiment, the administration is continuous, such as continuous infusion.

In one embodiment, the dose or amount equivalent of acetyl-leucine may adjusted to account for either its direct delivery to the CNS or its delivery across the blood-brain barrier.

A "therapeutically effective amount" of acetyl-leucine is any amount which, when administered to a subject, is the amount that is needed to produce the desired effect, which, for the present disclosure, can be therapeutic and/or prophylactic. The dose may be determined according to various parameters, such as the age, weight and condition of the patient to be treated; the route of administration; and the required regimen. A physician will be able to determine the required route of administration and dosage for any particular patient. For example, a daily dose may be from about 10 to about 225 mg per kg, from about 10 to about 150 mg per kg, or from about 10 to about 100 mg per kg of body weight.

As used herein, "treating" or "treatment" refers to any indicia of success in preventing, delaying the onset of, arresting, or ameliorating a disease, disorder, condition, or syndrome, e.g., late-onset neurodegenerative disease, in a subject, including any objective or subjective parameter such as abatement; remission; preventing, diminishing, inhibiting, or eliminating one or more symptoms; making the disease, disorder, condition, or syndrome more tolerable to the subject; slowing in the worsening of the disease, disorder, condition, or syndrome; or improving the physical or mental well-being of the subject in need thereof.

The terms "treating" or "treatment" also encompasses, e.g., inducing inhibition, regression, or stasis of the disease, disorder, condition, or syndrome. For example, treatment of a subject in need of treatment for a late-onset neurodegenerative disease includes reducing a symptom of the late-onset neurodegenerative disease in the subject, inducing clinical response, inhibiting or reducing progression of the late-onset neurodegenerative disease, or inhibiting or reducing a complications of the late-onset neurodegenerative disease.

Preventing, arresting, or ameliorating an injury or pathology of a disease, disorder, condition, or syndrome, such as preventing, diminishing, inhibiting, or eliminating one or more symptoms of disease, disorder, condition, or syndrome can be based on objective and/or subjective parameters, including, e.g., the results of physical examination(s), neurological examination(s), and/or psychiatric evaluation(s). The success of treatment for certain late-onset neurodegenerative diseases may be measured or evaluated by, for example, comparing the severity of the disease (e.g., objective and/or subjective parameters of NPC) before treatment with acetyl-leucine is initiated, with the severity of the disease (e.g., objective and/or subjective parameters of the late-onset neurodegenerative disease) following the initiation of treatment with acetyl-leucine. For example, the severity of the late-onset neurodegenerative disease may be assessed using a scale, index, rating, or score. In one embodiment, the treatment described herein improves such an assessment from a value or degree characteristic of a symptomatic subject to a value or degree characteristic of a non-symptomatic subject. In one embodiment, the treatment described herein improves such an assessment compared to a baseline. The baseline may be, for example, the subject's condition before initiating any treatment for the disease or before initiating treatment for the disease with acetyl-leucine. Alternatively, the baseline may be, for example, the subject's condition after a certain time period on treatment for the disease. In one embodiment, treatment with acetyl-leucine as described herein improves the subject's assessment (e.g., scale, index, rating, or score of objective and/or subjective parameters) compared to a baseline by at least 5%, at least 10%, at least 20%, at least 30%, at least 40%, or at least 50%. In one embodiment, assessment is improved by at least 60%, at least 70%, at least 80%, at least 90%, or 100%.

In one embodiment, the severity of the subject's late-onset neurodegenerative disease or symptom thereof may be quantified by neurological and/or neuropsychological assessments such as abdominal ultrasound with volumometry, video-oculography (VOG), and/or the testing battery proposed by the Consortium to Establish a Registry for Alzheimer's Disease (CERAD).

A "symptom" of a late-onset neurodegenerative disease, includes any clinical or laboratory manifestation associated with the late-onset neurodegenerative diseases, and is not limited to what the subject can feel or observe. The symptoms of late-onset neurodegenerative diseases are known in the art.

Symptoms of NPC include, but are not limited to, cerebellar ataxia (unsteady walking with uncoordinated limb movements), dysarthria (slurred speech), dysphagia (difficulty in swallowing), tremor, epilepsy, vertical supranuclear palsy (upgaze palsy, downgaze palsy, saccadic palsy or paralysis), sleep inversion, gelastic cataplexy (sudden loss of muscle tone or drop attacks), dystonia (abnormal movements or postures caused by contraction of agonist and antagonist muscles across joints), spasticity (velocity dependent increase in muscle tone), hypotonia, ptosis (drooping of the upper eyelid), microcephaly (abnormally small head), psychosis, progressive dementia, progressive hearing loss, bipolar disorder, major and psychotic depression that can include hallucinations, delusions, mutism, or stupor.

Symptoms of AD include, but are not limited to, difficulty performing familiar tasks, memory loss, disorientation to time and place, loss of good judgment, problems with abstract thinking, misplacing things, rapid mood swings, sudden and dramatic personality changes, loss of initiative, sleeping longer than usual, or loss of interest in usual activities Symptoms of amyotrophic lateral sclerosis (ALS) include, but are not limited to, muscle weakness or atrophy, spasticity, trouble swallowing or breathing, cramping, or stiffness of affected muscles; or slurred and nasal speech.

Symptoms of Parkinson's disease include, but are not limited to, tremor, bradykinesia, muscle stiffness, impaired posture and balance, loss of automatic movements, speech changes, or writing changes.

Symptoms of dementia include, but are not limited to, memory loss, which is usually noticed by a spouse or someone else, difficulty communicating or finding words, difficulty with visual and spatial abilities, such as getting lost while driving, difficulty reasoning or problem-solving, difficulty handling complex tasks, difficulty with planning and organizing, difficulty with coordination and motor functions, confusion, or disorientation.

In one embodiment, acetyl-leucine may be administered, for example, at a dose ranging from about 500 mg to about 30 g per day or ranging from about 500 mg to about 15 g per day, such as ranging from about 1.5 g to about 10 g per day, optionally by solid oral or liquid oral route. Acetyl-leucine, may be administered, for example, in a dose according to that of Tanganil®, which is prescribed to adults in a dose of 1.5 g to 2 g per day, 3-4 tablets in two doses, morning and evening.

If a single enantiomer, i.e., acetyl-L-leucine, is administered the doses may be reduced accordingly. For instance, if only acetyl-L-leucine is administered, the dose may range from about 250 mg to about 15 g per day, range from about 250 mg to about 10 g per day, or range from about 250 mg to about 5 g per day, such as from about 0.75 g to about 5 g per day.

In one embodiment, the administered dose ranges from about 1 g to about 30 g per day, from about 1 g to about 15 g per day, from about 1 g to about 10 g per day, or from about 1.5 g to about 7 g per day, from 15.1 g to about 30 g per day, 16 g to about 30 g per day, 17 g to about 30 g per day, 18 g to about 30 g per day, 19 g to about 30 g per day, or 20 g to about 30 g per day. It may be from about 2, 3, 4, 5, 6, 7, 8, 9, 10, 11, 12, 13, or 14 g to about 15 g per day. It may be from about 2, 3, 4, 5, 6, 7, 8 or 9 g to about 10 g per day. It may be from 15.1, 16, 17, 18, 19, 20, 21, 22, 23, 24, 25, 25, 27, 28, or 29 g to about 30 g per day. It may be more than about 1.5 g per day, but less than about 15, 14, 13, 12, 11, 10, 9, 8, 7, 6 or 5 g per day. In one embodiment, the dose ranges from about 4 g to about 6 g per day. In one embodiment, the dose ranges from about 4 g to about 5 g per day. In one embodiment, the dose is about 4.5 g per day. In one embodiment, the dose is about 5 g per day. In one embodiment, the dose is about 1 g per day, about 2 g per day, about 3 g per day, about 4 g per day, about 5 g per day, about 6 g per day, about 7 g per day, about 8 g per day, about 9 g per day, about 10 g per day, about 11 g per day, about 12 g per day, about 13 g per day, about 14 g per day, or about 15 g per day. In another embodiment, the dose is about 16 g per day, about 17 g per day, about 18 g per day, about 19 g per day, or about 20 g per day. In another embodiment, the dose is about 21 g per day, about 22 g per day, about 23 g per day, about 24 g per day, about 25 g per day, about 26 g per day, about 27 g per day, about 28 g per day, about 29 g per day, or about 30 g per day. In one embodiment, these doses are administered in a solid oral dosage form, notably tablets. In another embodiment, these doses are for acetyl-leucine when in its racemic form. Doses for acetyl-leucine when an enantiomeric excess is present may be lower, for example, around 50% lower. The above recited dose-ranges when halved are thus also explicitly encompassed by the present disclosure.

Also, in some embodiments, asymptomatic subjects may receive lower doses of acetyl-leucine, e.g., 1 g to 10 g per day, as compound to subjects that have been clinically diagnosed as having a late-onset neurodegenerative disease who may receive, e.g., 5 g to 15 g of acetyl-leucine per day.

In one embodiment, the total daily dose may be spread across multiple administrations, i.e. administration may occur two or more times a day to achieve the total daily dose. As an example, the required number of tablets to provide the total daily dose of acetyl-leucine may be split across two administrations (for example, in the morning and evening) or three administrations (for example, in the morning, noon, and evening). Each dose may be suitably administered with or without food. For example, acetyl-L-leucine or acetyl-DL-leucine may be dosed by about 1 or about 2 hours before meals, such as at least about 20 minutes, at least about 30 minutes, at least about 40 minutes, or at least about 1 hour before meals, or may be dosed by about 1, about 2, or about 3 hours after meals, such as waiting at least about 20 minutes, at least about 30 minutes, at least about 1 hour, at least about 1.5 hours, at least about 2 hours, or at least about 2.5 hours after meals. For example, a total daily dose of 4.5 g acetyl-DL-leucine may be administered as three Tanganil® (or equivalent) tablets before, with, or after breakfast, three further tablets before, with, or after lunch and three further tablets before, with, or after dinner.

Treatment duration may be, for example, about seven days or more, about two weeks or more, about three weeks or more, about one month or more, about six weeks or more, about seven weeks or more, or about two months or more. In one embodiment, it is about three months or more, about four months or more, about five months or more or about six months or more. The treatment duration may be about 1 year or more, about 2 years or more, about 4 years or more, about 5 years or more, or about 10 years or more. The treatment duration may be the life-time of the subject.

Any and all combinations of dosage form, dose amount, dosing schedule and treatment duration are envisaged and encompassed by the disclosure. In one embodiment, the dose is from about 4 g to about 10 g per day, taken across one, two, or three administrations per day, for a treatment duration of about two months or more. In another embodiment, the dose is more than 4 g but no more than 5 g per day, taken across one, two, or three administrations per day, for a treatment duration of about six months or more. The dosage form may be a solid oral dosage form, notably tablets.

Acetyl-leucine may be used as a monotherapy, e.g., used as the active agent alone, for treating or preventing the late-onset neurodegenerative disease, or the symptoms thereof, in a subject. Alternatively, acetyl-leucine may be used as an adjunct to, or in combination with, other known therapies for treating or preventing the late-onset neurodegenerative disease.

Also disclosed is a kit for treating, preventing, or delaying the onset of a late-onset neurodegenerative disease, comprising acetyl-leucine. The kit may further comprise instructions for using acetyl-leucine according to a method of the present disclosure and/or a means for diagnosing or prognosing the disease.

EXAMPLES

General Study Parameters

Twenty first-degree relatives of genetically and/or biochemically confirmed NPC patients participated (13 males, mean age 52.7±9.9, education years 14.2±2.4) were recruited between 2016 and 2018. All probands were molecularly-confirmed heterozygous NPC1 gene mutation carriers for this study. Participants were of German, Turkish, Slovakian, Spanish, and Swedish descent. None of the participants took neuropotent medication. The following battery was chosen to recapitulate characteristic features of symptomatic NPC disease and to screen for abnormalities suggestive of late-onset neurodegeneration. All underwent neurological evaluation with particular focus on movement abnormalities. A motor score was defined giving 1 point each for presence of a reduced arm swing, intention tremor, increased muscle tone, ankle clonus, gait abnormalities. Scores≥1 were considered pathological. Grooved PEG-board testing to assess fine motor function was performed as previously described (Strauss 2006). It is routinely administered in patients with lysosomal storage disorders (Bremova-Ertl et al. 2017).

Mood was evaluated using the Beck depression scale (Bech et al. 1961); REM-sleep behaviour was assessed using the REM-sleep Behaviour Disorder (RBD) questionnaire (Stiasny-Kolster et al. 2014). Scented Sniffin' Sticks pens were used to assess smell identification, threshold and discrimination (Hummel et al. 1997).

In seventeen subjects, standardized neuropsychological assessment was performed in their native language using the battery proposed by the Consortium to Establish a Registry for Alzheimer's Disease (CERAD) (Ehrensperger et al. 2010). The remaining three were too young for the CERAD analysis. In two individuals, a subset of tests could not be performed because of language incongruences (see Tables 2A and 2B). CERAD includes assessment of global cognitive function (mini mental state examination, [MMSE]), executive functions, e.g., trail making test (Arbuthnott et al. 2000; Sanchez-Cubillo et al. 2009)) to examine mental processing speed [TMT-A] and set-shifting [TMT-B], TMTB-A, which is a relatively pure indicator of executive control, lexical and semantic fluency), attention (verbal and visual span), memory (including the three components of encoding, storage and retrieval, i.e. word list direct recall [directCERAD], word list delayed recall [delayedCERAD], word list recognition [savings]), language (Boston naming test, [BNT]), and visuo-constructive functions. Constructional praxis (CP) copying task consists of four figures (circle, diamond, overlapping rectangles, Necker cube) was also assessed. The CLOX test, an executive clock drawing task, was also administered (Royall et al. 1998). Individual raw scores were transformed to z-scores based on a large database of healthy control subjects considering, age, education, and gender (Luppa et al. 2012).

Given the characteristic ocular motor deficits in NPC, i.e. vertical supranuclear gaze palsy, VOG was performed in 16 heterozygotes using a video-based eye-tracker system (Eye-SeeCam®, Munich, Germany) as previously described (Schneider et al. 2009). The data was compared to 36 age- and sex-matched controls. Briefly, the following parameters were assessed: reflexive saccades which reflect brainstem function, self-paced saccades (an ocular motor task with a cognitive dimension to assess the frontal eye field), smooth pursuit, gaze-holding, and horizontal vestibulo-ocular reflex.

Blood was analysed for NPC biomarkers, i.e. plasma chitotriosidase activity and concentration of cholestane-3β, 5α,6β-triol as previously described (Reunert et al 2015). Selected routine parameters including full blood count and routine liver function tests were also measured.

Abdominal ultrasound with volumometry was performed (n=12) to assess the size of liver and spleen, as used in routine clinical practice.

[18]FDG-PET (n=16) was performed using a Siemens Biograph 64 PET/CT scanner as previously described (Beyer et al. 2018; Brendel et al. 2017); visual judgment of significant hypometabolism in different brain areas was based on stereotactic surface projections and axial slices; a binarized decision of significant or non-significant hypometabolism was performed in clinical routine; for quantitative analyses PMOD Version 3.5 (PMOD Technologies Ltd., Zurich, Switzerland) was used for spatial normalization of all images to the Montreal Neurological Institute (MNI) space and for activity normalization by the global mean. Statistical parametric mapping (SPM) was performed using SPM12 implemented in Matlab (R2016). Subjects were compared against 23 age-matched in-house healthy controls (departmental data available) by a voxel-wise two-tailed Student's t-test after 8 mm Gaussian smoothing. The significance threshold was set to p<0.01 (uncorrected for multiple comparisons; k>20 voxel). Based on resulting significant clusters, uptake values from ten volumes-of-interest were extracted. They were as follows: left anterior cingulate cortex and bilateral posterior cingulate cortex, bilateral cerebellum, basal ganglia, parietal cortex left, bilateral temporal cortex, bilateral insular cortex, bilateral midbrain and tegmentum, and bilateral postcentral cortex.

Statistical Analysis

Statistical analysis and graphical design were performed using SPSS version 25.0.0 (IBM, Armonk, NY). Normality of data distribution was tested using the mean, median, SD, skewness, kurtosis, and box plots. For data that were normally distributed, t-test for related and non-related variables, respectively, were used ([18]FDG-PET outcomes). Data that were not normally distributed, nonparametric paired Wilcoxon test for related groups and non-paired testing using the Mann-Whitney-U test in case of non-related samples, were performed (VOG measures). Differences were considered significant if p<0.05. Spearmen's Correlation Coefficient was calculated to assess the relationships between clinical data and scores, neuropsychological scores and imaging data.

More than 80% of assessments were completed by all 20 participants. Demographic characteristics and key findings are summarized in Tables 1A-1C.

TABLE 1A

| Subject ID | Sex | Age | Country of origin | Genotype (NPC1) | Motor score [a] |
|---|---|---|---|---|---|
| 1 | M | 68 | GER | c.2660C > T | 2 |
| 2 | M* | 64 | GER | c.2861C > T [S954L] | 2 |
| 3 | F* | 55 | GER | c.2861C > T [S954L] | 0 |
| 4 | F^ | 53 | GER | c 3246-5__3246-7del[x] | 0 |
| 5 | M^ | 61 | GER | c 3246-5__3246-7del[x] | 5 |
| 6 | M | 51 | TUR | c.3246-25A > G[xx] | 1 |
| 7 | M° | 61 | GER | c.2861C > T | 0 |
| 8 | F° | 59 | GER | c.2776G > A | 1 |
| 9 | F | 54 | GER | c.2861C > T | 1 |
| 10 | M* | 25 | SLOV | c.2861C > T | 0 |
| 11 | M* | 62 | SLOV | c.2861C > T | 2 |
| 12 | F | 46 | GER | c.3010T > C | 1 |
| 13 | M | 55 | GER | c.2474A > G | 0 |
| 14 | M | 48 | GER | c.2474A < G | 1 |
| 15 | M^ | 39 | ESP | c.2978delG, | 2 |
| 16 | F^ | 39 | ESP | c.3245 + 1dup | 0 |
| 17 | F° | 49 | SWED | c.1211G > A | 0 |
| 18 | M° | 50 | SWED | c.1843C > T | 2 |

TABLE 1A-continued

| Subject ID | Sex | Age | Country of origin | Genotype (NPC1) | Motor score [a] |
|---|---|---|---|---|---|
| 19 | M* | 57 | GER | c.3182T > C | 1 |
| 20 | F* | 57 | GER | c.3182T > C | 1 |
| Abnormal (%) | | | | | 65% |

TABLE 1B

| Subject ID | Grooved-PEG board (Dominant) | Depression [b] | RBDSQ [c] | Smell test [d] |
|---|---|---|---|---|
| 1 | 11 | 10 | 1 | 13 |
| 2 | 9 | 0 | 1 | 13 |
| 3 | 14 | 22 | 6 | 13 |
| 4 | 15 | 14 | 9 | 12 |
| 5 | 8 | 5 | 4 | 13 |
| 6 | 13 | n.d. | 0 | 13 |
| 7 | 9 | 0 | 2 | 10 |
| 8 | 16 | 5 | 4 | 13 |
| 9 | 14 | 19 | 1 | 8 |
| 10 | 14 | n.d. | n.d. | 11 |
| 11 | 16 | n.d. | n.d. | 13 |
| 12 | 16 | 9 | 1 | 14 |
| 13 | 12 | 11 | 6 | 11 |
| 14 | 13 | 11 | 1 | 13 |
| 15 | 16 | 7 | 5 | 13 |
| 16 | 18 | n.d. | n.d. | 14 |
| 17 | 17 | 3 | 0 | 13 |
| 18 | 15 | 0 | 1 | 13 |
| 19 | 17 | 7 | 4 | 13 |
| 20 | 11 | 8 | 4 | 14 |
| Abnormal (%) | | 37.5% | 24% | 20% |

TABLE 1C

| Subject ID | Abdominal ultrasound [e] Spleen | Abdominal ultrasound [e] Liver | Chitotriosidase activity [nmol/h/ml] (norm ≤150) | Oxysterols [ng/µl] (norm ≤0.05) [f] | FDG PET [g] (visual rating 0-12) |
|---|---|---|---|---|---|
| 1 | – | + | 699.4 | 0.037 | 6 |
| 2 | – | ++ | 103.4 | 0.026 | 4 |
| 3 | – | – | 39.0 | 0.027 | 3 |
| 4 | – | + | 74.7 | 0.022 | 3 |
| 5 | – | + | 80.7 | 0.012 | 2 |
| 6 | n.d. | n.d. | 10.1 | 0.014 | n.d. |
| 7 | + | – | 164.5 | 0.064 | 6 |
| 8 | – | + | 33.4 | 0.063 | 1 |
| 9 | n.d. | n.d. | 45.2 | 0.02 | 5 |
| 10 | n.d. | n.d. | n.d. | n.d. | 0 |
| 11 | n.d. | n.d. | n.d. | n.d. | 2 |
| 12 | n.d. | n.d. | 35.4 | 0.021 | n.d. |
| 13 | ++ | ++ | 171.9 | 0.187 | 1 |
| 14 | ++ | – | 113.7 | 0.048 | 1 |
| 15 | ++ | – | 20.8 | 0.052 | 0 |
| 16 | – | – | 85.6 | 0.028 | n.d. |
| 17 | – | – | 28.8 | 0.021 | 2 |
| 18 | – | ++ | 57.7 | 0.037 | 1 |
| 19 | n.d. | n.d. | 51.6 | 0.054 | 4 |
| 20 | – | – | 77.8 | 0.075 | n.d. |
| Abnormal (%) | 71% | | 17% | 33% | 50% |

Abbreviations for Tables 1A-1C: n.d.=no data. N. y. f=not yet found. Country of origin: GER-Germany, TUR-Turkey, SLOV-Slovakia, ESP-Spain, SWED-Sweden. The symbols *, °, ^ indicate participants from the same family. [X]An intronic variant not previously described in the literature (class 3), leading to skipping of exon 22. [XX]This intronic mutation has not been described yet. ENST00000269228, position in the genome: chr18:21115689. a=A motor score was defined giving 1 point each for presence of a reduced arm swing, intention tremor, increased muscle tone, ankle clonus, gait abnormalities. Scores≥1 were considered pathological; b=using the Beck Depression Inventory with 0-9 indicating that a person is not depressed, 10-18 indicating mild-moderate depression, 19-29 indicating moderate-severe depression and 30-63 indicating severe depression; c=REM sleep behavior was assessed using the validated a 10-item patient self-rating questionnaire (maximum total score 13 points) covering the clinical features of RBD; values≥5 are considered pathological; d=Odor identification was performed using Sniffin's sticks; results<12 are considered pathological. Apart from subject 11, all were non-smokers; e=Ultrasound findings were scored as follows: – for normal findings, + for mild enlargement of liver and/or spleen, ++ for definite organomegaly of liver and/or spleen; f=Oxysterols (cholestane-3β,5α,6β-triol); g=$^{18}$FDG-PET was rated as 1, 2, or 3 when discrete, moderate or definite abnormalities were present in the parietal cortex, the temporal cortex, the anterior cingulate cortex and the cerebellum; normal PET findings were rated as "0". The resulting subscores of all regions were summed to a combined FDG-PET score.

Example 1

Clinical Findings

Motor abnormalities were present in 13 of 20 participants (65%), as detected on clinical examination or PEG-board testing. Six subjects (of 16; 37.5%) reported symptoms of mild or moderate depression (BDI≥10), screening for REM sleep behaviour disorder was positive in almost one quarter (4 of 17; 24%); four participants (20%) were hyposmic. Chitotriosidase activity and cholestantriol levels were abnormal in three and six subjects (17%; 33%), respectively. Transaminase levels (GPT, GOT and GGT) were elevated in one subject (subject #11).

Example 2

Cognitive Testing

The results of neuropsychological testing by CERAD subdomain are presented in Tables 2A and 2B and FIG. 1. Twelve participants completed the whole CERAD battery. Global cognitive performance was impaired in three subjects who scored 26 or less on the MMSE (mean MMSE across all participants 27.87±2.59 with a minimum of 21 points in subject #6; mean age-dependent z-score −1.38±1.69 with a minimum of −4.98 in subject #6). Word list retrieval was ≤80% in eight heterozygotes (minimum, 58% in subject #6). Word list recognition discriminability was overall preserved with only mild abnormalities in three subjects. Word list savings varied between 58% and 113% with a mean of 90.6±15% (percentage>100% reflects better performance than in the sex-/age-matched normative sample). Mean percental savings of characters was 86.3±20% (range, 44-111%). The phonematic fluency reached a mean of 12.4±5.4 words, Boston Naming Test (BNT) yielded 14.4±1.8 words, and an average of 22.7±6.4 animals were named in the verbal fluency test. Mean TMT A was 30.76±10.84 s; mean TMT B was 68.14±24.22 s. TMT B–A time (calculated as a subtraction of TMT-A (numbers) and TMT-B (number and letters)) varied remarkably between subjects, yielding a mean of 37.38±21.29 s with a maximum of 93.10 s. Four subjects scored in the pathological range when related to an age-matched normative sample (z-value≤−1). The CLOX test was abnormal in five participants (score≤9).

TABLE 2A

| Subject ID | Sex | Age | Education (yrs) | MMSE | Word list total | Word list recall | Savings %[a] | Figure drawing |
|---|---|---|---|---|---|---|---|---|
| Maximum score | | | | 30 | | 10 | 100 | 11 |
| 1 | M | 68 | 11 | 25 | 16 | 5 | 84 | 9 |
| 2 | M | 64 | 17 | 27 | 19 | 7 | 100 | 8 |
| 3 | F | 55 | 13 | 24 | 20 | 9 | 113 | 9 |
| 4 | F | 53 | 13 | 30 | 23 | 8 | 80 | 9 |
| 5 | M | 61 | 16 | 29 | 23 | 6 | 75 | 9 |
| 6 | M | 51 | 9 | 21 | 22 | 7 | 88 | 8 |
| 7 | M | 61 | 13 | 29 | 18 | 4 | 58 | 10 |
| 8 | F | 59 | 14 | 29 | 18 | 7 | 88 | 9 |
| 9 | F | 54 | 12 | 29 | 24 | 8 | 80 | 7 |
| 12[$] | F | 46 | 15 | 29 | 29 | 10 | 100 | 10 |
| 13 | M | 55 | 17 | 30 | 21 | 9 | 113 | 10 |
| 14[$] | M | 48 | 13 | 28 | 19 | 7 | 100 | 10 |
| 15[$] | M | 39 | 17 | 30 | 30 | 10 | 100 | 11 |
| 17[$$] | F | 49 | 17 | n/a | n/a | n/a | n/a | n/a |
| 18[$$] | M | 50 | 17 | n/a | n/a | n/a | n/a | n/a |
| 19 | F | 57 | 13 | 29 | 21 | 9 | 100 | 9 |
| 20 | M | 57 | 14 | 29 | 20 | 8 | 80 | 8 |

TABLE 2B

| Subject ID | Savings % of characters[a] | Temporal Sum[b] | Executive function Sum[c] | TMT A [sec] | TMT B [sec] | TMT B-A [sec] | CLOX[d] |
|---|---|---|---|---|---|---|---|
| Maximum score | 100 | 5 | 5 | | | | 15 |
| 1 | 100 | 1 | 3 | 48.9 | 119.2 | 70.3 | 15 |
| 2 | 88 | 0 | 2 | 43 | 85 | 42 | 8 |
| 3 | 89 | 1 | 0 | 22.3 | 58.2 | 35.9 | 10 |
| 4 | 111 | 1 | 0 | 36.1 | 48.3 | 12.2 | 7 |
| 5 | 67 | 2 | 1 | 41.5 | 52.2 | 10.7 | 9 |
| 6 | 88 | 0 | 3 | 25 | 118.1 | 93.1 | 11 |
| 7 | 60 | 3 | 3 | 28.4 | 87.6 | 59.2 | 13 |
| 8 | 44 | 2 | 1 | 44.5 | 80.4 | 35.9 | 12 |
| 9 | 129 | 1 | 0 | 25.7 | 44.8 | 19.1 | 9 |
| 12[$] | 80 | n/a | 0 | 18 | 54.7 | 36.7 | 13 |
| 13 | 70 | 1 | 0 | 27.6 | 65.1 | 37.5 | 11 |
| 14[$] | 90 | n/a | 1 | 24.5 | 63.2 | 38.7 | 9 |
| 15[$] | 82 | n/a | 0 | 15.3 | 32.6 | 17.3 | 11 |
| 17[$$] | n/a | n/a | 0 | 13.4 | 46 | 32.6 | 12 |
| 18[$$] | n/a | n/a | 2 | 32.7 | 79 | 46.3 | 10 |
| 19 | 100 | 1 | 1 | 44 | 65 | 21 | 13 |
| 20 | 100 | 0 | 1 | 32 | 59 | 27 | 13 |

Abbreviations for Tables 2A and 2B: $=patients were too young for formal CERAD analysis. z-scores could thus not be calculated. $$=patients were non-fluent in German, thus language-dependent aspects of cognitive testing were not performed. z-scores could thus not be calculated. Probands 10, 11 and 16 did not participate in the CERAD testing. a=Subjects with >100% performed better in the delayed than the direct recall; b=Sum scores were calculated based on total word list, word list recall, word list savings %, word list discriminability, figure savings %. Scores>2 were considered pathological; c=Sum scores were calculated based on phonetic and semantic verbal fluency, TMT A, TMT B, TMT B−A. Scores>2 were considered pathological; d=Raw scores<10 on the CLOX test are considered pathological.

Example 3

Video-Oculography Findings

For typical ocular motor findings in an NPC1 heterozygote (subject #7) see FIG. 2A-D. Briefly, reflexive vertical and horizontal saccades were abnormal in NPC heterozygotes compared to healthy controls. To elaborate, in the vertical plane, reflexive saccade duration and duration to reach the peak velocity (duration max) were shorter in heterozygotes for downward saccades in response to 10° and 20° stimuli (duration: p<0.01, duration max: p<0.05), FIG. 3A. This was also the case for latency of downward vertical saccades (p<0.05), FIG. 3A. In the horizontal plane, reflexive saccade duration was shorter in heterozygotes in response to 30° stimulus to the left (p=0.001) and duration max was significantly shorter both right- (p<0.001) and leftward (p<0.01), compared to normal subjects, FIG. 3B (for overview, see Tables 3A-3C).

NPC heterozygotes also displayed abnormal self-paced saccades, both in the vertical and horizontal dimension. In contrast to reflexive saccades, they showed prolonged mean downward saccade duration (vertical, p<0.001; horizontal, p<0.01), FIG. 3C The average peak velocity of horizontal self-paced saccades was 425.9±98.1°/s in mutation carriers and 478.8±85°/s, thus reduced in the mutation carriers (p<0.05).

TABLE 3A

| (n = 36) | Peak velocity, [°/s] | Amplitude [°] | Latency [s] | Duration [s] | Duration Maximal [s] |
|---|---|---|---|---|---|
| | | | Vertical saccades Down | | |
| NPC1 Heterozygotes | 398.4 ± 88.6 | 20.1 ± 1.4 | 0.2 ± 0.11 | 0.14 ± 0.04 | 0.06 ± 0.02 |
| Healthy controls | 435.3 ± 82.6 | 20.1 ± 2.1 | 0.2 ± 0.04 | 0.15 ± 0.06 | 0.06 ± 0.02 |
| p-value | NS | NS | <0.05* | <0.01** | <0.05* |
| | | | Horizontal saccades Right | | |
| NPC1 Heterozygotes | 486.6 ± 95.96 | 28.4 ± 2.1 | 0.19 ± 0.05 | 0.18 ± 0.08 | 0.05 ± 0.01 |
| Healthy controls | 512 ± 88.5 | 29 ± 2.3 | 0.2 ± 0.05 | 0.22 ± 0.095 | 0.07 ± 0.02 |
| p-value | NS | NS | NS | NS | <0.001*** |

TABLE 3B

| (n = 36) | Peak velocity, [°/s] | Amplitude [°] | Latency [s] | Duration [s] | Duration Maximal [s] |
|---|---|---|---|---|---|
| | | | Vertical saccades Up | | |
| NPC1 Heterozygotes | 406.5 ± 396.3 | 18.4 ± 2.1 | 0.177 ± 0.029 | 0.146 ± 0.065 | 0.05 ± 0.01 |
| Healthy controls | 396.3 ± 66.8 | 18.5 ± 1.7 | 0.194 ± 0.041 | 0.204 ± 0.096 | 0.06 ± 0.024 |
| p-value | NS | NS | NS | NS | NS |
| | | | Horizontal saccades Left | | |
| NPC1 Heterozygotes | 468.5 ± 92.1 | 28.4 ± 2.9 | 0.178 ± 0.039 | 0.163 ± 0.06 | 0.056 ± 0.02 |
| Healthy controls | 478.2 ± 82.2 | 29.1 ± 2.6 | 0.186 ± 0.047 | 0.23 ± 0.1 | 0.073 ± 0.025 |
| p-value | NS | NS | NS | <0.001*** | <0.01** |

TABLE 3C

| (n = 36) | Peak velocity, [°/s] | Amplitude [°] | Latency [s] | Duration [s] | Duration Maximal [s] |
|---|---|---|---|---|---|
| | | | Mean vertical saccades | | |
| NPC1 Heterozygotes | 402.5 ± 78.9 | 19.3 ± 1.6 | 0.186 ± 0.058 | 0.144 ± 0.048 | 0.055 ± 0.01 |
| Healthy controls | 415.8 ± 61.7 | 19.6 ± 1.6 | 0.199 ± 0.037 | 0.177 ± 0.068 | 0.062 ± 0.2 |
| p-value | NS | NS | NS | <0.05* | 0.057 |
| | | | Mean horizontal saccades | | |
| NPC1 Heterozygotes | 477.6 ± 90 | 28.4 ± 2.1 | 0.18 ± 0.04 | 0.172 ± 0.067 | 0.053 ± 0.012 |
| Healthy controls | 495.3 ± 83.3 | 29.1 ± 2.1 | 0.2 ± 0.04 | 0.224 ± 0.092 | 0.069 ± 0.02 |
| p-value | NS | NS | NS | <0.01** | <0.001*** |

The duration of self-paced saccades was longer than that of reflexive saccades, both in NPC heterozygotes and controls (p<0.001; p<0.001). Finally, both smooth pursuit and horizontal vestibulo-ocular reflex (VOR gain 0.93) were within the 95% CI for normal subjects.

Regarding gaze-holding, in heterozygotes the vertical and horizontal component of gaze-holding nystagmus on upgaze was higher than in healthy controls (p<0.05), FIG. 3D. Moreover, slow-phase velocity of gaze-holding nystagmus to the right was also higher than in healthy controls (p<0.01). Video-Oculographic Instructions:

Reflexive Saccades: Subjects made visually guided vertical and horizontal saccades in response to stimuli of 1.33° visual angle (expression changing smileys). Vertical saccades, elicited by the stimuli of 10° and 20° amplitude over the range±10° from the central position and horizontal saccades of 15° and 30° amplitude, over the range±15° from the central position, were required. Participants performed seven saccades in response to the stimulus of each size along both axes. The targets were presented in pseudorandom order for the time of 2500 ms with additional variation of 500 ms.

Self-paced saccades: Subjects were instructed to switch arbitrarily between presented visual stimuli as quickly as possible ("make it a race"). Visual stimulation were permanently visible two dots at 10° up and down, with stimulus amplitude of 20° in the vertical plane. Horizontally, there were two permanently visible dots at 15° on the right and left side, with stimulus amplitude of 30°. Test duration yielded 30 sec. Intersaccadic interval and total number of performed saccades, were evaluated.

Smooth pursuit: After the initial fixation period of 2 s, the target subtending visual angle of 0.57° moved in 3 cycles at 0.1 and 3 cycles at 0.2 Hz frequencies, yielding peak target velocities of 9.5°/s, 18.8°/s horizontal and 6.4°/s, 12.6°/s, with ±15° amplitude horizontally (right and left) from the central position, and then ±10° vertically (up and down) from the central position without a break.

Gaze-holding: Participants were asked to foveate a point of 0.57° visual angle, presented on a monitor without moving the head. The point was primarily positioned at the level of the eyes, then changing the eccentricity from 15° left to 15° right (altogether 30° horizontally) and 10° down. Stimulus was presented for 10 s at each position.

Vestibulo-ocular reflex: Participants were instructed to foveate a white point of visual angle of 0.3° positioned 2 m from the wall. Ten±two head impulses were performed to each side.

Ocular motor data of heterozygotes were compared with the age- and sex-matched heathy controls.

Example 4

Imaging Results

[18]FDG-PET examination was performed in 16 heterozygotes. Visual rating of stereotactic surface projections by two experiences nuclear medicine physicians revealed significant hypometabolism patterns in 8/16 cases (FIG. 4). In case of disagreement a consensus was achieved. Subregions rated positive for hypometabolism were the cerebellum (8/16), anterior cingulate cortex (8/16), parieto-occipital (8/16) and temporal (5/16). Significant hypometabolism was more likely at older age as assessed by averaged ages of binarized negative or positive rates subjects (neg: 47.8y, pos: 60.0y, p=0.012). Hypometabolism also negatively correlated with education years.

Voxel-based analysis compared to age-matched controls indicated decreased metabolic rates in large clusters of the bilateral cerebellum (−8.8%), bilateral inferior temporal gyms (−8.0%), the left anterior cingulate cortex (−9.4%), and the left parietal lobe (−10.8%) (FIG. 5), Smaller clusters of increased brain metabolism were detected in midbrain and tegmentum, right insula, followed by bilateral postcentral region, left insula, and posterior cingulate cortex (in the abovementioned order: 15.5%, 7.9%, 6.8%, 6.4% and 5.5%).

Abdominal ultrasound revealed organomegaly of liver and/or spleen of mild or medium-degree in 10 out of 14 participants, who underwent the examination.

Example 5

Correlations

Blood Parameters with Ocular Motor Function, Ultrasound and PET Findings

Cholestantriol concentrations were positively related to the duration of upward and downward saccades, (up: $\rho=0.720$, $p<0.001$; down: $\rho=0.679$, $p<0.002$), duration to reach the peak velocity of upward saccades (duration max up: $\rho=0.598$, $p<0.01$), as well as duration of saccades to the right ($\rho=0.657$, $p<0.01$). This was also the case for chitotriosidase activity and duration and duration max of vertical saccades ($\rho=0.630$, $p<0.01$, $\rho=0.529$, $p<0.05$). The volume of liver and spleen ($\rho=0.592$, $p<0.01$) and metabolic activity of the right insula ($\rho=0.568$, $p<0.05$) were also positively related to cholestantriol concentration.

Motor Function and Cognitive Measures

The clinical motor score was related to the second round of re-called words ($\rho=0.636$, $p<0.01$). Parameters of the grooved pegboard task positively correlated with domains of CERAD battery, in particular with the memory recall (PH: $\rho=0.696$, $p<0.01$; NP: $\rho=0.639$, $\rho=0.01$; both hands: $\rho=0.533$, $p<0.05$; PEG assembly: $\rho=0.687$, $p<0.01$), but also with the full score of executive function ($\rho=-0.512$, $p<0.05$), S-words ($\rho=0.546$, $p<0.01$), word list recall $3^{rd}$ round ($\rho=0.577$, $p<0.05$), direct recall ($\rho=0.696$ $p<0.01$); and correlated negatively to z-values of intrusions ($\rho=-0.640$, $p<0.01$), and discrimination recall ($\rho=-0.532$, $p<0.05$).

Motor Performance and Ocular Motor Function

The clinical motor score was negatively related to mean horizontal saccadic duration, especially to the left (both sides: $\rho=-0.480$, $p<0.05$; left: $\rho=-0.479$, $p<0.05$). The grooved pegboard test and smell test did not significantly correlate with ocular motor measures.

Ocular Motor Function and Cognitive Performance

Duration of upward saccades was positively related to discrimination recognition ($\rho=0.578$, $p<0.05$). Duration to reach the peak velocity of upward ($\rho=-0.548$, $p<0.05$) and leftward saccades ($\rho=0.631$, $p<0.05$) were related to word list discrimination recall.

Peak velocity of horizontal saccades also correlated with constructional copying ($\rho=0.555$, $p<0.05$) but was negatively related to percentage of savings ($\rho=-0.692$, $p<0.01$). The normative age-matched database-corrected savings (z-value) of savings percentage also negatively correlated with velocity of horizontal saccades ($\rho=-0.679$, $p<0.01$), but not of vertical saccades.

Vertical smooth pursuit correlated with percentage of savings ($\rho=0.613$, $p<0.05$). Z-value of percentage of savings was negatively related to horizontal smooth pursuit and vertical gain ($\rho=-0.579$, $p<0.05$; $\rho=-0.521$, $p<0.05$). Both vertical ($\rho=0.623$, $p<0.05$; $\rho=0.550$, $p<0.05$) and horizontal ($\rho=0.826$, $p<0.0001$; $\rho=0.779$, $p<0.001$) smooth pursuit correlated with constructional copying tasks including its z-values.

Brain Metabolism and Motor, Cognitive and VOG Measures

Glucose metabolic rates in the brainstem, but not in postcentral and/or cerebellar areas were negatively correlated with the motor score ($\rho=-0.614$, $p<0.01$). Of the cognitive parameters, the BNM test z-value showed a positive relationship with the left insula ($\rho=0.609$, $p<0.05$). Intrusions were related to left ACC ($\rho=-0.597$, $p<0.05$) and right temporal areas ($\rho=-0.615$, $p<0.05$). Posterior cingular cortex was negatively associated with duration until maximal velocity of vertical saccades ($\rho=-0.535$, $p<0.05$). Postcentral area correlated negatively with duration of horizontal saccades to the left ($\rho=-0.642$, $p<0.01$). Left parietal region correlated positively with ($\rho=0.561$, $p<0.05$) peak velocity of horizontal saccades.

Example 6

Discussion of Results

Twenty asymptomatic heterozygote NPC1 gene mutation carriers were studied to identify potential early signs of neurodegeneration using a combined approach of different methods (e.g. clinical assessment, cognition testing, ocular motor examination, imaging of visceral organs and brain function, blood analysis, etc.). The test battery was deliberately chosen to detect early stages of neurodegeneration, e.g. PD or dementia (Postuma et al. 2016).

The main findings are as follows. First, NPC heterozygotes recapitulate characteristic features of symptomatic NPC disease: NPC heterozygotes demonstrated oculomotor abnormalities with prolonged duration of saccades, horizontally more than vertically, as well as abnormal horizontal self-paced saccades. There was also the presence of hepatosplenomegaly and increased levels of blood biomarkers characteristic of NPC disease.

Second, NPC heterozygosity is associated with late-onset neurodegeneration. The clinically asymptomatic mutation carriers showed impaired age-corrected cognitive performance, especially affecting visuo-constructive function, verbal fluency and executive function. PET imaging revealed significant abnormal glucose metabolic rates in half of 16 subjects scanned, including one with bilateral abnormalities. This argues for functional consequences of clinically silent heterozygous gene variations.

Third, two novel intronic mutations in the NPC1 gene are described.

Impaired vertical saccades due to supranuclear involvement, later in the disease course also gaze palsy (with combined impairment of smooth pursuit) are a leading symptom of NPC disease. Reflexive and self-paced saccadic duration and reflexive saccades duration to reach the peak velocity are sensitive markers that allow discrimination between NPC1 heterozygotes and healthy controls. Previous studies found that intersaccadic intervals and the absolute number of performed cognitively-driven saccades as good biomarkers to track NPC disease progression (Abel et al. 2009). This study did not find abnormalities of these markers. But prolongation of duration was found in the cohort of clinically asymptomatic NPC heterozygote mutation carriers. Since both peak velocity and duration are driven by burst neurons in the brainstem, prolongation of self-paced saccades might be the earliest component of pathognomonic vertical supranuclear saccade palsy in NPC patients. The discrepancy between the duration of reflexive (shorter than controls) and self-paced saccades (longer than controls) is not completely understood. Without wishing to be bound by any particular theory, prolongation of self-paced saccades might reflect impaired cognition and processing speed in NPC heterozygotes due to the functional disturbance of frontal eye field (FEF). In contrast to NPC patients, horizontal self-paced saccades in heterozygotes were more affected than vertical ones, pointing to a possible additional disturbance of saccadic burst neurons in pons, not midbrain. This is aligned with the brain metabolism analyses.

Vertical saccade duration and maximal duration of rightward horizontal saccades correlated consistently with the volume of left temporal area. The strongest relationships showed abnormalities of upward, followed by downward saccade duration. This is in line with the increase of more than 15% in midbrain metabolic rates, where the vertical saccadic burst neurons are located in the rostral interstitial nucleus of medial longitudinal fascicle (riMLF), thus explaining the short latency and duration of downward vertical saccades. The underlying mechanisms are not fully understood. Without wishing to be bound by any particular theory, there may be paradoxical over-activation in order to compensate for presumable underlying functional deficits. This may be a mechanism similar to vestibular compensation after a unilateral vestibular loss, when the activation is modulated during the recovery process to compensate for the functional deficits (Dieringer et al. 1995; Brandt et al. 1997). No peripheral vestibular impairment in heterozygotes as reflected by intact horizontal vestibulo-ocular reflexes was found similar to findings in homozygous patients with NPC disease (Bremova et al. 2016).

Recent studies showed a specific pattern of brain metabolic abnormality in patients with NPC disease: bilateral hypometabolism in the frontal, prefrontal cortex and bilateral parietotemporal regions, and hypermetabolism in the parietal-occipital white matter, lenticular nucleus of the basal ganglia, cerebellum and pons, which correlated with disease progression (Benussi et al. 2015; Huang et al. 2011; Kumar et al. 2011). Hypometabolism in frontal and parieto-temporal cortices of NPC heterozygotes was found but the most obvious cluster of hypometabolism was in the cerebellum. The cerebellar hypometabolism (which is often severely affected in NPC disease and also plays a key role in saccadic regulation) did not show any significant relationship with any of the investigated ocular motor parameters, especially not smooth pursuit.

Hepatomegaly and splenomegaly are core features of NPC. Indeed, NPC is recognized as a significant cause of liver disease in early life. In those with later onset, it often (50-90%) remains asymptomatic and unrecognized clinically (Patterson et al. 2013). Consistent splenomegaly in heterozygous gene mutation carriers has also been reported (Harzer et al. 2014). In the studied cohort, five participants (more than one third) had organomegaly, two of whom presenting with isolated splenomegaly. If present, particularly when combined with neurodegenerative or psychiatric features, this is highly suggestive of NPC (Patterson et al. 2012). One of the two subjects with isolated splenomegaly also screened positive for REM sleep behavior disorder (RBD). RBD and olfactory loss are markers for which there is now very strong evidence that they have the ability to predict conversion to PD (Postuma et al. 2016).

Finally, levels of NPC biomarkers chitotriosidase and/or cholestantriol, were increased in some of the NPC heterozygotes.

This testing battery was deliberately chosen to include markers of early PD including hyposmia. Four participants (20% of subjects) had a reduced sense of smell, one of whom also had abnormal chitotriosidase activity levels. The 'Sniffin Sticks' (Hummel et al. 1997) used here enable testing of three aspects of smell, i.e. smell identification, threshold and discrimination. A reduced sense of smell is associated with Lewy body pathology affecting the olfactory bulbs and cortex (Hoyles et al. 2013). However, as olfaction also depends on an intact memory, impairment may also be present in degenerative non-synucleinopathies associated with cognitive impairment where disruption of specific associative areas involved in olfactory processing may play a role, e.g. vascular dementia, AD and FTLD (Olichney et al. 2005; Gray et al. 2001; Orasji et al. 2016).

Psychometric testing using the CERAD battery was also performed. This revealed impaired overall cognitive function with deficits of visuo-constructive abilities and verbal fluency, as well as impaired executive function (i.e., processing speed, set-shifting), especially in heterozygotes #1, 6, 8 and 14, albeit there was no relationship between brain metabolism, especially frontal and temporo-parietal lobes, and cognitive scores.

To compare, in symptomatic NPC disease cognitive dysfunction manifests as aphasia, apraxia, memory impairment and deficits of executive functions and attention (Heitz et al. 2017; Sevin et al. 2007), particularly in those who presented with a "dementia plus" syndrome (Cupidi et al. 2017) with underlying frontal hypometabolism (Huang et al. 2011; Kumar et al. 2011; Battisti et al. 2003). However, given a relatively preserved verbal episodic memory in NPC patients, compared to Alzheimer disease, it was recently concluded that delayed verbal memory recall may be the best distinguishing factor between the two disorders (Johnen et al. 2018). Thus, the pattern of NPC heterozygotes in this study is in line with the findings in symptomatic NPC disease.

In this study, NPC mutation carriers impaired executive function also manifested as prolonged duration of self-paced saccades seen carriers which have a considerable cognitive component controlled by the frontal eye field (Leigh et al. 2015). Self-paced saccades are frequently impaired in PD (Pretegiani et al. 2017) and dementia including frontotemporal variants (Douglass et al. 2018).

Lastly, two novel variations in intronic regions of NPC1 gene have been identified. The first, c.3246-25A>G is located in a conserved NPC1 cysteine-rich domain and might impact binding motives for splicing regulatory elements (SRP) proteins, which can lead to the inclusion or exclusion of exons (Greer et al. 1999). Findings were confirmed by the translated RNA. The mutation segregated in the family with the disease, where both parents (consanguine marriage) are heterozygous and both affected children are homozygous. The second, c.3246-5_3246-7delx, results in a 3 bp intronic deletion with skipping of exon 22. Neither variation was detected by routine genetic testing.

Example 7

NPC Heterozygote Studies

Heterozygous carriers of NPC1 that are either asymptomatic or showing preclinical symptoms of NPC disease, e.g., oculomotor abnormalities, hepatosplenomegaly, elevated levels of chitotriosidase in blood or plasma, and/or elevated levels of cholestane-3β,5α,6β-triol in blood or plasma, will be identified and treated with 5-15 g/day of acetyl-leucine for one to thirty six months. These subjects will be assessed for quality of life (function), gait, and/or ocular motor function before initiating treatment with acetyl-leucine and at regular intervals during the treatment cycle. The subjects may also undergo neurological evaluations and their blood or plasma may be analysed for chitotriosidase activity and cholestane-3β,5α,6β-triol concentration during the treatment cycle. $^{18}$FDG-PET examinations may also be performed before, during, or after treatment with acetyl-leucine. Administration of acetyl-leucine is expected to benefit heterozygous carriers of NPC1 who are at risk of developing late-onset neurodegenerative disease. These benefits include, but are not limited to, improved cognitive function, e.g., as determined by CERAD, decreased levels of chitotriosidase and/or cholestane-3β,5α,6β-triol in blood or plasma, improved ocular motor function, e.g., improved reflexive vertical and horizontal saccades, self-paced saccades, and/or gaze-holding, reduced hypometabolism, or reduced organomegaly of liver or spleen.

REFERENCES

1. Patterson M. Niemann-Pick Disease Type C. In: Pagon R A, Adam M P, Ardinger H H, et al., eds. GeneReviews®. Seattle (Wash.), 1993.
2. Kresojevic N, Dobricic V, Svetel M, Kostic V. Mutations in Niemann Pick type C gene are risk factor for Alzheimer's disease. Medical hypotheses 2014; 83:559-562.
3. Sidransky E, Nalls M A, Aasly J O, et al. Multicenter analysis of glucocerebrosidase mutations in Parkinson's disease. N Engl J Med 2009; 361:1651-1661.
4. Josephs K A, Matsumoto J Y, Lindor N M. Heterozygous Niemann-Pick disease type C presenting with tremor. Neurology 2004; 63:2189-2190.
5. Harzer K, Beck-Wodl S, Bauer P. Niemann-pick disease type C: new aspects in a long published family—partial manifestations in heterozygotes. JIMD Rep 2014; 12:25-29.
6. Kluenemann H H, Nutt J G, Davis M Y, Bird T D. Parkinsonism syndrome in heterozygotes for Niemann-Pick C1. Journal of the neurological sciences 2013; 335: 219-220.
7. Cupidi C, Frangipane F, Gallo M, et al. Role of Niemann-Pick Type C Disease Mutations in Dementia. J Alzheimers Dis 2017; 55:1249-1259.
8. Zech M, Nubling G, Castrop F, et al. Niemann-Pick C disease gene mutations and age-related neurodegenerative disorders. PLoS One 2013; 8:e82879.

9. Probert F, Ruiz-Rodado V, Vruchte D T, et al. NMR analysis reveals significant differences in the plasma metabolic profiles of Niemann Pick C1 patients, heterozygous carriers, and healthy controls. Sci Rep 2017; 7:6320.
10. Strauss E. A Compendium of Neuropsychological Tests: Administration, Norms, and Commentary. In: Oxford University Press, 2006: 1042 ff.
11. Bremova-Ertl T, Schiffmann R, Patterson M C, et al. Oculomotor and Vestibular Findings in Gaucher Disease Type 3 and Their Correlation with Neurological Findings. Front Neurol 2017; 8:711.
12. Beck A T, Ward C H, Mendelson M, Mock J, Erbaugh J. An inventory for measuring depression. Archives of general psychiatry 1961; 4:561-571.
13. Stiasny-Kolster K, Mayer G, Schafer S, Moller J C, Heinzel-Gutenbrunner M, Oertel W H. The REM sleep behavior disorder screening questionnaire—a new diagnostic instrument. Movement disorders: official journal of the Movement Disorder Society 2007; 22:2386-2393.
14. Hummel T, Sekinger B, Wolf S R, Pauli E, Kobal G. 'Sniffin' sticks': olfactory performance assessed by the combined testing of odor identification, odor discrimination and olfactory threshold. Chem Senses 1997; 22:39-52.
15. Ehrensperger M M, Berres M, Taylor K I, Monsch A U. Early detection of Alzheimer's disease with a total score of the German CERAD. J Int Neuropsychol Soc 2010; 16:910-920.
16. Arbuthnott K, Frank J. Trail making test, part B as a measure of executive control: validation using a set-switching paradigm. J Clin Exp Neuropsychol 2000; 22:518-528.
17. Sanchez-Cubillo I, Perianez J A, Adrover-Roig D, et al. Construct validity of the Trail Making Test: role of task-switching, working memory, inhibition/interference control, and visuomotor abilities. J Int Neuropsychol Soc 2009; 15:438-450.
18. Royall D R, Cordes J A, Polk M. CLOX: an executive clock drawing task. Journal of neurology, neurosurgery, and psychiatry 1998; 64:588-594.
19. Luppa M, Riedel-Heller S G, Luck T, et al. Age-related predictors of institutionalization: results of the German study on ageing, cognition and dementia in primary care patients (AgeCoDe). Soc Psychiatry Psychiatr Epidemiol 2012; 47:263-270.
20. Schneider E, Villgrattner T, Vockeroth J, et al. EyeSeeCam: an eye movement-driven head camera for the examination of natural visual exploration. Ann N Y Acad Sci 2009; 1164:461-467.
21. Reunert J, Lotz-Havla A S, Polo G, et al. Niemann-Pick Type C-2 Disease: Identification by Analysis of Plasma Cholestane-3beta,5alpha,6beta-Triol and Further Insight into the Clinical Phenotype. JIMD Rep 2015; 23:17-26.
22. Beyer L, Meyer-Wilmes J, Schonecker S, et al. Clinical Routine FDG-PET Imaging of Suspected Progressive Supranuclear Palsy and Corticobasal Degeneration: A Gatekeeper for Subsequent Tau-PET Imaging? Front Neurol 2018; 9:483.
23. Brendel M, Schonecker S, Hoglinger G, et al. [(18)F]-THK5351 PET Correlates with Topology and Symptom Severity in Progressive Supranuclear Palsy. Frontiers in aging neuroscience 2017; 9:440.
24. Havla J B, T.; Sztatecsny, C.; Moser, M.; Lotz-Havla, A.; Maier, E.; Schinner, R.; Kümpfel, T.; Strupp, M.; Schneider, S. A. Retinal axonal degeneration in Niemann Pick type C disease and asymptomatic mutation carriers. (in preparation).

25. Postuma R B, Berg D. Advances in markers of pro-dromal Parkinson disease. Nat Rev Neurol 2016; 12:622-634.

26. Abel L A, Walterfang M, Fietz M, Bowman E A, Velakoulis D.
Saccades in adult Niemann-Pick disease type C reflect frontal, brainstem, and biochemical deficits. Neurology 2009; 72:1083-1086.

27. Dieringer N. 'Vestibular compensation': neural plasticity and its relations to functional recovery after labyrinthine lesions in frogs and other vertebrates. Prog Neurobiol 1995; 46:97-129.

28. Brandt T, Strupp M, Arbusow V, Dieringer N. Plasticity of the vestibular system: central compensation and sensory substitution for vestibular deficits. Advances in neurology 1997; 73:297-309.

29. Gunther L, Beck R, Xiong G, et al. N-acetyl-L-leucine accelerates vestibular compensation after unilateral labyrinthectomy by action in the cerebellum and thalamus. PLoS One 2015; 10:e0120891.

30. Bremova T, Krafczyk S, Bardins S, Reinke J, Strupp M. Vestibular function in patients with Niemann-Pick type C disease. Journal of neurology 31. Benussi A, Alberici A, Premi E, et al. Phenotypic heterogeneity of Niemann-Pick disease type C in monozygotic twins. Journal of neurology 2015; 262:642-647.

32. Huang J Y, Peng S F, Yang C C, Yen K Y, Tzen K Y, Yen R F. Neuroimaging findings in a brain with Niemann-Pick type C disease. J Formos Med Assoc 2011; 110:537-542.

33. Kumar A, Chugani H T. Niemann-Pick disease type C: unique 2-deoxy-2[(1)(8)F] fluoro-D-glucose PET abnormality. Pediatric neurology 2011; 44:57-60.

34. Patterson M C, Mengel E, Wijburg F A, et al. Disease and patient characteristics in NP-C patients: findings from an international disease registry. Orphanet J Rare Dis 2013; 8:12.

35. Patterson M C, Hendriksz C J, Walterfang M, Sedel F, Vanier M T, Wijburg F. Recommendations for the diagnosis and management of Niemann-Pick disease type C: an update. Molecular genetics and metabolism 2012; 106:330-344.

36. Scaglione C, Vignatelli L, Plazzi G, et al. REM sleep behaviour disorder in Parkinson's disease: a questionnaire-based study. Neurological sciences: official journal of the Italian Neurological Society and of the Italian Society of Clinical Neurophysiology 2005; 25:316-321.

37. Hoyles K, Sharma J C. Olfactory loss as a supporting feature in the diagnosis of Parkinson's disease: a pragmatic approach. Journal of neurology 2013; 260:2951-2958.

38. Olichney J M, Murphy C, Hofstetter C R, et al. Anosmia is very common in the Lewy body variant of Alzheimer's disease. Journal of neurology, neurosurgery, and psychiatry 2005; 76:1342-1347.

39. Gray A J, Staples V, Murren K, Dhariwal A, Bentham P. Olfactory identification is impaired in clinic-based patients with vascular dementia and senile dementia of Alzheimer type. Int J Geriatr Psychiatry 2001; 16:513-517.

40. Orasji S S, Mulder J L, de Bruijn S F, Wirtz P W. Olfactory dysfunction in behavioral variant frontotemporal dementia. Clinical neurology and neurosurgery 2016; 141:106-110.

41. Heitz C, Epelbaum S, Nadjar Y. Cognitive impairment profile in adult patients with Niemann pick type C disease. Orphanet J Rare Dis 2017; 12:166.

42. Sevin M, Lesca G, Baumann N, et al. The adult form of Niemann-Pick disease type C. Brain: a journal of neurology 2007; 130:120-133.

43. Battisti C, Tarugi P, Dotti M T, et al. Adult onset Niemann-Pick type C disease: A clinical, neuroimaging and molecular genetic study. Movement disorders: official journal of the Movement Disorder Society 2003; 18:1405-1409.

44. Johnen A, Pawlowski M, Duning T. Distinguishing neurocognitive deficits in adult patients with NP-C from early onset Alzheimer's dementia. Orphanet J Rare Dis 2018; 13:91.

45. Leigh J R Z, D. S. The Neurology of Eye Movements. Fifth edition: Oxford University Press, 2015.

46. Pretegiani E, Optican L M. Eye Movements in Parkinson's Disease and Inherited Parkinsonian Syndromes. Front Neurol 2017; 8:592.

47. Douglass A, Walterfang M, Velakoulis D, Abel L. Behavioral Variant Frontotemporal Dementia Performance on a Range of Saccadic Tasks. J Alzheimers Dis 2018; 65:231-242.

48. Patterson M C, Vecchio D, Jacklin E, et al. Long-term miglustat therapy in children with Niemann-Pick disease type C. Journal of child neurology 2010; 25:300-305.

49. Greer W L, Dobson M J, Girouard G S, Byers D M, Riddell D C, Neumann P E. Mutations in NPC1 highlight a conserved NPC1-specific cysteine-rich domain. American journal of human genetics 1999; 65:1252-1260.

50. Yu W, Ko M, Yanagisawa K, Michikawa M. Neurodegeneration in heterozygous Niemann-Pick type C1 (NPC1) mouse: implication of heterozygous NPC1 mutations being a risk for tauopathy. The Journal of biological chemistry 2005; 280:27296-27302.

All of the features described herein (including any accompanying claims, abstract and drawings), and/or all of the steps of any method so disclosed, may be combined with any of the above aspects in any combination, except combinations where at least some of such features and/or steps are mutually exclusive.

It is to be understood that the foregoing embodiments and exemplifications are not intended to be limiting in any respect to the scope of the disclosure, and that the claims presented herein are intended to encompass all embodiments and exemplifications whether or not explicitly presented herein.

All patents, patent applications, and publications cited herein are fully incorporated by reference in their entirety.

What is claimed is:

1. A method of:
(i) treating, preventing, or delaying the onset of a late-onset neurodegenerative disease;
(ii) treating, preventing, or delaying the onset of one or more symptoms of a late-onset neurodegenerative disease; or
(iii) treating, preventing, or delaying the onset of a late-onset neurodegenerative disease and preventing or delaying the onset of one or more symptoms of a late-onset neurodegenerative disease,
the method comprising administering a therapeutically effective amount of acetyl-leucine to a human subject in need thereof, wherein the subject is a heterozygous NPC1 gene mutation carrier.

2. The method of claim 1, wherein the subject has any one or more of:
(a) an elevated level of chitotriosidase or cholestane-3β, 5α,6β-triol in blood;
(b) oculomotor abnormalities; or
(c) hepatosplenomegaly.

3. The method of claim 1, wherein the subject is asymptomatic for the late-onset neurodegenerative disease at the time of the initial administration of the acetyl-leucine.

4. The method of claim 1, wherein the method is for preventing or delaying the onset of the late-onset neurodegenerative disease.

5. The method of claim 4, wherein the method is for delaying the onset of the late-onset neurodegenerative disease.

6. The method of claim 1, wherein the late-onset neurodegenerative disease is Niemann-Pick type C, Alzheimer's disease, amyotrophic lateral sclerosis, Parkinson's disease, or dementia.

7. The method of claim 1, wherein the method is for preventing or delaying the onset one or more symptoms of the late-onset neurodegenerative disease.

8. The method of claim 7, wherein the method is for delaying the onset one or more symptoms of the late-onset neurodegenerative disease.

9. The method of claim 7, wherein the late-onset neurodegenerative disease is Niemann-Pick type C, Alzheimer's disease, amyotrophic lateral sclerosis, Parkinson's disease, or dementia.

10. The method of claim 9, wherein the late-onset neurodegenerative disease is Niemann-Pick type C, and the one or more symptoms comprise cerebellar ataxia, dysarthria, dysphagia tremor, epilepsy, vertical supranuclear palsy, sleep inversion, gelastic cataplexy, dystonia, spasticity, hypotonia, ptosis, microcephaly, psychosis, progressive dementia, progressive hearing loss, bipolar disorder, or depression.

11. The method of claim 9, wherein the late-onset neurodegenerative disease is Alzheimer's disease, and the one or more symptoms comprise difficulty performing familiar tasks, memory loss, disorientation to time and place, loss of good judgment, problems with abstract thinking, misplacing things, rapid mood swings, sudden and dramatic personality changes, loss of initiative, sleeping longer than usual, or loss of interest in usual activities.

12. The method of claim 9, wherein the late-onset neurodegenerative disease is amyotrophic lateral sclerosis, and the one or more symptoms comprise muscle weakness or atrophy, spasticity, trouble swallowing or breathing, cramping, or slurred and nasal speech.

13. The method of claim 9, wherein the late-onset neurodegenerative disease is Parkinson's disease, and the one or more symptoms comprise tremor, bradykinesia, muscle stiffness, impaired posture and balance, loss of automatic movements, speech changes, or writing changes.

14. The method of claim 9, wherein said late-onset neurodegenerative disease is dementia, and the one or more symptoms comprise memory loss, difficulty communicating or finding words, difficulty with visual and spatial abilities, difficulty reasoning or problem-solving, difficulty handling complex tasks, difficulty with planning and organizing, difficulty with coordination and motor functions, confusion, or disorientation.

15. The method of claim 1, wherein 1 gram to 30 grams of acetyl-leucine are administered to the subject per day.

16. The method of claim 1, wherein the acetyl-leucine is administered to the subject in combination with another therapeutic agent.

17. The method of claim 1, wherein acetyl-DL-leucine is administered to the subject.

18. The method of claim 1, wherein acetyl-L-leucine is administered to the subject.

19. The method of claim 1, wherein the NPC1 gene mutation is a c.3246-25A>G mutation.

20. The method of claim 1, wherein the NPC1 gene mutation is a c.3246-5_3246-7del mutation.

\* \* \* \* \*